(12) United States Patent
Gouin et al.

US011389466B2

(10) Patent No.: US 11,389,466 B2
(45) Date of Patent: Jul. 19, 2022

(54) MULTIVALENT FUCOSE DERIVATIVES FOR USE AS A DRUG

(71) Applicants: UNIVERSITE DE NANTES, Nantes (FR); CENTRE NATIONAL DE LA RECHERCHE SCIENTIFIQUE, Paris (FR)

(72) Inventors: Sébastien Gouin, Thouare sur Loire (FR); Sami Brument, Vertou (FR); Annabelle Varrot, Champ sur Drac (FR); Patrice Lepape, Vertou (FR)

(73) Assignees: UNIVERSITE DE NANTES, Nantes (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 20 days.

(21) Appl. No.: 16/485,899

(22) PCT Filed: Feb. 15, 2018

(86) PCT No.: PCT/EP2018/053843
§ 371 (c)(1),
(2) Date: Aug. 14, 2019

(87) PCT Pub. No.: WO2018/149945
PCT Pub. Date: Aug. 23, 2018

(65) Prior Publication Data
US 2020/0268782 A1    Aug. 27, 2020

(30) Foreign Application Priority Data
Feb. 15, 2017  (EP) .................................. 17156368

(51) Int. Cl.
*A61K 31/7056*  (2006.01)
*A61K 47/69*    (2017.01)
*A61K 31/724*   (2006.01)
*C07H 15/26*    (2006.01)
*A61K 47/61*    (2017.01)

(52) U.S. Cl.
CPC ........ *A61K 31/7056* (2013.01); *A61K 31/724* (2013.01); *A61K 47/6951* (2017.08); *C07H 15/26* (2013.01); *A61K 47/61* (2017.08)

(58) Field of Classification Search
CPC .............. A61K 31/7056; A61K 31/724; A61K 47/6951
See application file for complete search history.

(56) References Cited

FOREIGN PATENT DOCUMENTS

JP    2010202810 A    9/2010

OTHER PUBLICATIONS

Zhang (Journal of the American Chemical Society; 2014, 136, 4325-4332 and supporting Information).*
International Search Report, dated Apr. 19, 2018, from corresponding PCT application No. PCT/EP2018/053843.
European search report, dated Jul. 19, 2017, from corresponding European Patent Application No. EP17 15 6368.
Written Opinion (PCT/ISA/237) dated Apr. 19, 2018, by the Swedish Patent Office as the International Searching Authority for PCT Application No. PCT/EP2018/053843.
Qiang Zhang et al.; Dendritic Cell Lectin-Targeting Sentinel-like Unimolecular Glycoconjugates To Release an Anti-HIV Drug; Journal Of The American Chemical Society; Mar. 19, 2014; pp. 4325-4332; vol. 136, No. 11.
Isabelle Deguise et al.; Synthesis of glycodendrimers containing both fucoside and galactoside residues and their binding properties to Pa-IL and PA-IIL lectins from Pseudomonas aeruginosa; New Journal of Chemistry; Jan. 1, 2007; pp. 1321; vol. 31, No. 7.
Renato Ribeiro-Viana et al.; BODIPY-Labeled DC-SIGN-Targeting Glycodendrons Efficiently Internalize and Route to Lysosomes in Human Dendritic Cells; BIOMACROMOLECULES; Oct. 8, 2012; pp. 3209-3219; vol. 13, No. 10.
Caroline Ligeour et al.; Synthesis of branched-phosphodiester and mannosecentered fucosylated glycoclusters and their binding studies with Burkholderia ambifaria lectin (BambL); RSC Advances; Jan. 1, 2013; pp. 19515; vol. 3, No. 42.
Amine M. Boukerb et al.; Antiadhesive Properties of Glycoclusters against Pseudomonas aeruginosa Lung Infection; Journal of Medicinal Chemistry; Dec. 26, 2014; pp. 10275-10289; vol. 57, No. 24.
Kevin Buffet et al.; Fucofullerenes as tight ligands of RSL and LecB, two bacterial lectins; Organic & Biomolecular Chemistry; Jan. 1, 2015; pp. 6482-6492; vol. 13, No. 23.
Nicolas Galanos et al.; Pentavalent pillar[S]arene-based glycoclusters and their multivalent binding to pathogenic bacterial lectins; Organic & Biomolecular Chemistry; Jan. 1, 2016; pp. 3476-3481; vol. 14, No. 13.
Stephane P. Vincent et al.; Biologically Active Heteroglycoclusters Constructed on a Pillar[5]arene-Containing [2] Rotaxane Scaffold; Chemistry A European Journal Communication; Nov. 3, 2015; pp. 88-92; vol. 22, No. 1.
François Morvan; Fucosylated Pentaerythrityl Phosphodiester Oligomers (PePOs): Automated Synthesis of DNA-Based Glycoclusters and Binding to Pseudomonas aeruginosa Lectin (PA-IIL); Bioconjugate Chemistry; Sep. 1, 2007; pp. 1637-1643; vol. 18, No. 5.

* cited by examiner

*Primary Examiner* — Pancham Bakshi
(74) *Attorney, Agent, or Firm* — Nixon & Vanderhye

(57) ABSTRACT

Disclosed is a compound bearing at least two fucose moieties for its use as a drug in the prevention or treatment of infections caused by *Aspergillus* spp, the compound having a molecular weight included from 0.6 to 340 kDa, in particular from 0.6 to 2 kDa or from 1 to 7 kDa or from 2 to 10 kDa or from 5 to 340 kDa.

20 Claims, 4 Drawing Sheets

MULTIVALENT FUCOSE DERIVATIVES FOR USE AS A DRUG

Figure 1:
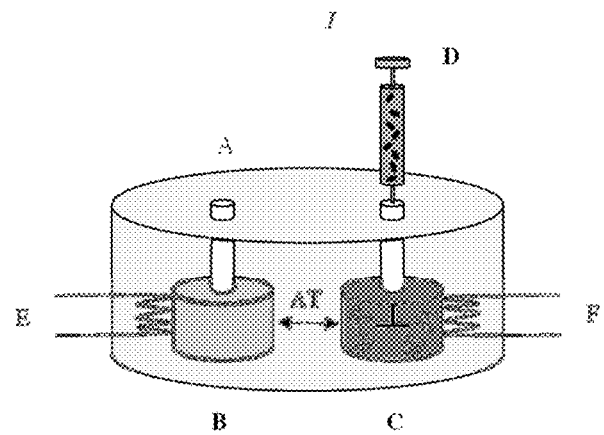
Figure 1:
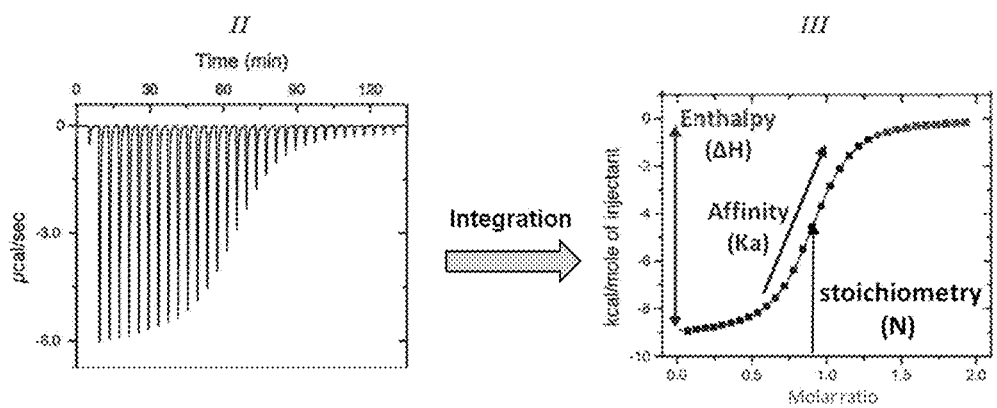

The present Invention relates to multivalent fucose derivatives for use as a drug. More especially, the present Invention relates to multivalent fucose derivatives for use as a drug in the prevention or treatment of infections caused by *Aspergillus* spp.

Invasive aspergillosis is a major cause of mortality in severely immunocompromised patients such as in allograft or leukemic patients. This pathogen is also involved in allergic forms that weaken the patient with cystic fibrosis, bronchopulmonar chronic obstructive disease (BPCO) and asthma, in aspergilloma and in chronic pulmonary aspergillosis. Nowadays the preventive and therapeutic strategies of these aspergillosis face problems of toxicity and resistance to antifungal agents.

The treatment of aspergillosis rests on azole derivatives (itraconazole, voriconazole, . . . ) which generate problems of innate or acquired resistance to treatment. However, amphotericin B, which has a broad spectrum, exhibits significant renal toxicity, whereas echinocandins, a new class of antifungals, have little activity on *Aspergillus* spp. Apart from systemic treatments, the inhalation of antifungals constitutes today a therapeutic alternative but not conceivable in prophylaxis given the long-term toxicity.

One objective of the present invention is to provide a compound for use as a drug in the prophylaxis of infections caused by *Aspergillus* spp.

Another aim of the present invention is to provide a compound for use as a drug in the treatment of infections caused by *Aspergillus* spp.

Another aim of the present invention is to provide a compound bearing at least two fucose moieties.

The present invention relates to a compound bearing at least two fucose moieties for its use as a drug in the prevention or treatment of infections caused by *Aspergillus* spp, said compound having a molecular weight comprised from 0.6 to 340 kDa, in particular from 0.6 to 2 kDa or from 1 to 7 kDa or from 2 to 10 kDa or from 5 to 340 kDa.

In particular, the molecular weight of the compound is from 0.6 to 2 kDa which includes a molecular weight of 0.6, 0.7, 0.8, 0.9, 1.0, 1.1, 1.2, 1.3, 1.4, 1.5, 1.6, 1.7, 1.8, 1.9 and 2 kDa. According to the present Invention, a compound with a molecular weight comprised from 0.6 to 2 kDa corresponds to a compound having a divalent scaffold. According to the present Invention, the expression "divalent scaffold" refers to a scaffold bearing 2 sites each covalently linked to a fucose moiety. Examples of divalent scaffold include alkyl chains and polyethylene glycol chains.

In particular, the molecular weight of the compound is from 1 to 7 kDa which includes a molecular weight of 1, 1.5, 2, 2.5, 3, 3.5, 4, 4.5, 5, 5.5, 6, 6.5 and 7 kDa.

According to the present Invention, a compound with a molecular weight comprised from 1 to 7 kDa corresponds to compound having a cyclic hexa- to octavalent scaffold. According to the present Invention, the expression "cyclic hexa- to octavalent scaffold" refers to a scaffold bearing 6, 7 or 8 sites each covalently linked to a fucose moiety, tethered through flexible linkers. Examples of cyclic hexa- to octavalent scaffold include calixarenes and cyclodextrins. In particular, the molecular weight of the compound is from 2 to 10 kDa which includes a molecular weight of 2, 2.5, 3, 3.5, 4, 4.5, 5, 5.5, 6, 6.5, 7, 7.5, 8, 8.5, 9, 9.5 and 10 kDa. According to the present Invention, a compound with a molecular weight comprised from 2 to 10 kDa corresponds to a compound having a polyhedral, cage-like, octavalent scaffold. According to the present Invention, the expression "polyhedral, cage-like, octavalent scaffold" refers to a scaffold bearing 8 sites each covalently linked to a fucose moiety. Examples of polyhedral, cage-like, octavalent scaffold include fullerenes and polyhedral oligomeric silsesquioxane (POSS).

In particular, the molecular weight of the compound is from 5 to 340 kDa which includes a molecular weight of 5, 10, 15, 20, 25, 30, 40, 50, 60, 70, 80, 90, 100, 125, 150, 175, 200, 225, 250, 275, 300, 325 and 340 kDa.

According to the present Invention, a compound with a molecular weight comprised from 5 to 340 kDa corresponds to a compound having a linear ultravalent scaffold. According to the present Invention, the expression "linear ultravalent scaffold" refers to a scaffold bearing at least 23 sites each covalently linked to a fucose moiety. Examples of linear ultravalent scaffold include polymers such as pullulan and dextran.

According to the Invention, the expression "prevention" relates to prophylaxis and consists of measures taken for disease prevention, as opposed to disease treatment. Disease prevention relies on anticipatory actions.

According to the Invention, the expression "treatment" relates to all appropriate means for stopping a disease, or for curing a patient.

According to the Invention, the expression "infections caused by *Aspergillus* spp" relates to infections that are caused by the fungus of the *Aspergillus* genus such as an aspergillosis.

The present Invention is based on the unexpected blocking of the *Aspergillus* spp lectin AFL by the compound of the Invention. This lectin is found on the surface of the *Aspergillus* spp spores and allows the fungus to adhere on the glycans of the host cells (Houser et al, Plos One, 2013, 8, e83077). The AFL lectin is also called FleA. This antiadhesive property enables the compounds of the Invention to be used as a drug to prevent and/or treat diseases caused by the *Aspergillus* spp.

In an advantageous embodiment, the present Invention relates to a compound for its use, said compound being of formula (I)

$$A\text{-}(D)_i\text{-}B\text{---}C \qquad (I)$$

wherein
i is equal to 0 or 1;
A is selected from

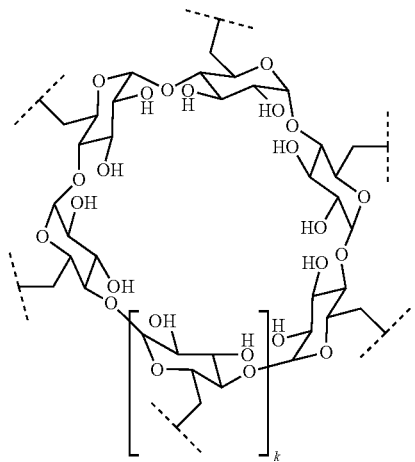

(A1)

k being equal to 1, 2, or 3; k being in particular equal to 1;

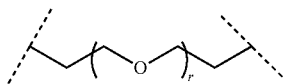 (A2)

r being comprised from 1 to 30, in particular from 1 to 4, from 5 to 9, from 10 to 15, from 16 to 20, from 21 to 25 or from 26 to 30;

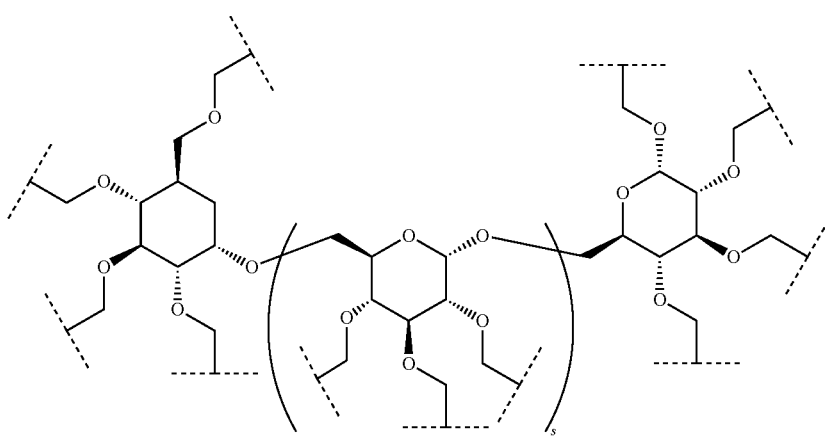 (A3)

s being comprised from 5 to 300; in particular from 60 to 80;

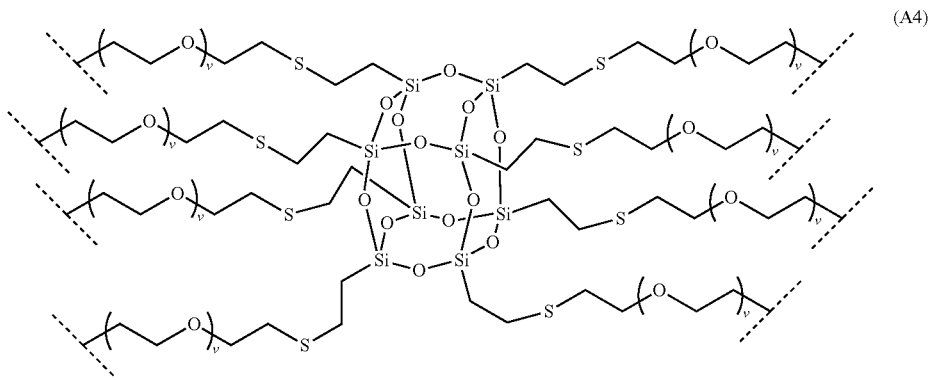 (A4)

v being comprised from 0 to 10; in particular from 1 to 8; preferably v being equal to 3;
B is of formula

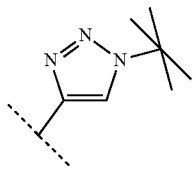 (B)

C is of formula

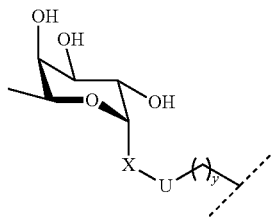 (C)

y being equal to 0 or 1;
X being selected from O, S or $CH_2$;

U being selected from

m being comprised from 0 to 8, n being comprised from 0 to 8,

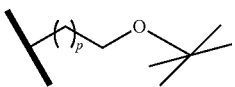

p being comprised from 1 to 10,

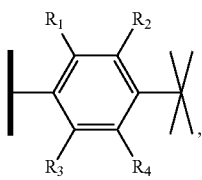

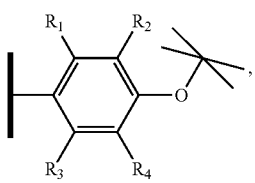

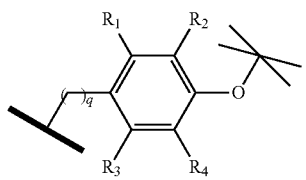

q being comprised from 1 to 10,

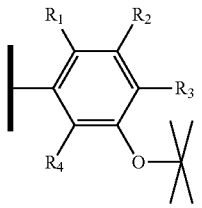

or

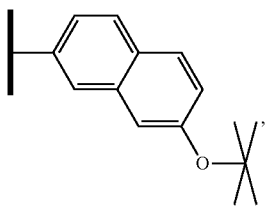

$R_1$, $R_2$, $R_3$ and $R_4$ being independently from each other selected from H, $COCH_3$, $NH_2$, $NO_2$, NHAc, OH, OMe, COOH, COOMe, CONHMe, Cl, Br, I, F, SMe or Me;

provided that y+n or y+m is different from 0;
in particular, m being comprised from 1 to 5;
in particular, n being comprised from 0 to 5;
D being selected from

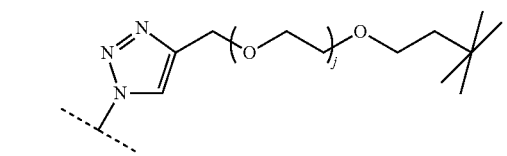

j being comprised from 0 to 8.

A is the scaffold, D is an optional spacer, B is a triazole spacer and C is a fucose moiety.

The dashed line " . . . " and the crossed lines " ⨯ " indicate the sites of a selected group each covalently linked to its neighbor.

On a selected group, the presence of more than one dashed line " . . . " indicates the sites each covalently linked to identical substituents. This means that the scaffold A is always linked to more than one time the same $(D)_j$-B—C group.

On a selected group, the presence of one dashed line " . . . " and one crossed lines " ⨯ " indicate the sites each covalently linked to two different substituents.

For example, if the scaffold is A2

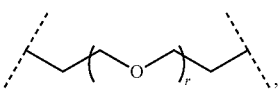

and the triazole spacer is B

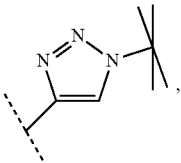

then the formed A2-B group represents

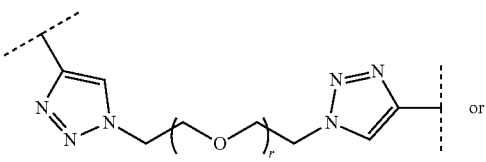 or

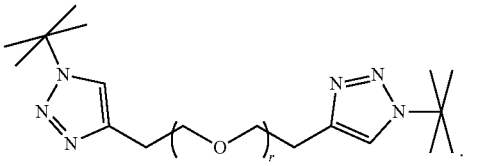

The triazole spacer B

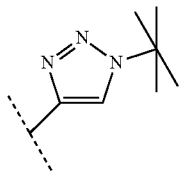

is linked to A-(D)$_i$ and C. The A-(D)$_i$ group can either be linked to the nitrogen or to the carbon atom of the triazole, the C group being linked to the other atom. For example, if B is linked to A-(D)$_i$ through the nitrogen atom of the triazole, C is linked to the triazole through its carbon atom to form a A-(D)$_i$-B—C group of formula

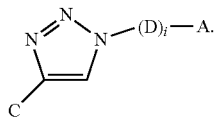

According to the present Invention, a polyethylene glycol group can be written as

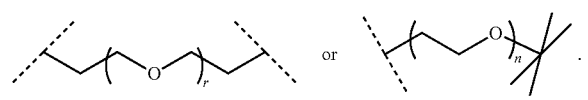

The bold line " ■ " appearing on the U groups represents the connection point to the X groups, U and X belonging to the fucose moiety C.

The zigzag bond " ⌇ " means that the stereochemistry of the linked double bond is either Z or E.

In an advantageous embodiment, the present Invention relates to a compound for its use, said compound being of formula (I)

$$A\text{-}(D)_i\text{-}B\text{—}C \quad (I)$$

wherein
i is equal to 0 or 1;
A is selected from

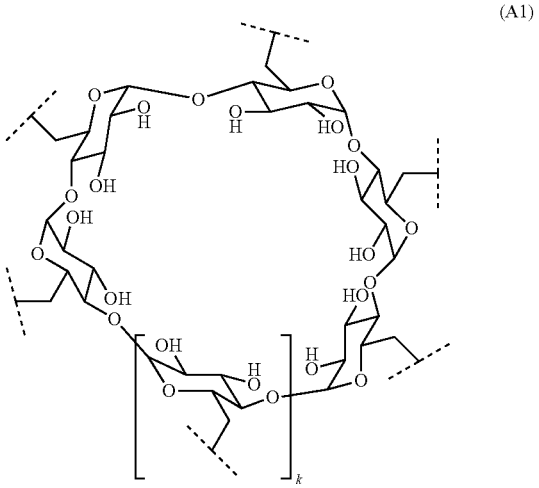

(A1)

k being equal to 1, 2, or 3; k being in particular equal to 1;

(A2)

r being comprised from 1 to 30, in particular from 1 to 4, from 5 to 9, from 10 to 15, from 16 to 20, from 21 to 25 or from 26 to 30;

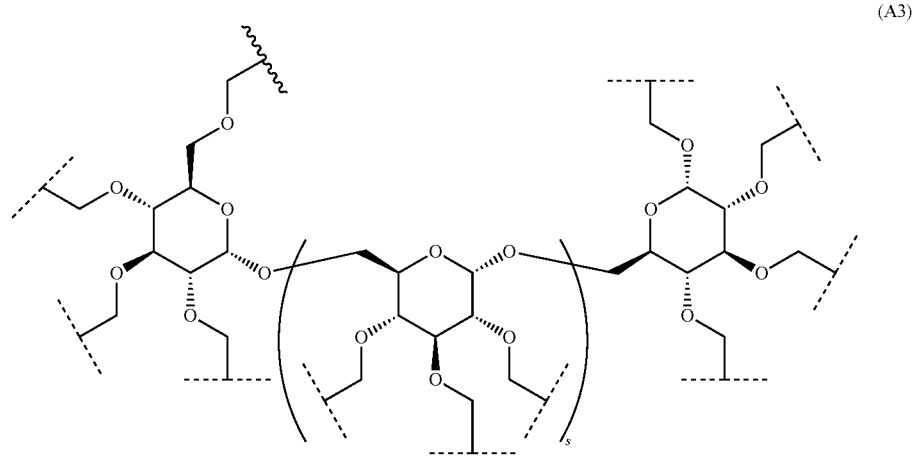

(A3)

s being comprised from 5 to 300; in particular from 60 to 80;

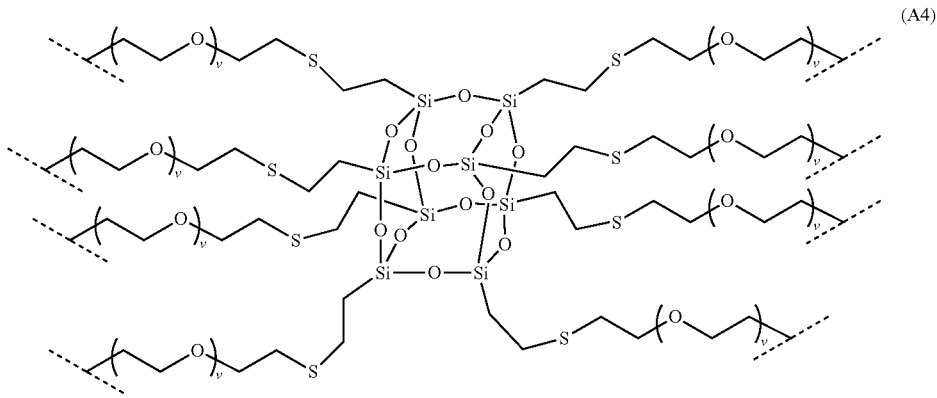
(A4)

v being comprised from 0 to 10; in particular from 1 to 8: preferably v being equal to 3;

B is of formula

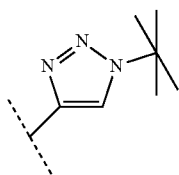
(B)

C is of formula

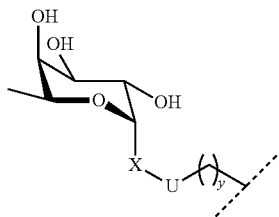

y being equal to 1;
X being selected from O, S or $CH_2$;
U being selected from

m being comprised from 0 to 8,

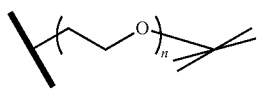

n being comprised from 0 to 8, or

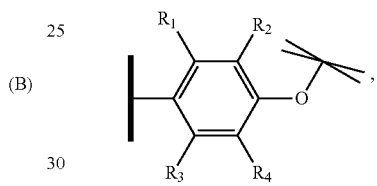

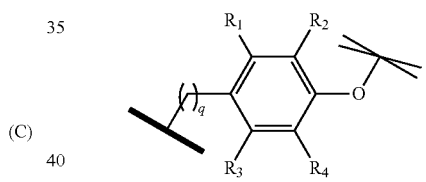
(C)

q being comprised from 1 to 10,
$R_1$, $R_2$, $R_3$ and $R_4$ being independently from each other selected from H, $COCH_3$, $NH_2$, $NO_2$, NHAc, OH, OMe, COOH, COOMe, CONHMe, Cl, Br, I, F, SMe or Me;
in particular, m being comprised from 1 to 5;
in particular, n being comprised from 0 to 5;
D being selected from

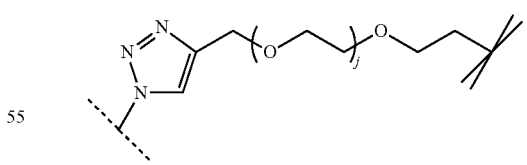

j being comprised from 0 to 8.

In an advantageous embodiment, the present Invention relates to a composition for its use as a drug in the prevention or the treatment of infections caused by *Aspergillus* spp comprising a compound as defined above as active ingredient.

In an advantageous embodiment, the present Invention relates to a composition for its use comprising a compound as defined above as active ingredient, formulated for its human and/or animal use.

In another advantageous embodiment, the present Invention relates to a composition for its use comprising a compound of formula (I) as active ingredient, formulated for its human and/or animal use.

In an advantageous embodiment, the present Invention relates to a composition for its use comprising a compound as defined above as active ingredient, said *Aspergillus* spp being *Aspergillus* section *Fumigati*, *Aspergillus* section *Flavi*, *Aspergillus* section *Nigri*, *Aspergillus* section *Nidulantes*, *Aspergillus oryzae*, *Aspergillus bombycis*, *Aspergillus nemius*.

In particular, the present Invention relates to a composition for its use comprising a compound as defined above as active ingredient, said *Aspergillus* spp being *Aspergillus* section *Fumigati*, *Aspergillus* section *Flavi*, *Aspergillus* section *Nigri*, *Aspergillus* section *Nidulantes*, more particularly said *Aspergillus* spp being *Aspergillus* section *Fumigati*.

In another advantageous embodiment, the present Invention relates to a composition for its use comprising a compound of formula (I) as active ingredient, said *Aspergillus* spp being *Aspergillus* section *Fumigati*, *Aspergillus* section *Flavi*, *Aspergillus* section *Nigri*, *Aspergillus* section *Nidulantes*, *Aspergillus oryzae*, *Aspergillus bombycis*, *Aspergillus nemius*.

In particular, the present Invention relates to a composition for its use comprising a compound of formula (I) as active ingredient, said *Aspergillus* spp being *Aspergillus* section *Fumigati*, *Aspergillus* section *Flavi*, *Aspergillus* section *Nigri*, *Aspergillus* section *Nidulantes*, more particularly said *Aspergillus* spp being *Aspergillus* section *Fumigati*.

In an advantageous embodiment, the present Invention relates to a composition for its use comprising a compound as defined above as active ingredient, said infection being an aspergillosis, in particular an allergic broncho-pulmonary aspergillosis, an aspergilloma, a chronic pulmonary aspergillosis or an invasive pulmonary aspergillosis.

In another advantageous embodiment, the present Invention relates to a composition for its use comprising a compound of formula (I) as active ingredient, said infection being an aspergillosis, in particular an allergic broncho-pulmonary aspergillosis, an aspergilloma, a chronic pulmonary aspergillosis or an invasive pulmonary aspergillosis.

Aspergillosis is a group of diseases which can result from *Aspergillus* infection and includes invasive aspergillosis, allergic broncho-pulmonary aspergillosis, chronic pulmonary aspergillosis and aspergilloma. Asthma is also complicated and exacerbated by *Aspergillus* infection (SAFS). *Aspergillus* affects humans and birds and animals can also develop aspergillosis, commercially many plant diseases and food spoilage may be due to *Aspergillus* infection or contamination.

In an advantageous embodiment, the present Invention relates to a composition for its use comprising a compound as defined above as active ingredient, said compound being used by respiratory route, in particular by inhalation, by oral route or intravenously.

In another advantageous embodiment, the present Invention relates to a composition for its use comprising a compound of formula (I) as active ingredient, said compound of formula (I) being used by respiratory route, in particular by inhalation, by oral route or intravenously.

Inhalable preparations comprising a compound of the Invention include inhalable powders, propellant-containing metered dose aerosols or propellant-free inhalable solutions. Inhalable powders according to the invention containing the active substance may consist of the active substance on its own or of a mixture of the active substance with physiologically acceptable excipients. Within the scope of the present invention, the term "propellant-free inhalable solutions" also includes concentrates or sterile inhalable solutions ready for use.

Inhalable Powders:

if the active substance of the Invention is present in a mixture with physiologically acceptable excipients, the following physiologically acceptable excipients may be used to prepare the inhalable powders according to the invention: monosaccharides (e.g. glucose or arabinose), disaccharides (e.g. lactose, saccharose, maltose), oligo- and polysaccharides (e.g. dextran), polyalcohols (e.g. sorbitol, mannitol, xylitol), salts (e.g. sodium chloride, calcium carbonate) or mixtures of these excipients with one another. Preferably, mono- or disaccharides are used, while the use of lactose or glucose is preferred, particularly, but not exclusively, in the form of their hydrates.

Propellant-Containing Inhalable Aerosols:

the propellant-containing inhalable aerosols which may be used according to the invention may contain a compound of the Invention dissolved in the propellant gas or in dispersed form. The propellant gases which may be used to prepare the inhalation aerosols according to the invention are known from the prior art. Suitable propellant gases are selected from among hydrocarbons such as n-propane, n-butane or isobutane and halohydrocarbons such as preferably fluorinated derivatives of methane, ethane, propane, butane, cyclopropane or cyclobutane. The propellant gases mentioned above may be used on their own or in mixtures thereof. Particularly preferred propellant gases are fluorinated alkane derivatives selected from TG134a (1,1,1,2-tetrafluoroethane), TG227 (1,1,1,2,3,3,3-heptafluoropropane) and mixtures thereof. The propellant-driven inhalation aerosols used within the scope of the use according to the invention may also contain other ingredients such as co-solvents, stabilisers, surfactants, antioxidants, lubricants and pH adjusters. All these ingredients are known in the art.

Propellant Free Inhalable Solutions:

the compounds of the Invention are, in particular, used to prepare propellant-free inhalable solutions and inhalable suspensions. Solvents used for this purpose include aqueous or alcoholic, preferably ethanolic solutions. The solvent may be water on its own or a mixture of water and ethanol. The solutions or suspensions are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. It is also possible to use the acids which have already formed an acid addition salt with one of the active substances. Of the organic acids, ascorbic acid, fumaric acid and citric acid are preferred. If desired, mixtures of the above acids may also be used, particularly in the case of acids which have other properties in addition to their acidifying qualities, e.g. as flavorings, antioxidants or complexing agents, such as citric acid or ascorbic acid, for example.

Co-solvents and/or other excipients may be added to the propellant-free inhalable solutions used for the purpose according to the invention. Preferred co-solvents are those which contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters.

The terms "excipients" and "additives" in this context denote any pharmacologically acceptable substance which is not an active substance but which can be formulated with the active substance or substances in the pharmacologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilisers, complexing agents, antioxidants and/or preservatives which guarantee or prolong the shelf life of the finished pharmaceutical formulation, flavorings, vitamins and/or other additives known in the art. The additives also include pharmacologically acceptable salts such as sodium chloride as isotonic agents. The preferred excipients include antioxidants such as ascorbic acid, for example, provided that it has not already been used to adjust the pH, vitamin A, vitamin E, tocopherols and similar vitamins or provitamins occurring in the human body. Preservatives may be used to protect the formulation from contamination with pathogens. Suitable preservatives are those which are known in the art, particularly acetyl pyridinium chloride, benzalkonium chloride or benzoic acid or benzoates such as sodium benzoate in the concentration known from the prior art.

The compositions of the invention can also be in the form of sterile powders, granules, tablets, concentrated solutions or suspensions, or freeze-dried powders reconstituted with sterile water or saline.

Extemporaneous injection solutions and suspensions can be prepared from these sterile powders, granules, tablets, concentrated solutions or suspensions, or freeze-dried powders reconstituted with sterile water or saline before administration to the subject.

The suitable formulations for the desired administration route are known from the man skilled in the art and described, for example in: Remington, The science and Practice of Pharmacy, 22$^{ème}$ édition, 2013, The Pharmaceutical Press.

In an advantageous embodiment, the present Invention relates to a composition for its use comprising a compound as defined above as active ingredient, said composition comprising from 1 mg to 1.4 g of active ingredient; in particular from 1 to 7 mg of active ingredient, or from 7 to 700 mg of active ingredient, or from 70 to 350 mg of active ingredient, or from 350 to 700 mg of active ingredient, or from 700 mg to 1.05 g of active ingredient, or from 1.05 to 1.4 g of active ingredient.

According to the present Invention, a dosage from 1 mg to 1.4 g of active ingredient, in particular from 1 to 7 mg of active ingredient, or from 7 to 700 mg of active ingredient, or from 70 to 350 mg of active ingredient, or from 350 to 700 mg of active ingredient, or from 700 mg to 1.05 g of active ingredient, or from 1.05 to 1.4 g of active ingredient, corresponds to a daily intake by nebulization to a human body.

In another advantageous embodiment, the present Invention relates to a composition for its use comprising a compound of formula (I) as active ingredient, said composition comprising from 1 mg to 1.4 g of active ingredient; in particular from 1 to 7 mg of active ingredient, or from 7 to 700 mg of active ingredient, or from 70 to 350 mg of active ingredient, or from 350 to 700 mg of active ingredient, or from 700 mg to 1.05 g of active ingredient, or from 1.05 to 1.4 g of active ingredient.

In an advantageous embodiment, the present Invention relates to a composition for its use comprising a compound as defined above as active ingredient, said composition comprising from 200 mg to 10 g of active ingredient; in particular from 400 mg to 7 g of active ingredient.

According to the present Invention, a dosage from 200 mg to 10 g of active ingredient, in particular from 400 mg to 7 g of active ingredient, corresponds to a daily intake by oral route to a human body.

In another advantageous embodiment, the present Invention relates to a composition for its use comprising a compound of formula (I) as active ingredient, said composition comprising from 200 mg to 10 g of active ingredient; in particular from 400 mg to 7 g of active ingredient.

In an advantageous embodiment, the present Invention relates to a composition for its use comprising a compound as defined above as active ingredient, said composition comprising from 10 mg to 10 g of active ingredient; in particular from 50 mg to 7 g of active ingredient. According to the present Invention, a dosage from 10 mg to 10 g of active ingredient, in particular from 50 mg to 7 g of active ingredient, corresponds to a daily intravenous intake to a human body.

In another advantageous embodiment, the present Invention relates to a composition for its use comprising a compound of formula (I) as active ingredient, said composition comprising from 10 mg to 10 g of active ingredient; in particular from 50 mg to 7 g of active ingredient.

In an advantageous embodiment, the present Invention relates to a composition for its use comprising a compound as defined above as active ingredient, said composition comprising from 0.015 to 20 mg/kg of active ingredient; in particular from 0.015 to 0.1 mg/kg of active ingredient, or from 0.1 to 10 mg/kg of active ingredient, or from 1 to 5 mg/kg of active ingredient, or from 5 to 10 mg/kg of active ingredient, or from 10 to 15 mg/kg of active ingredient, or from 15 to 20 mg/kg of active ingredient.

According to the present Invention, a dosage from 0.015 to 20 mg/kg of active ingredient, in particular from 0.015 to 0.1 mg/kg of active ingredient, or from 0.1 to 10 mg/kg of active ingredient, or from 1 to 5 mg/kg of active ingredient, or from 5 to 10 mg/kg of active ingredient, or from 10 to 15 mg/kg of active ingredient, or from 15 to 20 mg/kg of active ingredient, corresponds to a daily intake by nebulization to a human body of 70 kg.

In another advantageous embodiment, the present Invention relates to a composition for its use comprising a compound of formula (I) as active ingredient, said composition comprising from 0.015 to 20 mg/kg of active ingredient; in particular from 0.015 to 0.1 mg/kg of active ingredient, or from 0.1 to 10 mg/kg of active ingredient, or from 1 to 5 mg/kg of active ingredient, or from 5 to 10 mg/kg of active ingredient, or from 10 to 15 mg/kg of active ingredient, or from 15 to 20 mg/kg of active ingredient.

In an advantageous embodiment, the present Invention relates to a composition for its use comprising a compound as defined above as active ingredient, said composition comprising from 3 mg/kg to 143 mg/kg of active ingredient; in particular from 6 mg/kg to 100 mg/kg of active ingredient.

According to the present Invention, a dosage from 3 mg/kg to 143 mg/kg of active ingredient, in particular from 6 mg/kg to 100 mg/kg of active ingredient, corresponds to a daily intake by oral route to a human body of 70 kg.

In another advantageous embodiment, the present Invention relates to a composition for its use comprising a compound of formula (I) as active ingredient, said composition comprising from 3 mg/kg to 143 mg/kg of active ingredient; in particular from 6 mg/kg to 100 mg/kg of active ingredient.

In an advantageous embodiment, the present Invention relates to a composition for its use comprising a compound as defined above as active ingredient, said composition comprising from 0.15 mg/kg to 143 mg/kg of active ingredient; in particular from 1 mg/kg to 100 mg/kg of active ingredient.

According to the present Invention, a dosage from 0.15 mg/kg to 143 mg/kg of active ingredient, in particular from 1 mg/kg to 100 mg/kg of active ingredient, corresponds to a daily intravenous intake to a human body of 70 kg.

In another advantageous embodiment, the present Invention relates to a composition for its use comprising a compound of formula (I) as active ingredient, said composition comprising from 0.15 mg/kg to 143 mg/kg of active ingredient; in particular from 1 mg/kg to 100 mg/kg of active ingredient.

In an advantageous embodiment, the present Invention relates to a composition for its use comprising a compound as defined above as active ingredient, said compound being in association with an antifungal agent such as an azole antifungal agent, a polyene antifungal agent or an echinocandin antifungal agent.

In another advantageous embodiment, the present Invention relates to a composition for its use comprising a compound of formula (I) as active ingredient, said compound being in association with an antifungal agent such as an azole antifungal agent, a polyene antifungal agent or an echinocandin antifungal agent.

The present Invention also relates to a method for the prevention or the treatment of infections caused by *Aspergillus* spp comprising a step of administering a compound as defined above.

In an advantageous embodiment, the present Invention relates to a method for the prevention or the treatment of infections caused by *Aspergillus* spp comprising a step of administering a compound of formula (I) as defined above.

The present Invention also relates to a compound bearing at least two fucose moieties and having a molecular weight comprised from 0.6 to 340 kDa, in particular from 0.6 to 2 kDa or from 1 to 7 kDa or from 2 to 10 kDa or from 5 to 340 kDa.

In particular, the molecular weight of the compound is from 0.6 to 2 kDa which includes a molecular weight of 0.6, 0.7, 0.8, 0.9, 1.0, 1.1, 1.2, 1.3, 1.4, 1.5, 1.6, 1.7, 1.8, 1.9 and 2.

In particular, the molecular weight of the compound is from 1 to 7 kDa which includes a molecular weight of 1, 1.5, 2, 2.5, 3, 3.5, 4, 4.5, 5, 5.5, 6, 6.5 and 7 kDa.

In particular, the molecular weight of the compound is from 2 to 10 kDa which includes a molecular weight of 2, 2.5, 3, 3.5, 4, 4.5, 5, 5.5, 6, 6.5, 7, 7.5, 8, 8.5, 9, 9.5 and 10 kDa.

In particular, the molecular weight of the compound is from 5 to 340 kDa which includes a molecular weight of 5, 10, 15, 20, 25, 30, 40, 50, 60, 70, 80, 90, 100, 125, 150, 175, 200, 225, 250, 275, 300, 325 and 340 kDa.

In an advantageous embodiment, the present Invention relates to a compound, said compound being of formula (I)

wherein i is equal to 0 or 1;

A is selected from

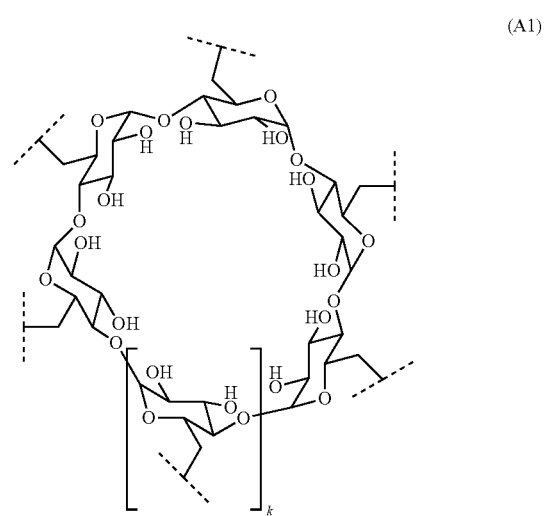

k being equal to 1, 2, or 3: k being in particular equal to 1;

r being comprised from 1 to 30, in particular from 1 to 4, from 5 to 9, from 10 to 15, from 16 to 20, from 21 to 25 or from 26 to 30;

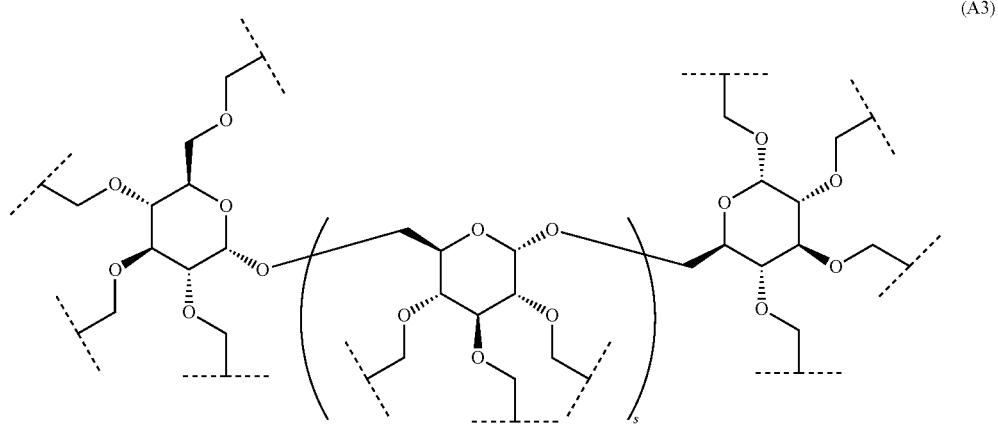

s being comprised from 5 to 300; in particular from 60 to 80;
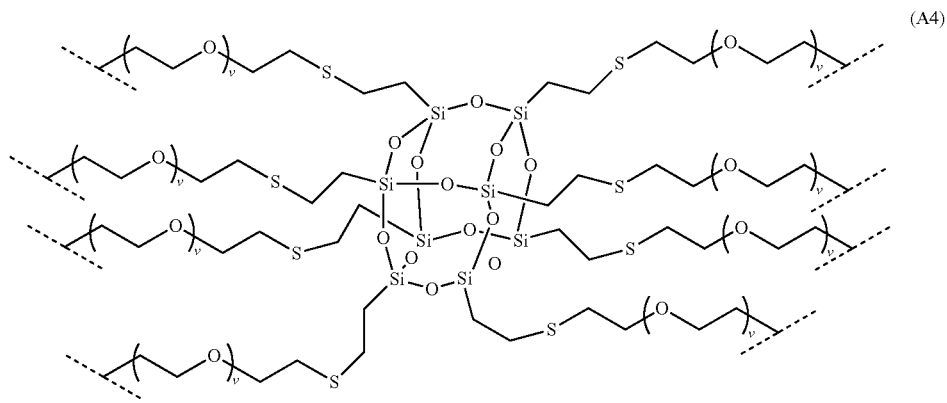
v being comprised from 0 to 10; in particular from 1 to 8; preferably v being equal to 3;
B is of formula
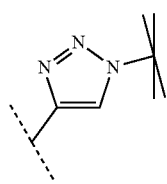
C is of formula
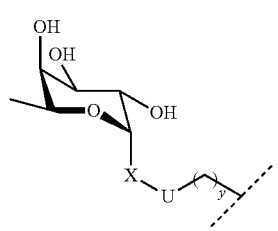
y being equal to 0 or 1;
X being selected from O, S or $CH_2$;
U being selected from
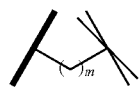
m being comprised from 0 to 8,
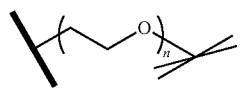
n being comprised from 0 to 8,
p being comprised from 1 to 10,
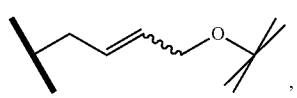
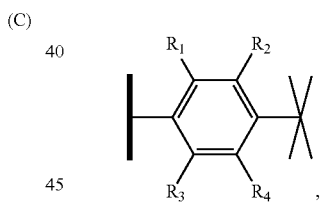
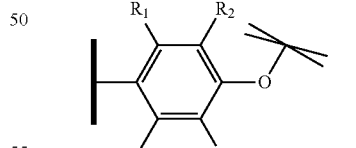
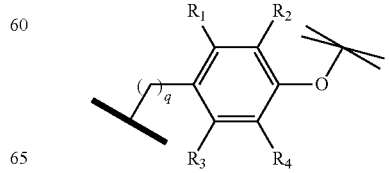

q being comprised from 1 to 10,

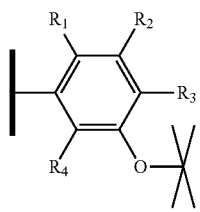

or

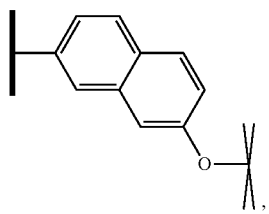

$R_1$, $R_2$, $R_3$ and $R_4$ being independently from each other selected from H, $COCH_3$, $NH_2$, $NO_2$, NHAc, OH, OMe, COOH, COOMe, CONHMe, Cl, Br, I, F, SMe or Me;

provided that y+n or y+m is different from 0;
in particular, m being comprised from 1 to 5;
in particular, n being comprised from 0 to 5;
D being selected from

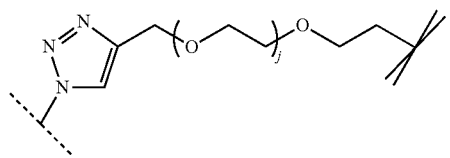

j being comprised from 0 to 8.

In a particular embodiment, the present invention relates to a compound bearing at least two fucose moieties and having a molecular weight comprised from 0.6 to 340 kDa, in particular from 0.6 to 2 kDa or from 1 to 7 kDa or from 2 to 10 kDa or from 5 to 340 kDa.

said compound being of formula (I)

$$A\text{-}(D)_i\text{-}B\text{—}C \qquad (I)$$

wherein
i is equal to 0 or 1;
A is selected from

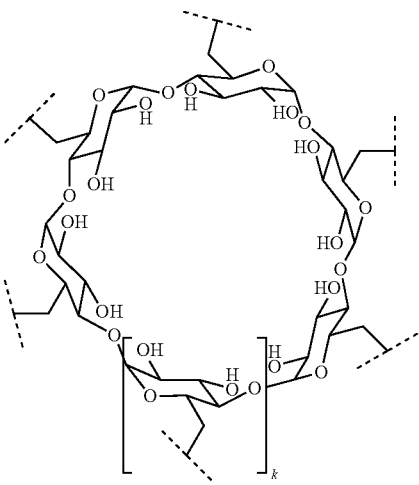

(A1)

k being equal to 1, 2, or 3; k being in particular equal to 1;

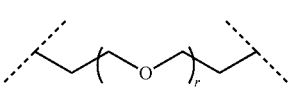

(A2)

r being comprised from 1 to 30, in particular from 1 to 4, from 5 to 9, from 10 to 15, from 16 to 20, from 21 to 25 or from 26 to 30;

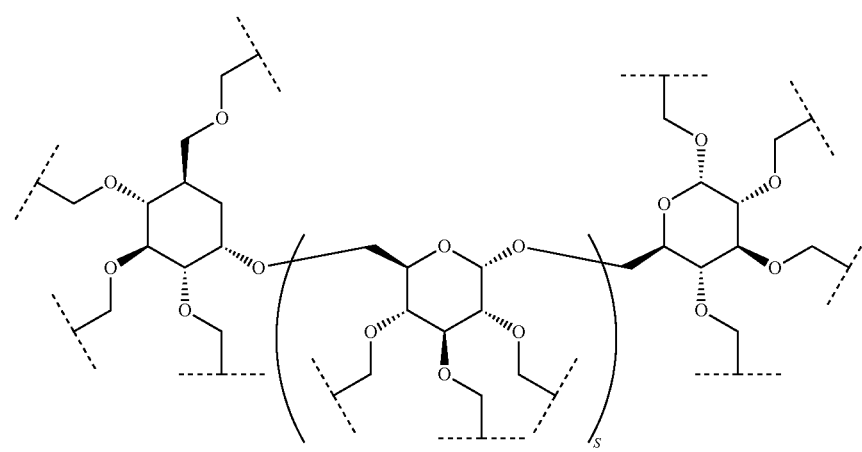

(A3)

s being comprised from 5 to 300; in particular from 60 to 80;
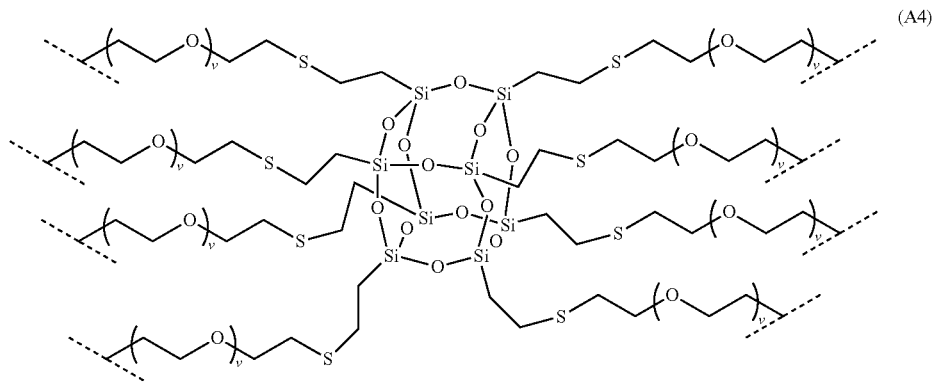
(A4)
v being comprised from 0 to 10; in particular from 1 to 8; preferably v being equal to 3;
B is of formula
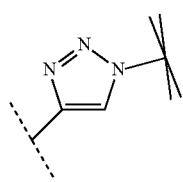
(B)
C is of formula
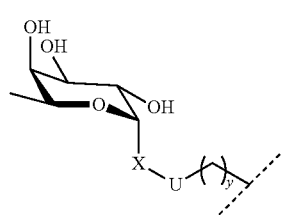
(C)
y being equal to 0 or 1;
X being selected from O, S or CH$_2$;
U being selected from
m being comprised from 0 to 8,
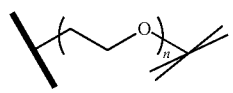
n being comprised from 0 to 8,
p being comprised from 1 to 10,
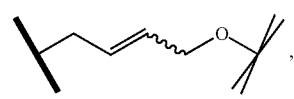
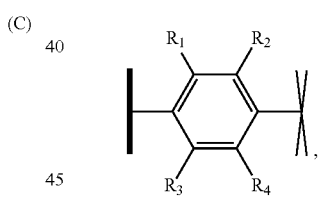
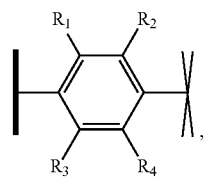
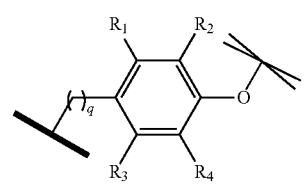

q being comprised from 1 to 10,

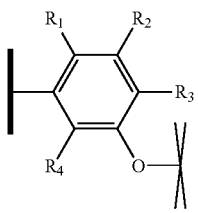

or

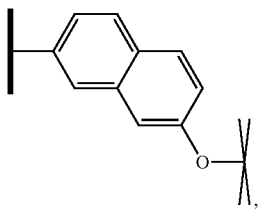

$R_1$, $R_2$, $R_3$ and $R_4$ being independently from each other selected from H, $COCH_3$, $NH_2$, $NO_2$, NHAc, OH, OMe, COOH, COOMe, CONHMe, Cl, Br, I, F, SMe or Me;

provided that y+n or y+m is different from 0;
in particular, m being comprised from 1 to 5;
in particular, n being comprised from 0 to 5;
D being selected from

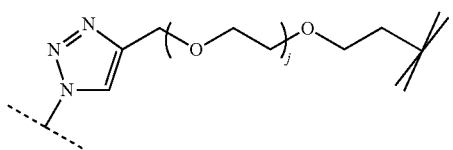

j being comprised from 0 to 8.

In an advantageous embodiment, the present Invention relates to a compound of formula (I)

$$A\text{-}(D)_i\text{-}B\text{—}C \qquad (I)$$

wherein
i is equal to 0 or 1;
A is selected from

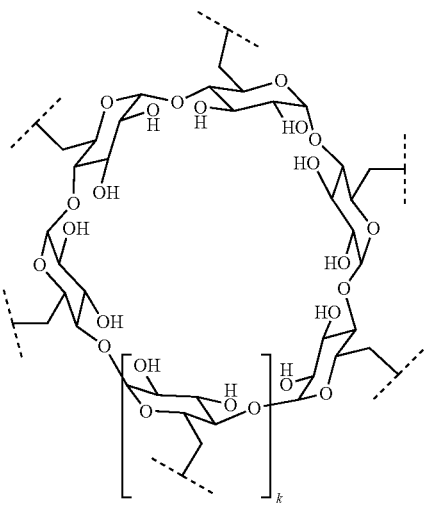
(A1)

k being equal to 1, 2, or 3; k being in particular equal to 1;

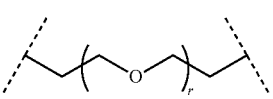
(A2)

r being comprised from 1 to 30, in particular from 1 to 4, from 5 to 9, from 10 to 15, from 16 to 20, from 21 to 25 or from 26 to 30;

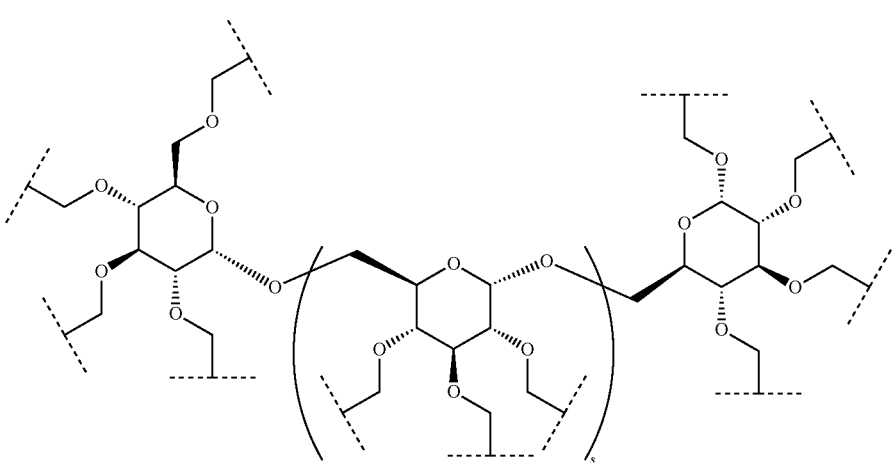
(A3)

s being comprised from 5 to 300; in particular from 60 to 80;

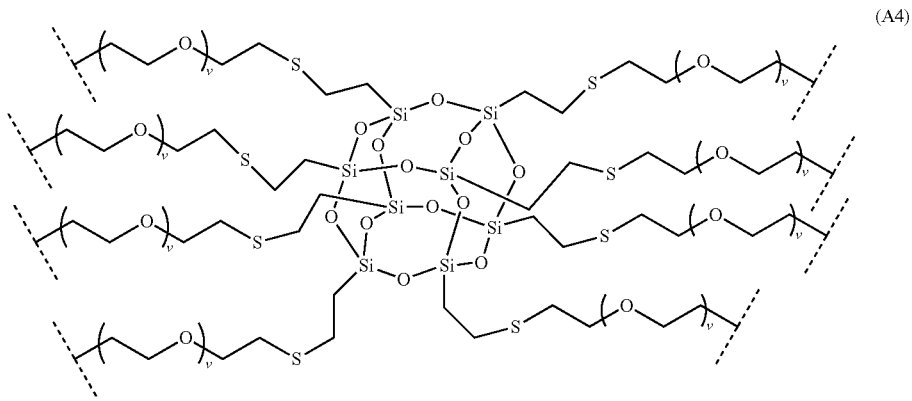

(A4)

v being comprised from 0 to 10; in particular from 1 to 8; preferably v being equal to 3;

B is of formula

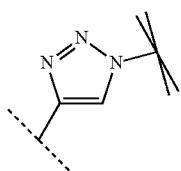

(B)

C is of formula

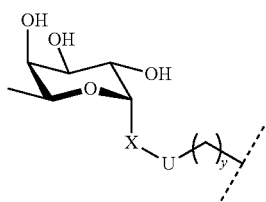

(C)

y being equal to 1;

X being selected from O, S or $CH_2$;

U being selected from

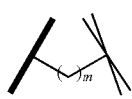

m being comprised from 0 to 8,

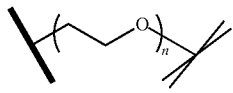

n being comprised from 0 to 8, or

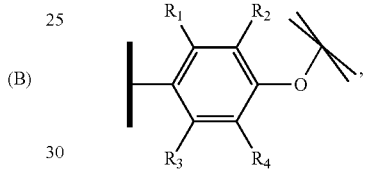

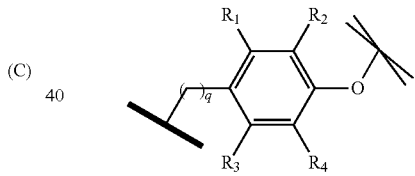

q being comprised from 1 to 10, $R_1$, $R_2$, $R_3$ and $R_4$ being independently from each other selected from H, $COCH_3$, $NH_2$, $NO_2$, NHAc, OH, OMe, COOH, COOMe, CONHMe, Cl, Br, I, F, SMe or Me;

in particular, m being comprised from 1 to 5;

in particular, n being comprised from 0 to 5;

D being selected from

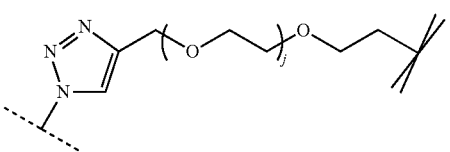

j being comprised from 0 to 8.

In another advantageous embodiment, the present Invention relates to a compound of formula (I-A1), A being of formula A1, in particular selected from (A1-1)

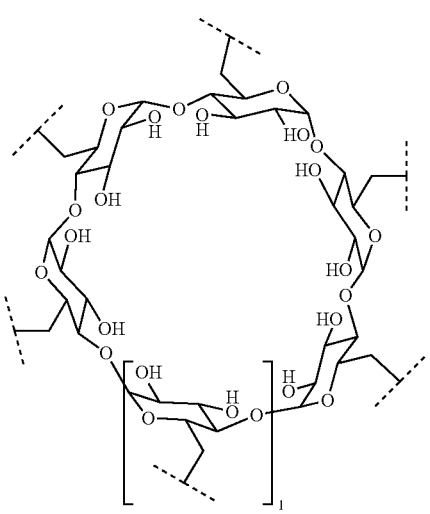

k being equal to 1;

$D_i$, B and C being as defined in formula (I).

In another advantageous embodiment, the present Invention relates to a compound of formula (I-A2), A being of formula A2, in particular selected from (A2-1)
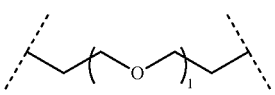

r being equal to 1;

(A2-2)
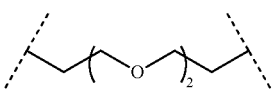

r being equal to 2;

(A2-3)

r being equal to 3;

(A2-4)
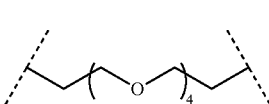

r being equal to 4;

(A2-5)
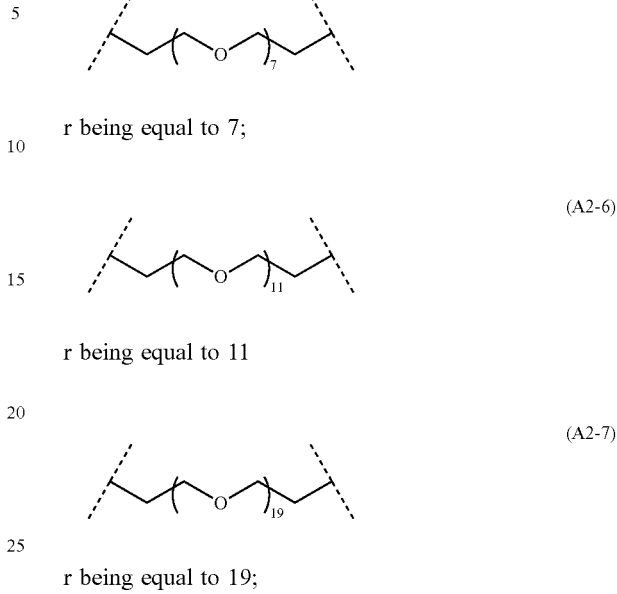

r being equal to 7;

(A2-6)

r being equal to 11

(A2-7)

r being equal to 19;

(A2-8)

r being equal to 27

$D_i$, B and C being as defined in formula (I).

In another advantageous embodiment, the present Invention relates to a compound of formula (I-A3), A being of formula A3, in particular selected from (A3-1)
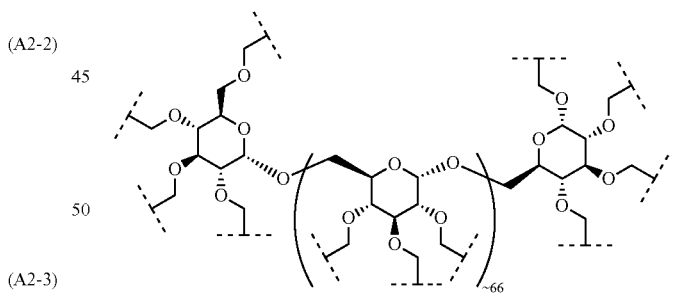

s being equal to ~66;

$D_i$, B and C being as defined in formula (I).

The dextran scaffold (A3) is a polymer scaffold. This polymer being polydisperse, the amount of glucose monomer units in the scaffold cannot be exactly defined. In particular, the dextran scaffolds according to the Invention have a polydispersity index, PDI, inferior of 1.50. Therefore, the A group of formula (A3-1) has an approximate number of 68 glucose units (s equal to ~66); "an approximate number of 68 glucose units" referring to a PDI of 1.43.

In another advantageous embodiment, the present Invention relates to a compound of formula (I-A4), A being of formula A4, in particular selected from

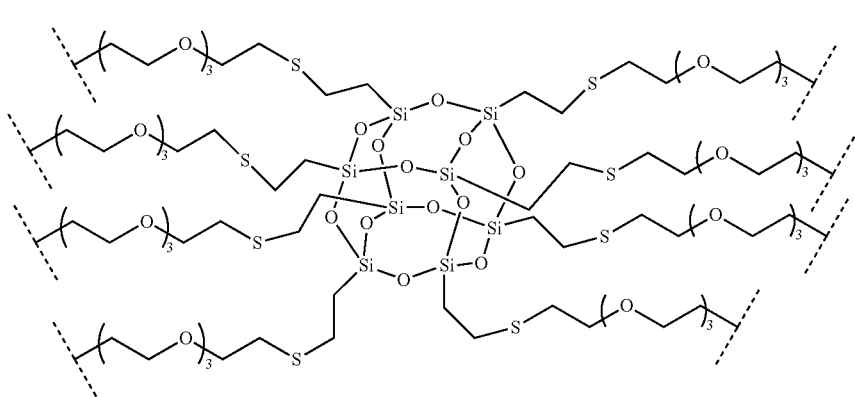

(A4-1)

$D_i$, B and C being as defined in formula (I).

In another advantageous embodiment, the present Invention relates to a compound of formula (I-B), B being selected from B1 or B2

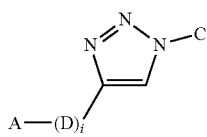

(B1)

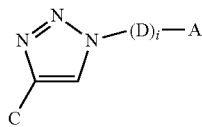

(B2)

A, $D_i$ and C being as defined in formula (I).

In another advantageous embodiment, the present Invention relates to a compound of formula (I-C), C being selected from C1, C2 or C3

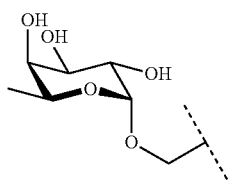

(C1)

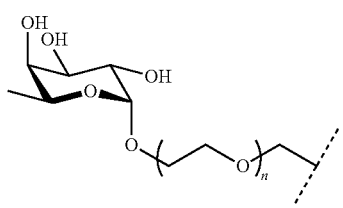

(C2)

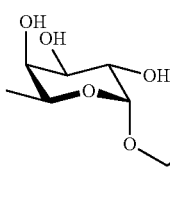

(C3)

A, B and $D_i$ being as defined in formula (I).

In formula C1, X is an oxygen atom, m and n are equal to 0.

In formula C2, X is an oxygen atom, m is equal to 0 and n is comprised from 0 to 8.

In formula C3, X is an oxygen atom, m is equal to 1 and n is equal to 0.

In another advantageous embodiment, the present Invention relates to a compound of formula (I-C2), C being selected from

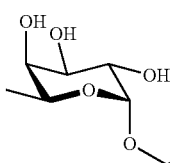

(C2-1)

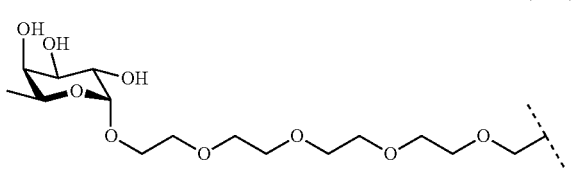

(C2-2)

A, B and $D_i$ being as defined in formula (I).

In (C2-1), the X group is an O, m is equal to 0 and n is equal to 2. In (C2-2), the X group is an O, m is equal to 0 and n is equal to 4.

In another advantageous embodiment, the present Invention relates to a compound of formula (I-BC), said compound comprising the groups

[B2-C1],

[B2-C2],

[B2-C2-1],
[B2-C2-2], or
[B1-C3];
A being as defined in formula (I).

In another advantageous embodiment, the present Invention relates to a compound of formula (I), said compound being selected from
[A1-B2-C1],
[A1-B2-C2],
[A1-B2-C2-1],
[A1-B2-C2-2]
[A1-1-B2-C1],
[A1-1-B2-C2],
[A1-1-B2-C2-1], or
[A1-1-B2-C2-2]

According to the Invention, the compound of formula [A1-1-B2-C2-1] represents

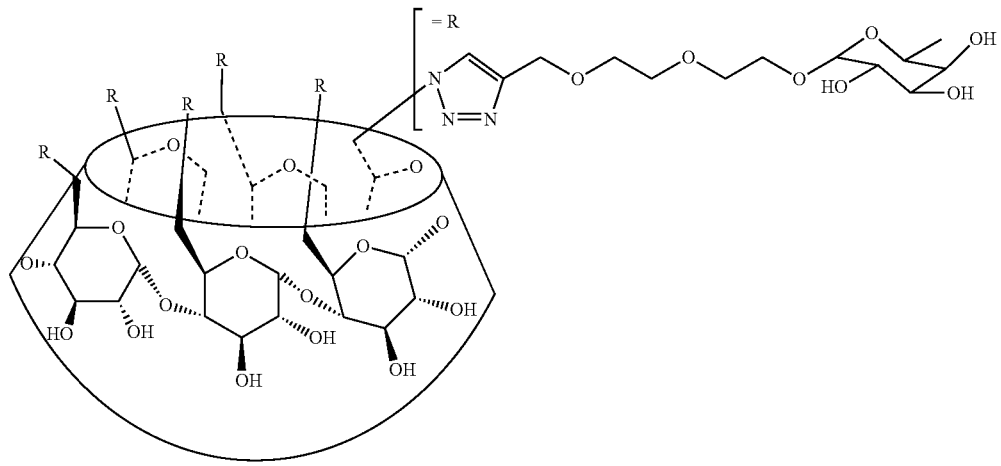

The Inventors have found that α-cyclodextrine derivatives (a cyclodextrine having six glucose units) of the Invention, bearing six fucose moieties, have a particularly strong affinity for an *Aspergillus* lectin associated with a particularly strong anti-adhesive property to this lectin. According to an aspect of the Invention, the α-cyclodextrine derivatives of the Invention have a particularly strong affinity for, associated with a particularly strong anti-adhesive property to, the AFL lectin.

The affinity to the *Aspergillus* lectin AFL is, for example, measured by the Isothermal titration calorimetry (ITC) method described in Example 35. Isothermal titration calorimetry is a method often used to measure the thermodynamic constants of the interaction between a biomolecule and a synthetic compound. It is the only technique to measure both the enthalpic and entropic parameters of binding, without modification of the partners involved. This method is based on the estimation of the release of heat upon formation of the compound-receptor linkage in a microcalorimeter having two cells. One contains ultra-pure water maintained at a precise temperature and serves as a reference cell; the other contains a protein solution at a fixed concentration (FIG. 1-I). To this solution, the apparatus adds a precise volume of a compound solution at regular intervals of time, with stirring. This injection then generates a variation of heat with respect to the reference cell which is compensated by a heating resistor. The power needed to maintain the temperature is then recorded for all compound injections. The integration of the raw data in the form of a graph (FIGS. 1-II and 1-III) gives access to the dissociation constant Kd, to the stoichiometric data and enthalpy data (ΔH) of bonding. From this data it is then possible to determine the free enthalpy (ΔG) and the entropy variation of the system (ΔS). The dissociation constant obtained from the equilibrium slope indicates the compound-protein thermodynamic affinity, while the energy difference between the lower plate and the upper plate gives the enthalpy value. This demonstrates the contribution of hydrogen bonds and Van der Waals energies to the bond formed. The values of free enthalpy and entropy can be deduced from the first data acquired thanks to the equations of thermodynamics. Entropy gives us the part of the conformational aspects like the loss of degrees of freedom.

The anti-adhesive property is, for example, measured according to the method described in Example 36. The anti-adhesive strategy is based on the inhibition of the conidia adhesion at the surface of the broncho-pulmonary epithelium. These spores present a particularly high adhesion potential on alveolar pneumocytes forming the epithelium. The first step aims at obtaining an alveolar pneumocytes layer in a 96 wells plate. Therefore approximately 40 000 cells are introduced in each well and are incubated for 7 days at 37° C. During this incubation time, the cells will deposit at the bottom of the wells in a homogeneous manner to reach a confluence and leave no empty space between the cells which come into contact with each other. In parallel, *Aspergillus fumigatus* is grown at 37° C. for 3 to 5 days. The spores are then carefully harvested in a PBS buffer solution while avoiding taking those which have evolved into filaments (hyphae). This solution is diluted to a concentration of 1 to $2 \times 10^6$ spores/mL and then preincubated with the various fucoside derivatives of the Invention in variable concentration. This step allows the fucoside derivatives of the Invention to interact beforehand with the lectin AFL on *Aspergillus fumigatus*. Each of these solutions is then added to a well containing the layer of pneumocytes and then incubated at 37° C. for 45 minutes. The compounds having a large anti-adhesive potential will reduce the spore binding ability. Thus, after incubation, the spores present in the supernatant are eliminated by three rinsing steps. The spores adhered to the cellular layer are then counted under a microscope on an average surface of 400 pneumocytes. This method is schematized on FIG. 3.

In another advantageous embodiment, the present Invention relates to a compound of formula (I), said compound being selected from
[A2-B2-C1],
[A2-4-B2-C1],
[A2-5-B2-C1],
[A2-6-B2-C1],
[A2-7-B2-C1],
[A2-8-B2-C1],
[A4-B2-C1],
[A4-B2-C2],
[A4-B2-C2-1]
[A4-B2-C2-2],
[A4-1-B2-C1],
[A4-1-B2-C2],
[A4-1-B2-C2-1],
[A4-1-B2-C2-2],
[A3-B1-C3], or
[A3-1-B1-C3],
or said compound being selected from The present Invention also relates to a compound bearing at least two fucose moieties for its use as a drug, said compound having a molecular weight comprised from 0.6 to 340 kDa, in particular from 0.6 to 2 kDa or from 1 to 7 kDa or from 2 to 10 kDa or from 5 to 340 kDa.

In particular, the molecular weight of the compound is from 0.6 to 2 kDa which includes a molecular weight of 0.6, 0.7, 0.8, 0.9, 1.0, 1.1, 1.2, 1.3, 1.4, 1.5, 1.6, 1.7, 1.8, 1.9 and 2.

In particular, the molecular weight of the compound is from 1 to 7 kDa which includes a molecular weight of 1, 1.5, 2, 2.5, 3, 3.5, 4, 4.5, 5, 5.5, 6, 6.5 and 7 kDa.

In particular, the molecular weight of the compound is from 2 to 10 kDa which includes a molecular weight of 2, 2.5, 3, 3.5, 4, 4.5, 5, 5.5, 6, 6.5, 7, 7.5, 8, 8.5, 9, 9.5 and 10 kDa.

In particular, the molecular weight of the compound is from 5 to 340 kDa which includes a molecular weight of 5, 10, 15, 20, 25, 30, 40, 50, 60, 70, 80, 90, 100, 125, 150, 175, 200, 225, 250, 275, 300, 325 and 340 kDa.

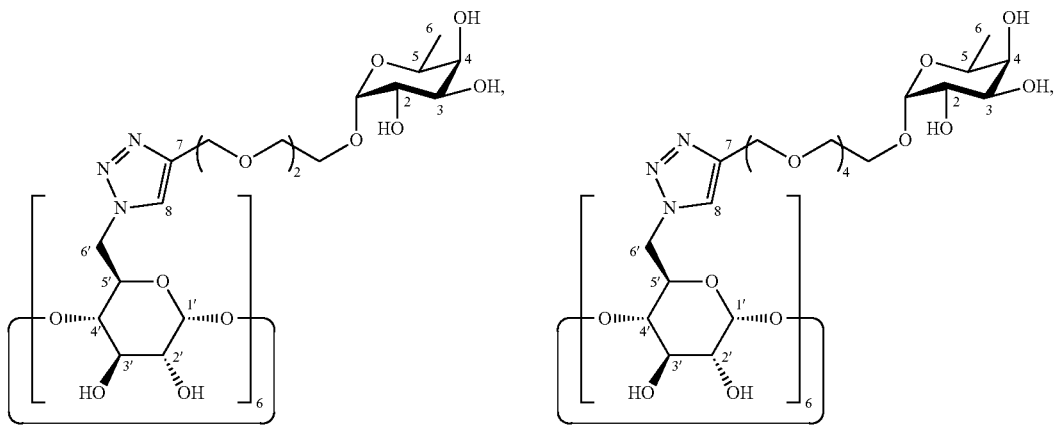

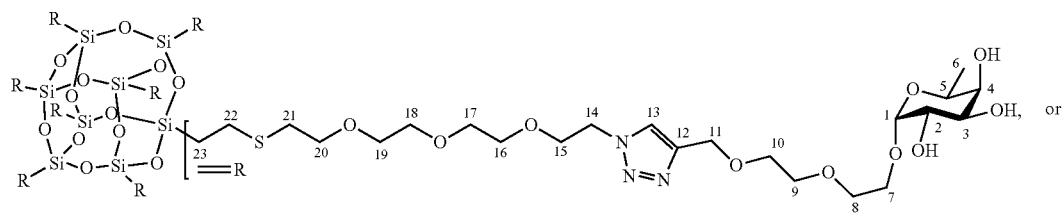

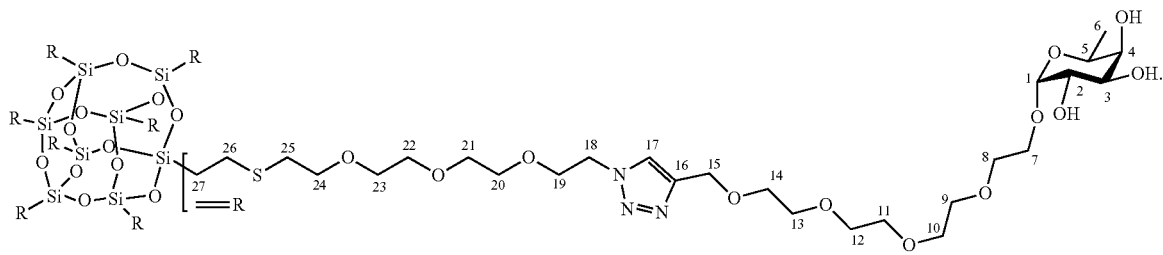

In an advantageous embodiment, the present Invention relates to a compound for its use, said compound being of formula (I)
A-(D)$_i$-B—C                     (I)
wherein
i is equal to 0 or 1;
A is selected from
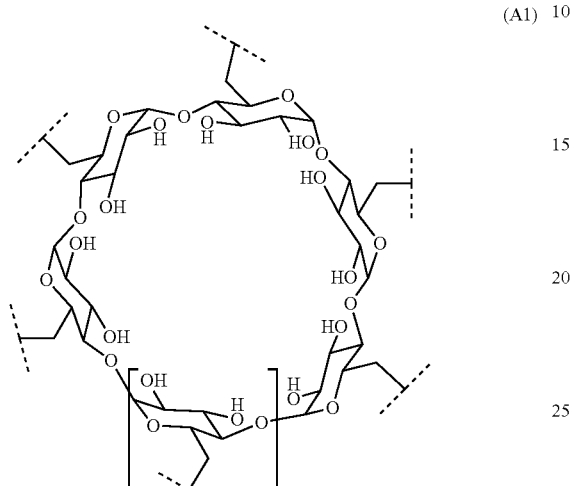
(A1)
k being equal to 1, 2, or 3; k being in particular equal to 1;
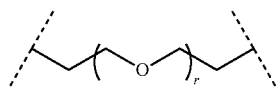
(A2)
r being comprised from 1 to 30, in particular from 1 to 4, from 5 to 9, from 10 to 15, from 16 to 20, from 21 to 25 or from 26 to 30;
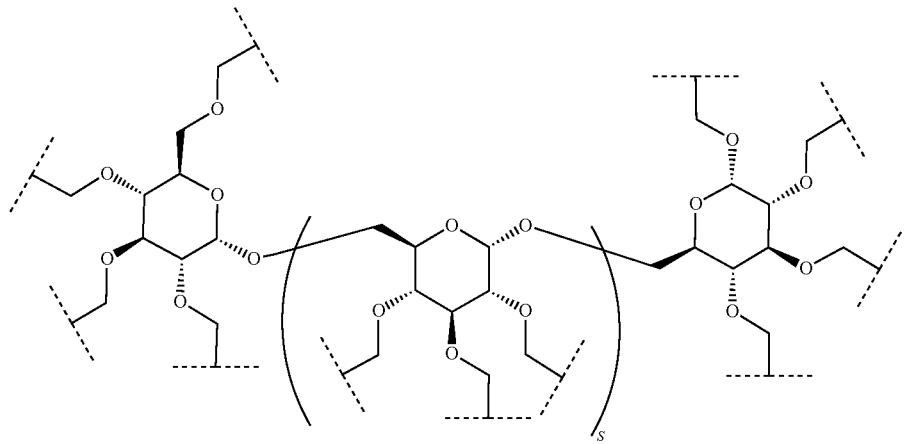
(A3)
s being comprised from 5 to 300; in particular from 60 to 80;

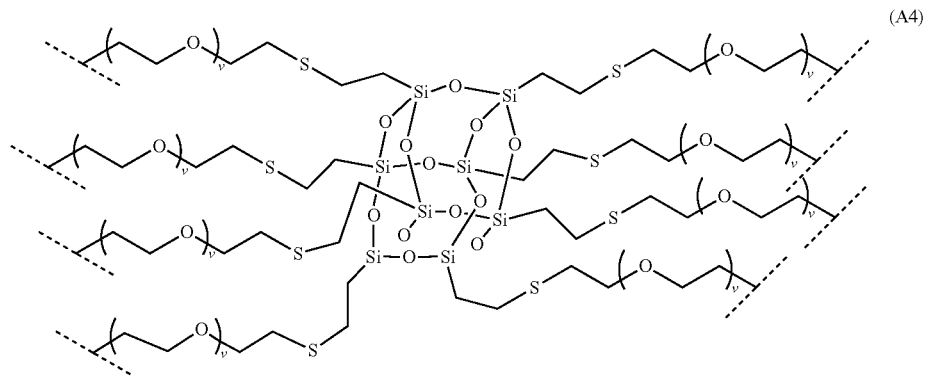
v being comprised from 0 to 10; in particular from 1 to 8; preferably v being equal to 3;
B is of formula
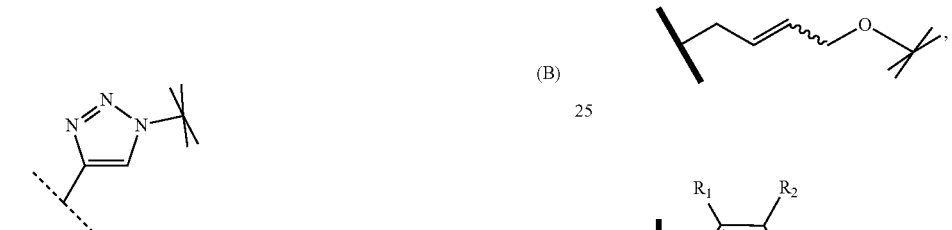
C is of formula
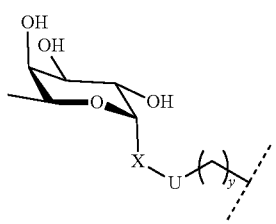
y being equal to 0 or 1;
X being selected from O, S or $CH_2$;
U being selected from
m being comprised from 0 to 8,
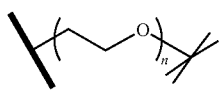
n being comprised from 0 to 8,
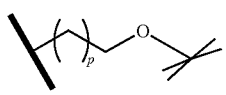
p being comprised from 1 to 10,
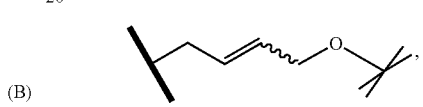
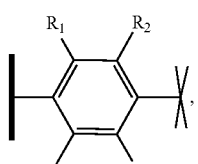
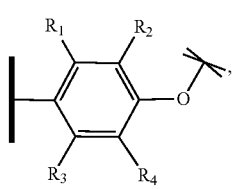
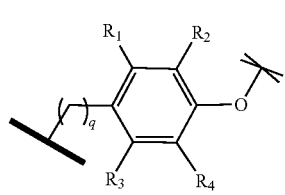
q being comprised from 1 to 10,
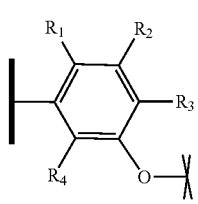

or

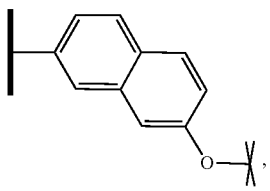

$R_1$, $R_2$, $R_3$ and $R_4$ being independently from each other selected from H, COCH$_3$, NH$_2$, NO$_2$, NHAc, OH, OMe, COOH, COOMe, CONHMe, Cl, Br, I, F, SMe or Me;

provided that y+n or y+m is different from 0;

in particular, m being comprised from 1 to 5;

in particular, n being comprised from 0 to 5;

D being selected from

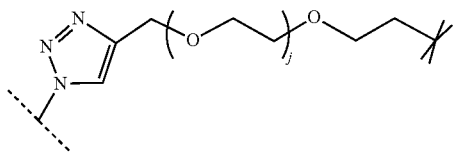

j being comprised from 0 to 8.

In an advantageous embodiment, the present Invention relates to a compound for its use, said compound being of formula (I)

A-(D)$_i$-B—C    (I)

wherein
i is equal to 0 or 1;
A is selected from

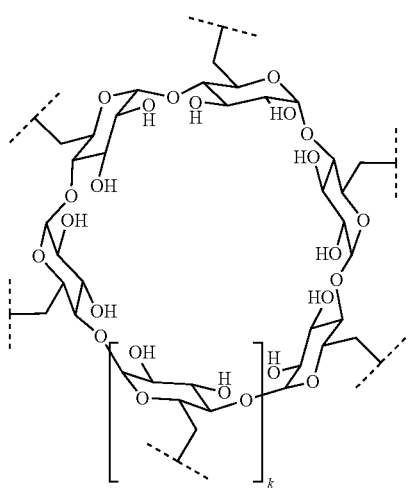
(A1)

k being equal to 1, 2, or 3; k being in particular equal to 1;

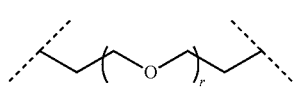
(A2)

r being comprised from 1 to 30, in particular from 1 to 4, from 5 to 9, from 10 to 15, from 16 to 20, from 21 to 25 or from 26 to 30;

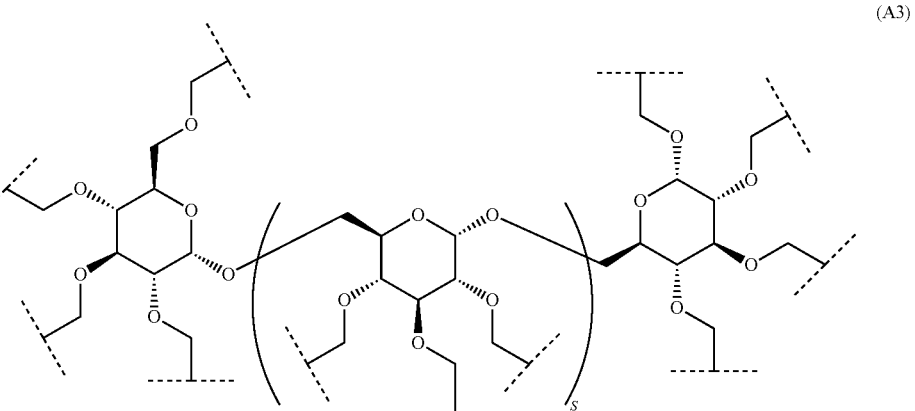
(A3)

s being comprised from 5 to 300; in particular from 60 to 80;

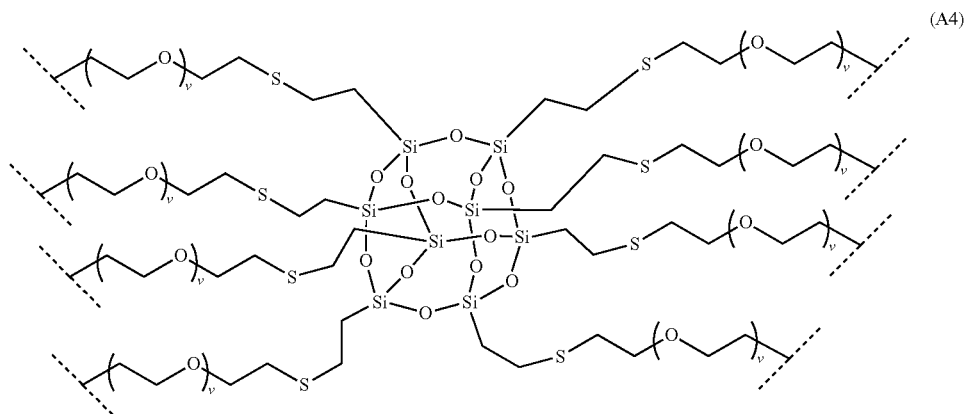 (A4)

v being comprised from 0 to 10; in particular from 1 to 8; preferably v being equal to 3;

B is of formula

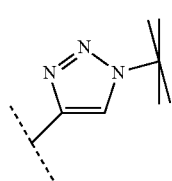 (B)

C is of formula

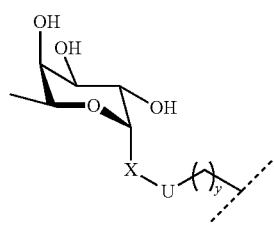

y being equal to 1;
X being selected from O, S or $CH_2$;
U being selected from

m being comprised from 0 to 8,

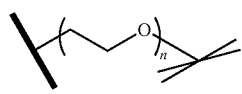

n being comprised from 0 to 8, or

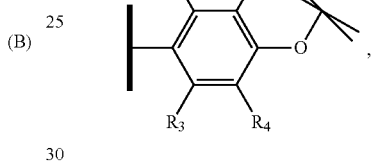

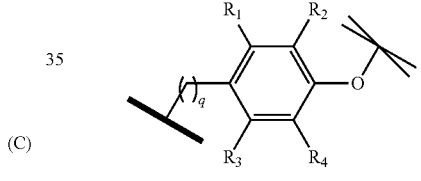 (C)

q being comprised from 1 to 10, $R_1$, $R_2$, $R_3$ and $R_4$ being independently from each other selected from H, $COCH_3$, $NH_2$, $NO_2$, NHAc, OH, OMe, COOH, COOMe, CONHMe, Cl, Br, I, F, SMe or Me;

in particular, m being comprised from 1 to 5;
in particular, n being comprised from 0 to 5;

D being selected from

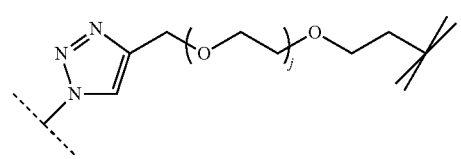

j being comprised from 0 to 8.

In a particular embodiment, the present invention relates to a compound bearing at least two fucose moieties for its use as a drug, said compound having a molecular weight comprised from 0.6 to 340 kDa, in particular from 0.6 to 2 kDa or from 1 to 7 kDa or from 2 to 10 kDa or from 5 to 340 kDa;

said compound being of formula (I)
A-(D)$_i$-B—C    (I)
wherein
i is equal to 0 or 1;
A is selected from
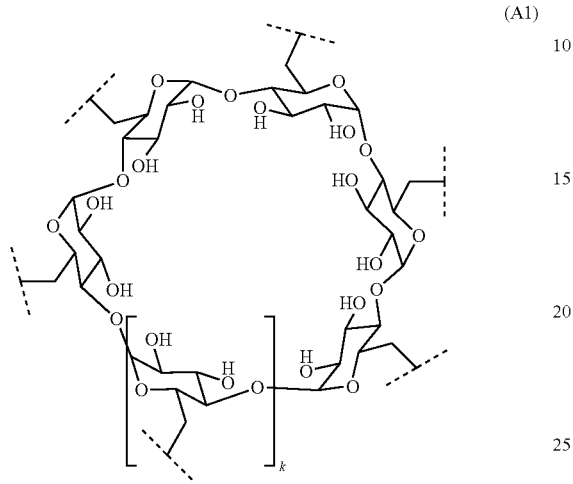
(A1)
k being equal to 1, 2, or 3; k being in particular equal to 1
(A2)
r being comprised from 1 to 30, in particular from 1 to 4, from 5 to 9, from 10 to 15, from 16 to 20, from 21 to 25 or from 26 to 30;
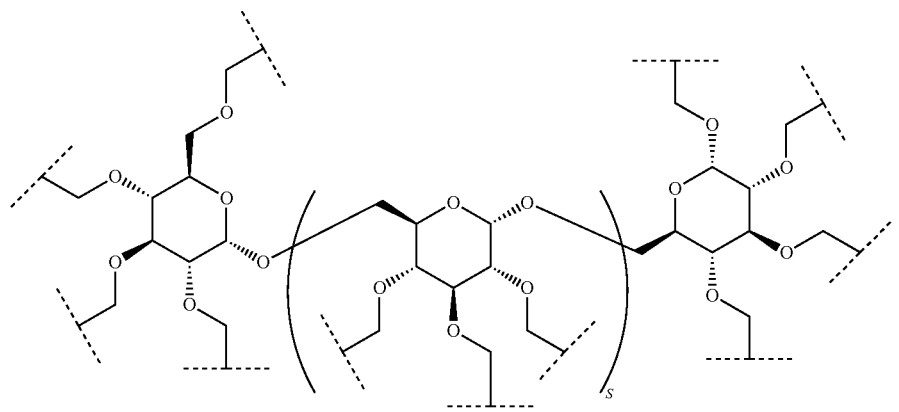
(A3)
s being comprised from 5 to 300; in particular from 60 to 80;

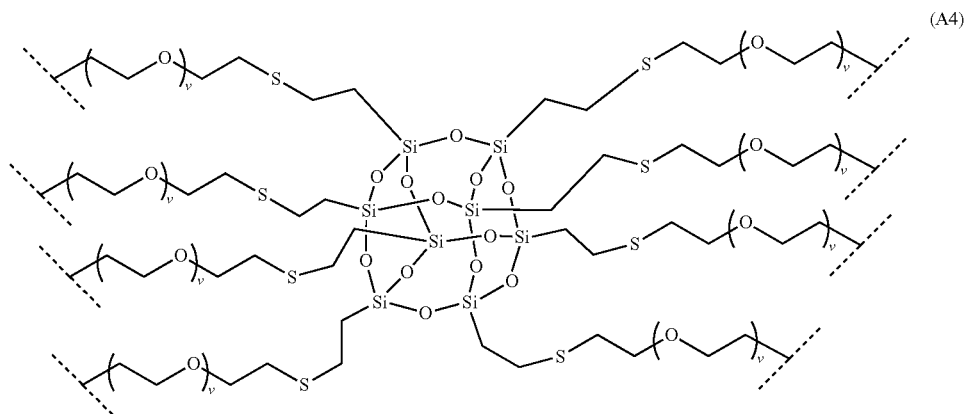
v being comprised from 0 to 10; in particular from 1 to 8; preferably v being equal to 3;
B is of formula
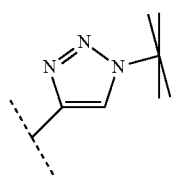 (B)
C is of formula
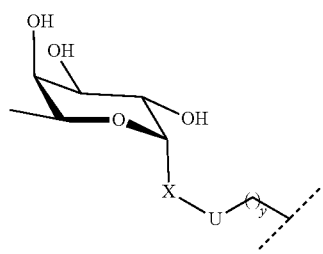 (C)
y being equal to 0 or 1;
X being selected from O, S or CH$_2$;
U being selected from
m being comprised from 0 to 8,
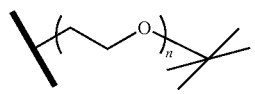
n being comprised from 0 to 8,
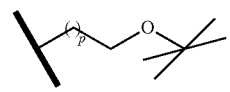
p being comprised from 1 to 10,
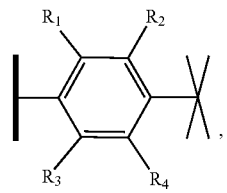
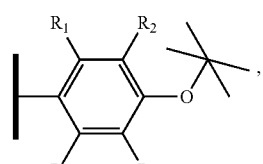
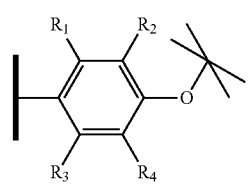

q being comprised from 1 to 10,

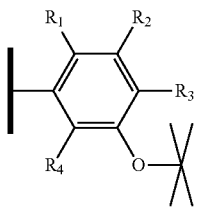

or

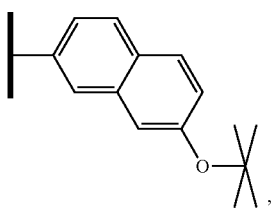

$R_1$, $R_2$, $R_3$ and $R_4$ being independently from each other selected from H, $COCH_3$, $NH_2$, $NO_2$, NHAc, OH, OMe, COOH, COOMe, CONHMe, Cl, Br, I, F, SMe or Me;
provided that y+n or y+m is different from 0;
in particular, m being comprised from 1 to 5;
in particular, n being comprised from 0 to 5;
D being selected from

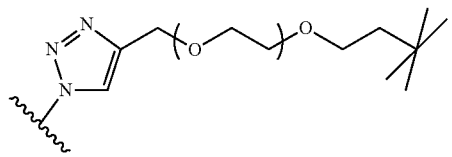

j
j being comprised from 0 to 8.

In an advantageous embodiment, the present Invention relates to a composition for its use as a drug comprising a compound as defined above as active ingredient.

In another advantageous embodiment, the present Invention relates to a composition for its use comprising a compound as defined above as active ingredient, formulated for its human and/or animal use.

In another advantageous embodiment, the present Invention relates to a composition for its use comprising a compound of formula (I) as active ingredient, formulated for its human and/or animal use.

In another advantageous embodiment, the present Invention relates to a composition for its use comprising a compound as defined above as active ingredient, said compound being used by respiratory route, in particular by inhalation.

In another advantageous embodiment, the present Invention relates to a composition for its use comprising a compound of formula (I) as active ingredient, said compound of formula (I) being used by respiratory route, in particular by inhalation.

Inhalable preparations comprising a compound of the Invention include inhalable powders, propellant-containing metered dose aerosols or propellant-free inhalable solutions. Inhalable powders according to the invention containing the active substance may consist of the active substance on its own or of a mixture of the active substance with physiologically acceptable excipients. Within the scope of the present invention, the term "propellant-free inhalable solutions" also includes concentrates or sterile inhalable solutions ready for use.

Inhalable powders: if the active substance of the Invention is present in a mixture with physiologically acceptable excipients, the following physiologically acceptable excipients may be used to prepare the inhalable powders according to the invention: monosaccharides (e.g. glucose or arabinose), disaccharides (e.g. lactose, saccharose, maltose), oligo- and polysaccharides (e.g. dextran), polyalcohols (e.g. sorbitol, mannitol, xylitol), salts (e.g. sodium chloride, calcium carbonate) or mixtures of these excipients with one another. Preferably, mono- or disaccharides are used, while the use of lactose or glucose is preferred, particularly, but not exclusively, in the form of their hydrates.

Propellant-containing inhalable aerosols: the propellant-containing inhalable aerosols which may be used according to the invention may contain a compound of the Invention dissolved in the propellant gas or in dispersed form. The propellant gases which may be used to prepare the inhalation aerosols according to the invention are known from the prior art. Suitable propellant gases are selected from among hydrocarbons such as n-propane, n-butane or isobutane and halohydrocarbons such as preferably fluorinated derivatives of methane, ethane, propane, butane, cyclopropane or cyclobutane. The propellant gases mentioned above may be used on their own or in mixtures thereof. Particularly preferred propellant gases are fluorinated alkane derivatives selected from TG134a (1,1,1,2-tetrafluoroethane), TG227 (1,1,1,2,3,3,3-heptafluoropropane) and mixtures thereof. The propellant-driven inhalation aerosols used within the scope of the use according to the invention may also contain other ingredients such as co-solvents, stabilisers, surfactants, antioxidants, lubricants and pH adjusters. All these ingredients are known in the art.

Propellant-free inhalable solutions: the compounds of the Invention are, in particular, used to prepare propellant-free inhalable solutions and inhalable suspensions. Solvents used for this purpose include aqueous or alcoholic, preferably ethanolic solutions. The solvent may be water on its own or a mixture of water and ethanol. The solutions or suspensions are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. It is also possible to use the acids which have already formed an acid addition salt with one of the active substances. Of the organic acids, ascorbic acid, fumaric acid and citric acid are preferred. If desired, mixtures of the above acids may also be used, particularly in the case of acids which have other properties in addition to their acidifying qualities, e.g. as flavourings, antioxidants or complexing agents, such as citric acid or ascorbic acid, for example.

Co-solvents and/or other excipients may be added to the propellant-free inhalable solutions used for the purpose according to the invention. Preferred co-solvents are those which contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters.

The terms "excipients" and "additives" in this context denote any pharmacologically acceptable substance which is not an active substance but which can be formulated with the active substance or substances in the pharmacologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilisers, complexing agents, antioxidants and/or preservatives which guarantee or prolong the shelf life of the finished pharmaceutical formulation, flavourings, vitamins and/or other additives known in the art. The additives also include pharmacologically acceptable salts such as sodium chloride as isotonic agents. The preferred excipients include antioxidants such as ascorbic acid, for example, provided that it has not already been used to adjust the pH, vitamin A, vitamin E, tocopherols and similar vitamins or provitamins occurring in the human body. Preservatives may be used to protect the formulation from contamination with pathogens. Suitable preservatives are those which are known in the art, particularly acetyl pyridinium chloride, benzalkonium chloride or benzoic acid or benzoates such as sodium benzoate in the concentration known from the prior art.

The compositions of the invention can also be in the form of sterile powders, granules, tablets, concentrated solutions or suspensions, or freeze-dried powders reconstituted with sterile water or saline.

Extemporaneous injection solutions and suspensions can be prepared from these sterile powders, granules, tablets, concentrated solutions or suspensions, or freeze-dried powders reconstituted with sterile water or saline before administration to the subject.

The suitable formulations for the desired administration route are known from the man skilled in the art and described, for example in: Remington, The science and Practice of Pharmacy, 22$^{ème}$ édition, 2013, The Pharmaceutical Press.

In another advantageous embodiment, the present Invention relates to a composition for its use comprising a compound as defined above as active ingredient, said composition comprising from 1 mg to 1.4 g of active ingredient; in particular from 1 to 7 mg of active ingredient, or from 7 to 700 mg of active ingredient, or from 70 to 350 mg of active ingredient, or from 350 to 700 mg of active ingredient, or from 700 mg to 1.05 g of active ingredient, or from 1.05 to 1.4 g of active ingredient.

According to the present Invention, a dosage from 1 mg to 1.4 g of active ingredient, in particular from 1 to 7 mg of active ingredient, or from 7 to 700 mg of active ingredient, or from 70 to 350 mg of active ingredient, or from 350 to 700 mg of active ingredient, or from 700 mg to 1.05 g of active ingredient, or from 1.05 to 1.4 g of active ingredient, corresponds to a daily intake by nebulization to a human body.

In another advantageous embodiment, the present Invention relates to a composition for its use comprising a compound of formula (I) as active ingredient, said composition comprising from 1 mg to 1.4 g of active ingredient; in particular from 1 to 7 mg of active ingredient, or from 7 to 700 mg of active ingredient, or from 70 to 350 mg of active ingredient, or from 350 to 700 mg of active ingredient, or from 700 mg to 1.05 g of active ingredient, or from 1.05 to 1.4 g of active ingredient.

In an advantageous embodiment, the present Invention relates to a composition for its use comprising a compound as defined above as active ingredient, said composition comprising from 200 mg to 10 g of active ingredient; in particular from 400 mg to 7 g of active ingredient.

According to the present Invention, a dosage from 200 mg to 10 g of active ingredient, in particular from 400 mg to 7 g of active ingredient, corresponds to a daily intake by oral route to a human body.

In another advantageous embodiment, the present Invention relates to a composition for its use comprising a compound of formula (I) as active ingredient, said composition comprising from 200 mg to 10 g of active ingredient; in particular from 400 mg to 7 g of active ingredient.

In an advantageous embodiment, the present Invention relates to a composition for its use comprising a compound as defined above as active ingredient, said composition comprising from 10 mg to 10 g of active ingredient; in particular from 50 mg to 7 g of active ingredient. According to the present Invention, a dosage from 10 mg to 10 g of active ingredient, in particular from 50 mg to 7 g of active ingredient, corresponds to a daily intravenous intake to a human body.

In another advantageous embodiment, the present Invention relates to a composition for its use comprising a compound of formula (I) as active ingredient, said composition comprising from 10 mg to 10 g of active ingredient; in particular from 50 mg to 7 g of active ingredient.

In another advantageous embodiment, the present Invention relates to a composition for its use comprising a compound as defined above as active ingredient, said composition comprising from 0.015 to 20 mg/kg of active ingredient; in particular from 0.015 to 0.1 mg/kg of active ingredient, or from 0.1 to 10 mg/kg of active ingredient, or from 1 to 5 mg/kg of active ingredient, or from 5 to 10 mg/kg of active ingredient, or from 10 to 15 mg/kg of active ingredient, or from 15 to 20 mg/kg of active ingredient.

According to the present Invention, a dosage from 0.015 to 20 mg/kg of active ingredient, in particular from 0.015 to 0.1 mg/kg of active ingredient, or from 0.1 to 10 mg/kg of active ingredient, or from 1 to 5 mg/kg of active ingredient, or from 5 to 10 mg/kg of active ingredient, or from 10 to 15 mg/kg of active ingredient, or from 15 to 20 mg/kg of active ingredient, corresponds to a daily intake by nebulization to a human body of 70 kg.

In another advantageous embodiment, the present Invention relates to a composition for its use comprising a compound of formula (I) as active ingredient, said composition comprising from 0.015 to 20 mg/kg of active ingredient; in particular from 0.015 to 0.1 mg/kg of active ingredient, or from 0.1 to 10 mg/kg of active ingredient, or from 1 to 5 mg/kg of active ingredient, or from 5 to 10 mg/kg of active ingredient, or from 10 to 15 mg/kg of active ingredient, or from 15 to 20 mg/kg of active ingredient.

In an advantageous embodiment, the present Invention relates to a composition for its use comprising a compound as defined above as active ingredient, said composition comprising from 3 mg/kg to 143 mg/kg of active ingredient; in particular from 6 mg/kg to 100 mg/kg of active ingredient.

According to the present Invention, a dosage from 3 mg/kg to 143 mg/kg of active ingredient, in particular from 6 mg/kg to 100 mg/kg of active ingredient, corresponds to a daily intake by oral route to a human body of 70 kg.

In another advantageous embodiment, the present Invention relates to a composition for its use comprising a compound of formula (I) as active ingredient, said composition comprising from 3 mg/kg to 143 mg/kg of active ingredient; in particular from 6 mg/kg to 100 mg/kg of active ingredient.

In an advantageous embodiment, the present Invention relates to a composition for its use comprising a compound as defined above as active ingredient, said composition comprising from 0.15 mg/kg to 143 mg/kg of active ingredient; in particular from 1 mg/kg to 100 mg/kg of active ingredient.

According to the present Invention, a dosage from 0.15 mg/kg to 143 mg/kg of active ingredient, in particular from 1 mg/kg to 100 mg/kg of active ingredient, corresponds to a daily intravenous intake to a human body of 70 kg.

In another advantageous embodiment, the present Invention relates to a composition for its use comprising a compound of formula (I) as active ingredient, said composition comprising from 0.15 mg/kg to 143 mg/kg of active ingredient; in particular from 1 mg/kg to 100 mg/kg of active ingredient.

In another advantageous embodiment, the present Invention relates to a composition for its use comprising a compound as defined above as active ingredient, said compound being in association with an antifungal agent such as an azole antifungal agent, a polyene antifungal agent or an echinocandin antifungal agent.

In another advantageous embodiment, the present Invention relates to a composition for its use comprising a compound of formula (I) as active ingredient, said compound being in association with an antifungal agent such as an azole antifungal agent, a polyene antifungal agent or an echinocandin antifungal agent.

FIGURES

FIG. 1 is describing the microcalorimetry principle. I) Apparatus wherein A is the Adiabatic jacket, B is the reference cell, C is the sample cell where the protein is, D is the stirring syringe to add the ligand, E is a constant power and F the feedback power maintaining constant the temperature in both cells; II) raw data; III) integrated data.

Figure 2:
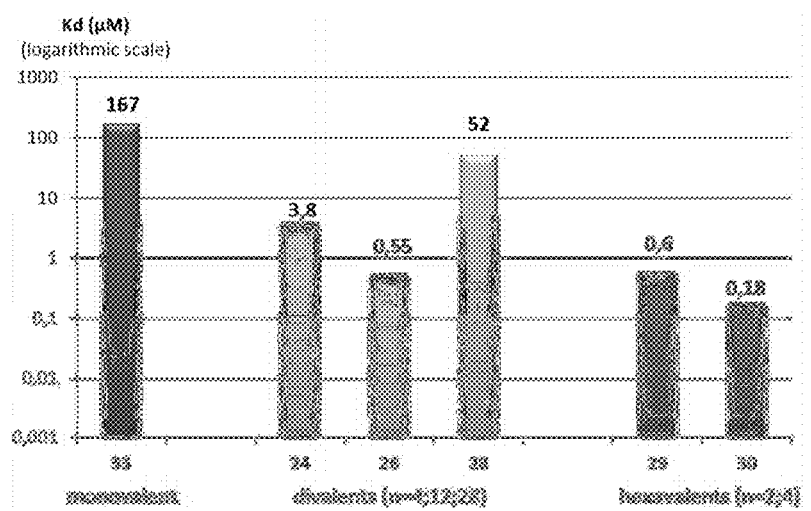

FIG. 2 provides a histogram comparing the dissociation constants of the multivalent fucose derivatives of the Invention and the reference monovalent compound 33.

Figure 3:
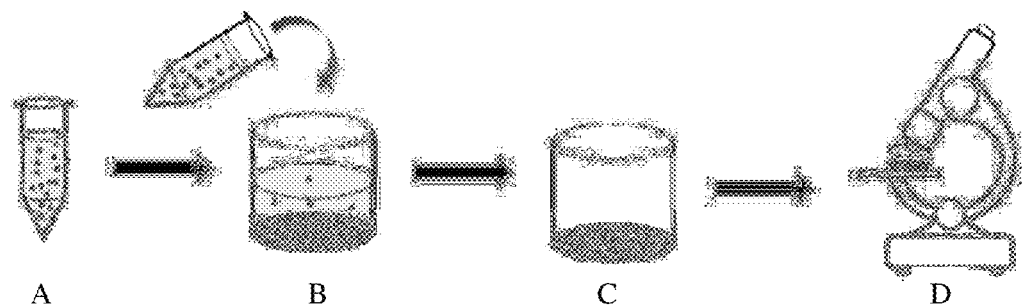

FIG. 3 is a general scheme of the adhesion test of conidia on pneumocytes in the presence of the fucose derivatives from the Invention. A represents the inhibitor/spores co-incubation, B represents the adding of the co-incubation on pneumocytes A549, C represents the rinsing of the cells and D is the counting under a microscope of the spores adhered to the cellular layer.

Figure 4:
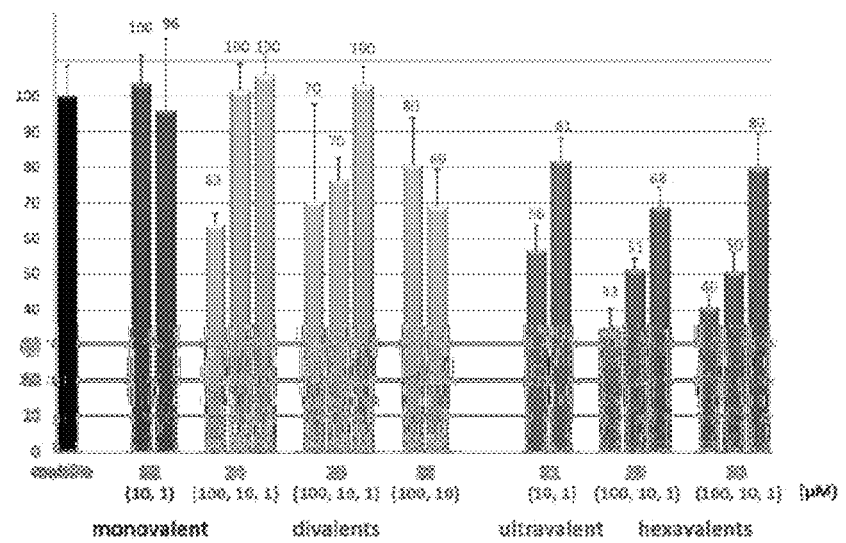

FIG. 4 provides a comparison of the percentage of residual adhesion of conidia from *Aspergillus* fumigants on pneumocytes in the presence of the multivalent fucose derivatives from the Invention at a concentration of 100, 10 and 1 µM.

Figure 5:
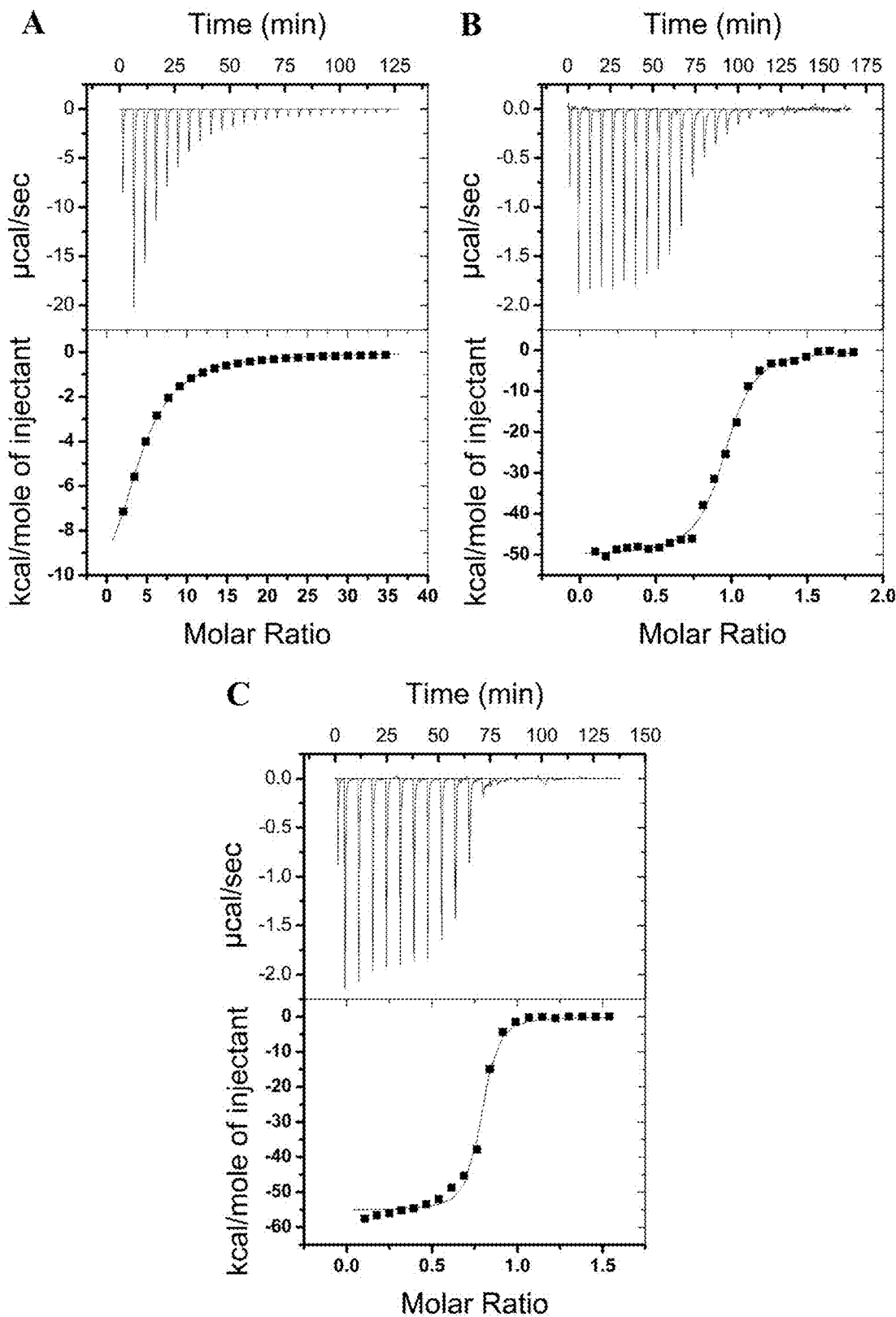

FIG. 5 provides isothermal titration calorimetry data. Thermograms obtained for the titration of AFL at 50 µM (A), 12.5 µM (B) and 10 µM (C) by αMeFuc at 10 mM (A), compound 30 at 126 µM (B) and compound 42 at 130 µM (C) at 25° C. Lower panel: integration of data with curve fitted for "one binding site" model. Molar ratio is defined as the number of compound molecules per lectin monomer.

Figure 6:
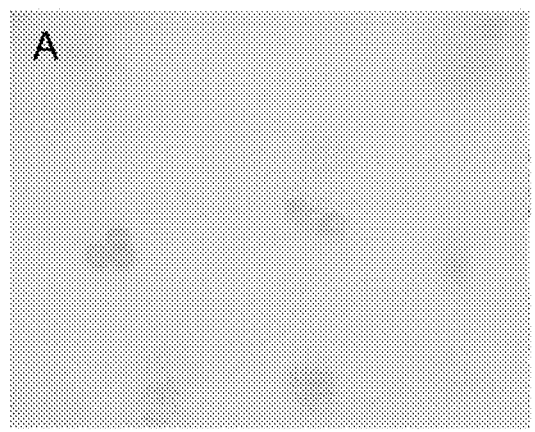
Figure 6:
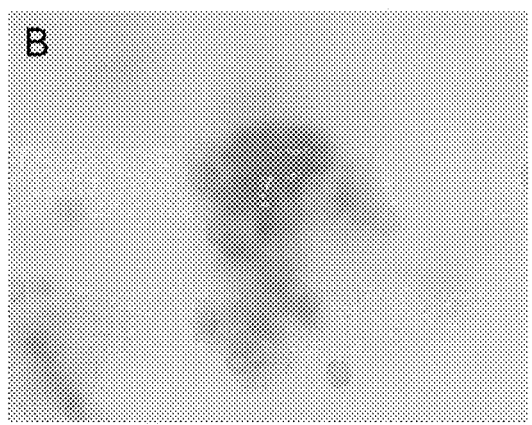

FIG. 6 provides images of formation of *A. fumigatus* spore agglomerates with compound 29 at 10 µM (B) and control (A).

EXAMPLES

Material

All reagents were purchased from Acros Organics, Alfa Aesar, Carbosynth or Aldrich and were used without further purification. Dichloromethane ethyl acetate and petroleum ether were distilled on a Buchi rotavapor R-220-SE. Acetonitrile, pyridine, benzene and DMF were freshly distilled from calcium hydride under argon. THF was distilled on sodium, benzophenone and under argon. Reactions requiring anhydrous conditions were performed under argon. Column chromatography was conducted on silica gel Kieselgel SI60 (40-63 µm) from Merck, or on Silica cartridge from Interchim and eluted via a Puriflash 430 with an UV and ELSD detection. Thin layer chromatography (TLC): Merck Silica gel 60 F254 analytical plates, detection either with UV (254 nm) or dipping in a solution of cerium molybdate, potassium permanganate, nihydrine and subsequent heating. Microwave experiments were conducted in sealed vials in commercial microwave reactors especially designed for synthetic chemistry (MultiSYNTH, Milestone). The instrument features a special shaking system that ensures high homogeneity of the reaction mixtures.

Nuclear Magnetic Resonance Spectroscopy $^1$H and $^{13}$C NMR spectra were recorded on Bruker Avance 300 spectrometer fitted with a 5 mm i.d. BBO probe carefully tuned to the recording frequency of 300.13 MHz (for $^1$H) and 75.47 MHz (for $^{13}$C), the temperature of the probe was set at room temperature (around 293-294 K), on a Bruker Avance 400 spectrometer fitted with a 5 mm i.d. BBFO+ probe carefully tuned to the recording frequency of 400.13 MHz (for $^1$H) and 100.61 MHz (for $^{13}$C), the temperature of the probe was set at 303 K, on a Bruker Avance III 500 spectrometer fitted with a 5 mm i.d. $^{13}$C/$^1$H cryoprobe carefully tuned to the recording frequency of 500.13 MHz (for 1H) and 125.76 MHz (for $^{13}$C), the temperature of the probe was set at 303 K. The spectra are referenced to the solvent in which they were run (7.26 ppm for 1H CDCl$_3$ and 77.16 ppm for 13C CDCl$_3$, 2.50 ppm for 1H DMSO-d6 and 39.52 ppm for $^{13}$C DMSO-d6, 3.31 ppm for $^1$H CD$_3$OD and 49.00 ppm for $^{13}$C, 7.16 ppm for $^1$H C$_6$D$_6$ and 128.06 ppm for $^{13}$C C$_6$D$_6$, 5.32 ppm for $^1$H CD$_2$Cl$_2$ and 53.84 ppm for $^{13}$C, 4.79 ppm for $^1$H D$_2$O). Chemical shifts (δ) are given in parts per million (ppm) and coupling constants (J) are given in Hz, Multiplicity of signals is indicated as following: s (singulet), d (doublet), t (triplet), q (quadruplet), m (multiplet), brs (broad singulet), dd (doublet of doublet), dt (doublet of triplet) . . . . The numbering used for NMR attribution is different from IUPAC numbering, and written on each molecule.

Mass Spectrometry

Low resolution mass spectrometry (MS) was recorded on a ThermoFinnigan DSQII quadripolar spectrometer (coupled with a TracUltra GC apparatus) for Chemical Ionization (CI), on a ThermoFinnigan LCQ Advantage spectrometer for ElectroSpray Ionisation (ESI). High resolution mass spectrometry (HRMS) was recorded on a ThermoFinnigan MAT95XL spectrometer (for CI), on a ThermoFisher Scientific LTQ-Orbitrap spectrometer (for ESI+), on a Bruker Autoflex III spectrometer (for MALDI+).

Optical Rotation Measurements

Optical rotation data were obtained on a Perkin-Elmer 341 polarimeter, in a 100 mm cell, under Na lamp radiation at 20° C.

Example 1: Preparation of $H_2SO_4$-Silica

To a suspension of silica (10 g) in diethyl ether (50 ml) was added sulfuric acid (3 ml). The mixture is stirred at r.t. during 15 min and then evaporated under vacuum. The resulted powder is dried at 80° C. overnight.

Example 2: Fisher Glycosylation G1

To a solution of sugar (1 eq.) in alcohol (5 eq.) was added $H_2SO_4$-silica (5 mg/mmol) prepared as described in general procedure. The mixture was stirred at 80° C. for 6 h. After filtration and evaporation of the solvent, the compound was per-O-acetylated in $Ac_2O$-pyridine 1:1 (10 ml/mmol). The solvent was removed under reduced pressure, dissolved in DCM (20 mL/mmol) and washed with $NaHCO_3$ saturated solution (2×20 mL/mmol). The organic phases are dried over $MgSO_4$, filtered and concentrated under reduced pressure. The reaction mixture was purified on a silica gel column to give the pure α-anomer.

Example 3: Azidation G2

To a solution of mesylated/bromated compound (1 eq.) in DMF (10 ml/mmol) was added sodium azide (2 eq.). Then, the mixture was heated to 80° C. for 16 h. After cooling to room temperature, the mixture was concentrated under vacuum. The crude product was dissolved in DCM (20 mL/mmol) washed with $H_2O$ (20 mL/mmol) and the aqueous layer was extracted with DCM (2×20 mL/mmol). The organic layers are dried over $MgSO_4$, filtered and concentrated under reduced pressure. The resulted product is purified by flash chromatography.

Example 4: Conner Catalyzed Azide-Alkyne Cycloaddition Method G3 (Method A)

The azide derivative and the alkyne derivative (1.1 or 0.9 eq./azide function) were dissolved in dioxane (2 mL/mmol). A solution of copper sulfate (0.2 eq./azide function) and sodium ascorbate (0.4 eq./azide function) in water (0.5 mL/mmol) was added and the mixture was heated at 60° C. until completion. The mixture was dissolved in DCM (50 mL/mmol), washed with a solution of EDTA (50 mL/mmol) and the aqueous layer was extracted twice with DCM (2×50 mL/mmol). The organic layer was then dried over $MgSO_4$, filtered, concentrated under reduced pressure and purified.

Example 5: Copper Catalyzed Azide-Alkyne Cycloaddition Method G4 (Method B)

The azide derivative and the alkyne derivative (1.1 or 0.9 eq/azide function) were dissolved in dioxane (2 mL/mmol). A solution of copper sulfate (0.4 eq./azide function) and sodium ascorbate (0.8 eq./azide function) in water (0.5 mL/mmol) was added and the mixture was heated to 80° C. under microwave condition in a sealed vessel during 90 min. The mixture was dissolved in DCM (50 mL/mmol), washed with a solution of EDTA (50 mL/mmol) and the aqueous layer was extracted twice with DCM (2×50 mL/mmol). The organic layer was then dried over $MgSO_4$, filtered, concentrated under reduced pressure and purified.

Example 6: Deprotection of Acetyl Groups Using Sodium Methanolate Method G5

The protected carbohydrate (1 eq.) was dissolved in methanol (2 mL/mmol) and a sodium methanolate solution (0.1 M, 0.05 eq./acetyl group) was added. The mixture was stirred at r.t. for 3 h. After completion, water was added (0.5 mL/mmol), followed by Amberlite® IR120. The mixture was stirred until the pH was around 5. After removal of the resin by filtration, the resulted mixture was lyophilized.

Example 7: Deprotection of Acetyl Groups Using Sodium Methanolate Method G6

The protected carbohydrate (1 eq.) was dissolved in $MeOH/H_2O$ (1:1, 1 mL/mmol). Amberlite resin IRN 78 OH⁻ 1.25 meq/mL (150 mg/mmol) was added, and the mixture was stirred overnight at r.t. The resin was filtered off and washed with methanol and water. The solvent was evaporated under reduced pressure.

Example 8: Mesylation G7

OEG (1 eq.), and triethylamine (2 eq.) were dissolved in dichloromethane (15 mL/mmol), and cooled to 0° C. Methanesulfonyl chloride (2 eq.) was added dropwise and the mixture was stirred overnight. The filtrate was washed with saturated sodium carbonate (15 ml/mmol), extracted 3 times with dichloromethane (3×15 mL/mmol) and dried over anhydrous sodium sulfate. The solution was concentrated under reduced pressure and the crude product purified via silica gel column chromatography eluting with DCM/MeOH.

Example 9: Removal of Trityl Ether Protecting Group G8

Triisopropyl silane (7 eq) was added to a functionalized OEG ether solution of DCM (20 mL/mmol). The mixture was then treated with TFA (1 mL/mmol) for 1 h. After consumption of the starting material; excess TFA and DCM were removed under reduced pressure after co-evaporation with toluene. The residue was taken up in methanol (10 ml/mmol) and treated with sodium methoxide (1M, 2 mL/mmol). The solvant was concentrated under reduced pressure, a saturated ammonium chloride solution (20 mL/mmol) was added to the residue and the aqueous layer was extracted with DCM (5×20 mL/mmol). The combined organic solutions were dried over magnesium sulfate and evaporated to give the crude product for purification by flash chromatography (DCM/MeOH)

Example 10: Glycosylation G9

Boron trifluoride ethyl etherate (5 eq.) was added dropwise at 0° C. to a solution of per-O-acetylated sugar (1 eq.) and alcohol acceptor (4 eq.) in anhydrous dichloromethane (15 mL/mmol). The solution was stirred at r.t. for 16 h. Potassium carbonate (1 g/mmol) was added by portions and the reaction mixture was stirred for further 1 h and filtered. The filtrate was diluted with dichloromethane (20 mL/mmol), washed with water (2×20 mL/mmol), dried over

Example 11: Compound 7

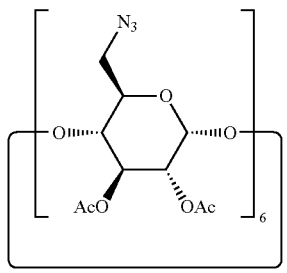

To a solution of triphenylphosphine (16.3 g, 62.1 mmol) and iodine (16.8 g, 66.24 mmol) in dry DMF (80 mL) was added CD (5 g, 4.14 mmol) and the solution was stirred at 70° C. during 20 h. It was then concentrated under reduced pressure to about 30 mL and the pH was adjusted to 9 by addition of sodium methoxide in methanol (3M, 30 mL). The solution was kept at room temperature for 30 min, after what it was poured into ice water (20 mL/mmol). The precipitate was collected by filtration and washed with methanol to afford 6-deoxy-6-iodo-CDs 6 in a quantitative yield.

6-deoxy-6-iodo-CD (6) (1 g, 0.6 mmol) was dissolved in DMF (15 mL), and $NaN_3$ (0.36 g, 5.5 mmol) was added. The resulting suspension was stirred at 70° C. for 16 h. The suspension was then concentrated under reduced pressure and dissolved in a mixture of pyridine and acetic anhydride (1/1, 8 mL) before addition of DMAP (50 mg, 0.4 mmol). The solution was stirred at r.t. for 3 h under nitrogen and then concentrated under reduced pressure. The residue was purified by flash chromatography (Cyclohexane/EtOAc: 7/3) to give compound 7 in 86% yield as a white powder.

The analytical data of 7 was in complete agreement with literature data.

Example 12: Compound 8

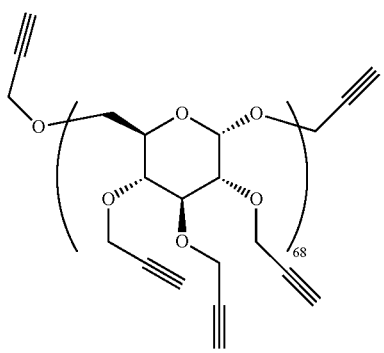

A solution of propargyl bromide (0.76 g, 4.92 mmol) in toluene (0.6 mL) was added dropwise to a stirred solution of dextran (0.1 g, 0.615 mmol of sugar unit) in 0.3 mL water, KOH—$H_2O$ (0.64 g, 8.6 mmol) and TEBAC (8.4 mg, 36.9 μmol) were added and the mixture was stirred for 20 min at 10-15° C. The reaction was further carried out for 48 h at rt.

Acetone (1 mL) was added, the organic layer was separated and the compound was precipitated in ethanol (75 mL). The residue was filtered on millipore, sequentially washed with water (25 mL) and ethanol (25 mL) then dried under vacuum to afford compound 8 as a white powder in 60% yield.

The analytical data of 8 were in complete agreement with literature data.

Example 13: Compound 9

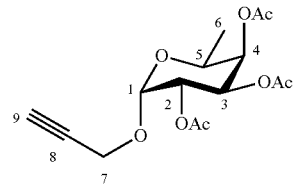

Obtained following the Fisher glycosylation protocol G1 of Example 2. The crude product was chromatographed on a silica gel column with 8/2 (cyclohexane/AcOEt) as eluent to afford 9 (51% yield) as a white solid.

$^1$H NMR (300 MHz, $CDCl_3$): δ (ppm): 5.38 (dd, J=11.0 Hz, J=3.4 Hz, 1H; H-3), 5.32 (dd, J=1.3 Hz, 1H; H-4), 5.27 (d, J=3.8 Hz, 1H; H-1), 5.18 (dd, 1H; H-2), 4.27 (d, J=2.4 Hz, 2H; H-7), 4.21 (br q, J=6.5 Hz, 1H; H-5), 2.44 (t, 1H; H-9), 2.18, 2.10, 2.00 (3 s, 9H; $COCH_3$), 1.16 (d, 3H; H-6)

$^{13}$C NMR (75 MHz, $CDCl_3$): δ (ppm): 170.5, 170.3, 169.9 (3 ($COCH_3$), 95.0 (C-1), 78.6 (C-8), 74.8 (C-9), 71.0 (C-4), 67.8 (C-2), 67.7 (C-3), 64.9 (C-5), 55.2 (C-7), 20.7, 20.6, 20.5 (3 $COCH_3$), 15.7 (C-6).

MS, ESI m/z: $[M+H]^+$=351.2 Da

Example 14: Compound 10

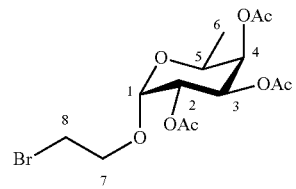

Obtained following the fisher glycosylation method G1 of Example 2. The crude product was chromatographed on a silica gel column with 8/2 (Cyclohexane/AcOEt) as eluent to afford 10 (55% yield) as a yellow gum.

$^1$H NMR (300 MHz, $CDCl_3$): δ (ppm): 5.32 (dd, J=11.0 Hz, J=3.5 Hz, 1H; H-3), 5.30 (dd, J=1.5 Hz, J=3.5 Hz, 1H: H-4), 5.27 (d, J=3.8 Hz, 1H; H-1), 5.18 (dd, J=3.8 Hz, J=11.0 Hz, 1H; H-2), 3.99 (m, J=5.7 Hz, 1H, H-7a), 3.83 (m, J=5.7 Hz, 1H, H-7b), 3.50 (t, J=5.7 Hz, 2H, H-8), 2.18, 2.08, 1.99 (3 s, 9H, $COCH_3$), 1.24 (d, J=6.41 Hz, 3H)

$^{13}$C NMR (75 MHz, $CDCl_3$): δ (ppm): 170.5, 170.3, 169.7 (3 $COCH_3$), 96.4 (C-1), 70.1 (C-8), 69.8 (C-9), 69.6 (C-4), 68.4 (C-2), 63.6 (C-3), 62.5 (C-5), 30.1 (C-7), 29.8, 21.0, 20.7 (3 $COCH_3$), 16.2 (C-6).

MS, ESI m/z: $[M+H]^+$=419.0 Da

Example 15: Compound 11

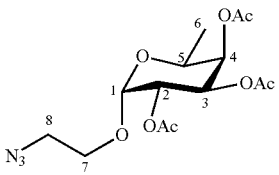

Obtained following the azidation method G2 of Example 3. The crude product was chromatographed on a silica gel column with 7/3 (Cyclohexane/AcOEt) as eluent to afford 11 (74% yield) as a yellow gum.

$^1$H NMR (300 MHz, CDCl$_3$): δ (ppm): 4.90 (d, J=2.5 Hz, 1H, H-1), 3.99 (q, J=6.8 Hz, 1H, H-5), 3.93-3.78 (m, 3H), 3.77-3.68 (m, 2H), 3.55-3.38 (m, 2H, CH$_2$N$_3$), 1.29 (d, J=6.6 Hz, 3H, CH$_3$).

$^{13}$C NMR (75 MHz, CDCl$_3$): δ (ppm): 98.0 (C-1), 71.8 (C-4), 71.1 (C-3), 69.0 (C-2), 67.0 (OCH$_2$), 66.5 (C-5), 50.8 (CH$_2$N$_3$), 16.3 (CH$_3$).

MS, ESI: [M+H]$^+$=360.1 Da

The analytical data of 10 and 11 were in complete agreement with literature data.

Example 16: Compound 14

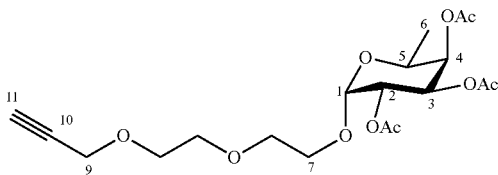

Obtained following the fisher glycosylation method G1 of Example 2. The crude product was chromatographed on a silica gel column with 98/2 (DCM/MeOH) as eluent to afford 14 (65% yield) as a yellow gum.

$^1$H NMR (300 MHz, CDCl$_3$): δ (ppm): 5.35 (dd, J=3.4, 9.6 Hz, 1H, H-2), 5.22 (dd, J=1.1, J=3.4 Hz, 1H, H-4), 5.12 (d, J=3.7 Hz, 1H, H-3), 5.10 (s, 1H, H-1), 4.27-4.19 (q, J=7.3 Hz, 1H, H-5), 4.20 (d, J=2.5 Hz, 2H, H-9), 3.78-3.70 (m, 2H, H-7), 3.70-3.60 (m, 6H, CH$_2$O), 2.40 (t, J=2.3 Hz, 1H, H-11), 2.13, 2.04, 1.95 (3s, 9H, COCH$_3$), 1.13 (d, J=6.6 Hz, 3H, H-6).

$^{13}$C NMR (75 MHz, CDCl$_3$): δ (ppm): 170.7, 170.5, 170.1 (3s, 3C, COCH$_3$), 96.3 (C-1), 79.7 (C-10), 74.6 (C-11), 71.3 (C-4), 70.8-69.2 (CH$_2$O), 68.2 (C-3), 68.1 (C-2), 67.6 (C-7), 64.4 (C-5), 58.4 (C-9) 20.9, 20.8, 20.7 (3s, 3C, COCH$_3$), 15.9 (C-6).

HRMS, ESI: m/z: [M+Na]$^+_{calc}$=439.1580 Da, [M+Na]$^+_{mes}$=439.1578 Da

[α]$_D$ (CHCl$_3$, c=1, 20° C.)=−15.8 Da

Example 17: Compound 15

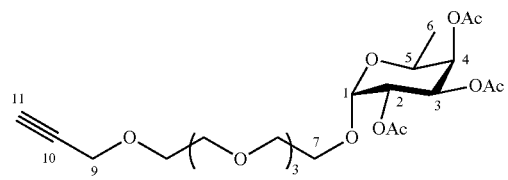

Obtained following the fisher glycosylation method G1 of Example 2. The crude product was chromatographed on a silica gel column with 98/2 (DCM/MeOH) as eluent to afford 15 (55% yield) as a yellow gum.

$^1$H NMR (300 MHz, CDCl$_3$): δ (ppm): 5.37 (dd, J=3.4, 9.6 Hz, 1H, H-2), 5.24 (dd, J=1.1, J=3.4 Hz, 1H, H-4), 5.13 (d, J=3.7 Hz, 1H, H-3), 5.11 (s, 1H, H-1), 4.29-4.20 (q, J=7.3 Hz, 1H, H-5), 4.17 (d, J=2.5 Hz, 2H, H-9), 3.79-3.70 (m, 2H, H-7), 3.70-3.60 (m, 14H, CH$_2$O), 2.41 (t, J=2.3 Hz, 1H, H-11), 2.12, 2.04, 1.96 (3s, 9H, COCH$_3$), 1.11 (d, J=6.6 Hz, 3H, H-6).

$^{13}$C NMR (75 MHz, CDCl$_3$): δ (ppm): 170.8, 170.5, 170.2 (3s, 3C, COCH$_3$), 96.3 (C-1), 79.6 (C-10), 74.7 (C-11), 71.2 (C-4), 71.0-69.1 (CH$_2$O), 68.2 (C-3), 68.0 (C-2), 67.7 (C-7), 64.3 (C-5), 58.3 (C-9) 21.0, 20.8, 20.7 (3s, 3C, COCH$_3$), 15.8 (C-6)

HRMS, ESI: m/z: [M+Na]$^+_{calc}$=527.2104 Da, [m+Na]$^+_{mes}$=527.2101 Da

[α]$_D$ (CHCl$_3$, c=1, 20° C.)=−11.4 Da

Example 18: Compound 16

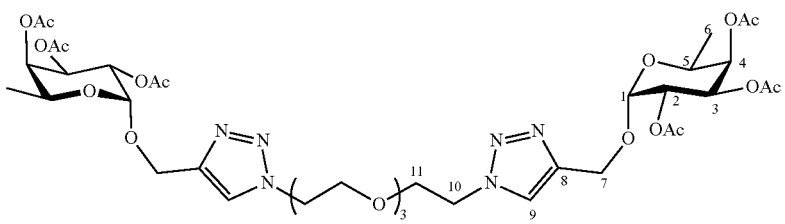

Obtained following the CuAAC method G3 of Example 4. The crude product was chromatographed on a silica gel column with 95/5 (DCM/MeOH) as eluent to afford 16 (85% yield) as a colorless oil.

$^1$H NMR (300 MHz, CDCl$_3$): δ (ppm): 5.32 (dd, J=11.0 Hz, J=3.6 Hz, 2H, H-3), 5.26 (bd, J=6.5 Hz, 2H, H-4), 5.15 (d, J=3.4 Hz, 2H, H-1), 5.18 (dd, J=3.4 Hz, J=11.0 Hz, 2H, H-2), 4.79 (d, J=11.7 Hz, 2H, H-7a), 4.63 (d, J=11.7 Hz, 2H, H-7b), 4.53 (t, J=4.8 Hz, 4H, H-11), 4.19 (br q, J=6.5 Hz, 2H, H-5), 3.86 (t, J=4.8 Hz, 4H, H-10), 3.65-3.53 (m, 8H, CH$_2$O), 2.14, 2.00, 1.90 (3 s, 18H; COCH$_3$), 1.11 (d, J=6.3 Hz, 6H, H-6)

$^{13}$C NMR (75 MHz, CDCl$_3$): δ (ppm): 170.7, 170.5, 170.0 (3 (COCH$_3$), 142.9 (C-8), 124.0 (C-9), 95.7 (C-1), 71.2 (C-4), 70.6-70.4 (CH$_2$O), 69.5 (C-10), 68.1 (C-2), 68.0 (C-3), 64.7 (C-5), 50.4 (C-7), 20.9, 20.8, 20.7 (3 COCH$_3$), 15.9 (C-6)

HRMS, MALDI: m/z: [M+H]$^+_{calc}$=901.3678 Da, [M+H]$^+_{mes}$=901.3682 Da

[α]$_D$ (CHCl$_3$, c=1, 20° C.)=−13.2

Example 19: Compound 17

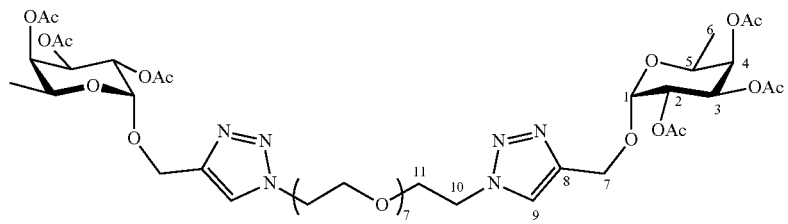

Obtained following the CuAAC method G3 of Example 4. The crude product was chromatographed on a silica gel column with 95/5 (DCM/MeOH) as eluent to afford 17 (82% yield) as a colorless oil.

$^1$H NMR (300 MHz, CDCl$_3$): δ (ppm): 5.34 (dd, J=11.0 Hz, J=3.6 Hz, 2H, H-3), 5.24 (bd, J=6.5 Hz, 2H, H-4), 5.15 (d, J=3.4 Hz, 2H, H-1), 5.17 (dd, J=3.4 Hz, J=11.0 Hz, 2H, H-2), 4.80 (d, J=11.2 Hz, 2H, H-7a), 4.62 (d, J=11.2 Hz, 2H, H-7b), 4.53 (t, J=4.8 Hz, 4H, H-11), 4.20 (br q, J=6.5 Hz, 2H, H-5), 3.87 (t, J=4.8 Hz, 4H, H-10), 3.68-3.50 (m, 24H, CH$_2$O), 2.15, 2.01, 1.90 (3 s, 18H; COCH$_3$), 1.13 (d, J=6.3 Hz, 6H, H-6).

$^{13}$C NMR (75 MHz, CDCl$_3$): δ (ppm): 170.7, 170.6, 170.1 (3 COCH$_3$), 142.8 (C-8), 124.2 (C-9), 95.5 (C-1), 71.2 (C-4), 70.9-70.2 (CH$_2$O), 69.5 (C-10), 68.2 (C-2), 68.1 (C-3), 64.7 (C-5), 50.3 (C-7), 21.0, 20.7, 20.6 (3 COCH$_3$), 15.7 (C-6).

HRMS, MALDI: m/z: [M+H]$^+_{calc}$=1077.4727 Da, [M+H]$^+_{mes}$=1077.4722 Da [α]$_D$(CHCl$_3$, c=1, 20° C.)=−12.6

Example 20: Compound 18

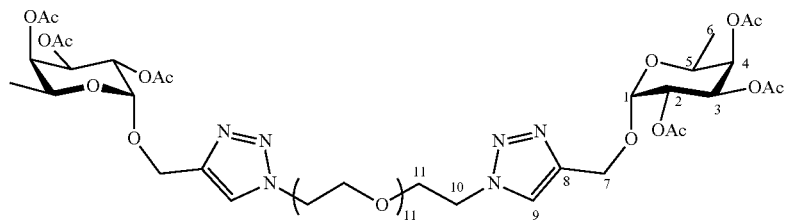

Obtained following the CuAAC method G3 of Example 4. The crude product was chromatographed on a silica gel column with 95/5 (DCM/MeOH) as eluent to afford 18 (78% yield) as a colorless oil.

$^1$H NMR (300 MHz, CDCl$_3$): δ (ppm): 5.31 (dd, J=11.0 Hz, J=3.6 Hz, 2H, H-3), 5.24 (bd, J=6.5 Hz, 2H, H-4), 5.15 (d, J=3.4 Hz, 2H, H-1), 5.12 (dd, J=3.4 Hz, J=11.0 Hz, 4H, H-2), 4.84 (d, J=11.2 Hz, 2H, H-7a), 4.62 (d, J=11.2 Hz, 2H, H-7b), 4.53 (t, J=4.8 Hz, 2H, H-11), 4.21 (br q, J=6.5 Hz, 2H, H-5), 3.88-3.36 (m, 42H, H-10, CH$_2$O), 2.14, 2.01, 1.90 (3 s, 18H; COCH$_3$), 1.12 (d, J=6.3 Hz, 6H, H-6).

$^{13}$C NMR (75 MHz, CDCl$_3$): δ (ppm): 170.8, 170.6, 170.0 (3 COCH$_3$), 142.7 (C-8), 124.3 (C-9), 95.5 (C-1), 71.2 (C-4), 70.9-70.0 (CH$_2$O), 69.4 (C-10), 68.2 (C-2), 68.1 (C-3), 64.6 (C-5), 50.4 (C-7), 21.0, 20.7, 20.5 (3 COCH$_3$), 15.5 (C-6).

HRMS, MALDI: m/z: [M+H]$^+_{calc}$=1253.5776 Da, [M+H]$^+_{mes}$=1253.5779 Da

[α]$_D$ (CHCl$_3$, c=1, 20° C.)=−15.5

Example 21: Compound 19

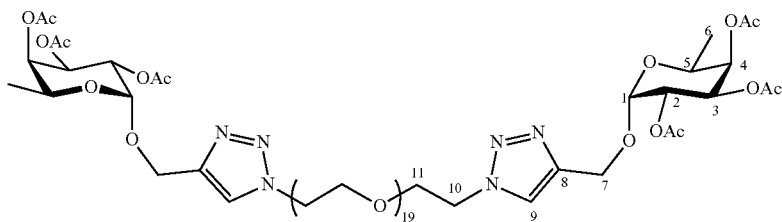

Obtained following the CuAAC method G3 of Example 4. The crude product was chromatographed on a silica gel column with 95/5 (DCM/MeOH) as eluent to afford 19 (79% yield) as a white solid.

$^1$H NMR (300 MHz, CDCl$_3$): δ (ppm): 5.33 (dd, J=11.0 Hz, J=3.6 Hz, 2H, H-3), 5.26 (bd, J=6.5 Hz, 2H, H-4), 5.15 (d, J=3.4 Hz, 2H, H-1), 5.11 (dd, J=3.4 Hz, J=11.0 Hz, 2H, H-2), 4.87 (d, J=11.2 Hz, 2H, H-7a), 4.60 (d, J=11.2 Hz, 2H, H-7b), 4.55 (t, J=4.8 Hz, 2H, H-1), 4.22 (br q, J=6.5 Hz, 2H, H-5), 3.85-3.35 (m, 74H, H-10, CH$_2$O), 2.15, 2.01, 1.91 (3 s, 18H; COCH$_3$), 1.14 (d, J=6.3 Hz, 6H, H-6)

$^{13}$C NMR (75 MHz, CDCl$_3$): δ (ppm): 170.7, 170.6, 170.1 (3 COCH$_3$), 142.5 (C-8), 124.2 (C-9), 95.4 (C-1), 71.1 (C-4), 71.1-70.1 (CH$_2$O), 69.4 (C-10), 68.3 (C-2), 68.0 (C-3), 64.7 (C-5), 50.4 (C-7), 21.1, 20.7, 20.5 (3 COCH$_3$), 15.3 (C-6)

HRMS, MALDI: m/z: [M+H]$^+_{calc}$=1605.7873 Da, [M+H]$^+_{mes}$=1605.7869 Da

[α]$_D$ (CHCl$_3$, c=1, 20° C.)=−17.3

Example 22: Compound 20

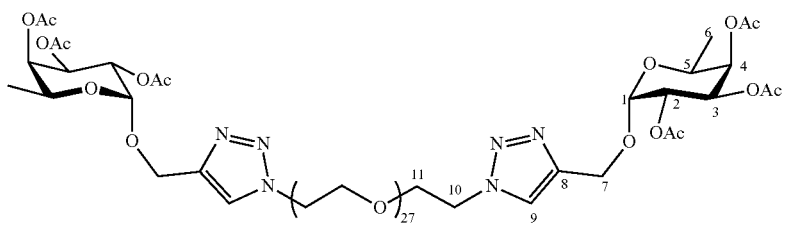

Obtained following the CuAAC method G3 of Example 4. The crude product was chromatographed on a silica gel column with 95/5 (DCM/MeOH) as eluent to afford 20 (74% yield) as a white solid.

$^1$H NMR (300 MHz, CDCl$_3$): δ (ppm): 5.32 (dd, J=11.0 Hz, J=3.6 Hz, 2H, H-3), 5.25 (bd, J=6.5 Hz, 2H, H-4), 5.16 (d, J=3.4 Hz, 2H, H-1), 5.12 (dd, J=3.4 Hz, J=11.0 Hz, 2H, H-2), 4.85 (d, J=11.2 Hz, 2H, H-7a), 4.61 (d, J=11.2 Hz, 2H, H-7b), 4.54 (t, J=4.8 Hz, 4H, H-11), 4.21 (br q, J=6.5 Hz, 2H, H-5), 3.90-3.35 (m, 104H, H-10, CH$_2$O), 2.14, 2.01, 1.90 (3 s, 18H; COCH$_3$), 1.13 (d, J=6.3 Hz, 6H, H-6)

$^{13}$C NMR (75 MHz, CDCl$_3$): δ (ppm): 170.7, 170.6, 170.1 (3 COCH$_3$), 142.5 (C-8), 124.2 (C-9), 95.4 (C-1), 71.1 (C-4), 71.1-70.1 (CH$_2$O), 69.4 (C-10), 68.3 (C-2), 68.0 (C-3), 64.7 (C-5), 50.4 (C-7), 21.1, 20.7, 20.5 (3 COCH$_3$), 15.3 (C-6)

HRMS, MALDI: m/z: [M+H]$^+_{calc}$=1957.9970 Da, [M+H]$^+_{mes}$=1957.9976 Da

[α]$_D$ (CHCl$_3$, c=1, 20° C.)=−14.2

Example 23: Compound 21

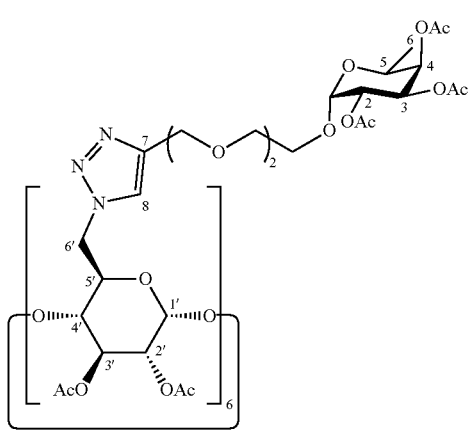

Obtained following the CuAAC method G3 of Example 4. The crude product was chromatographed on a silica gel column with 8/2 (Cyclohexane/AcOEt) as eluent to afford 21 (65% yield) as a white solid.

$^1$H NMR (400 MHz, CDCl$_3$): δ (ppm): 7.70 (bs, 6H, H-8), 5.43 (m, 6H, H-3), 5.39 (bs, 6H, H-1'), 5.30 (dd, J=2.7 Hz, J=10.5 Hz, 6H, H-2), 5.20 (bd, J=6.5 Hz, 6H, H-4), 5.02 (t, J=9.1 Hz, 6H, H-3'), 5.01 (bs, 6H, H-1), 4.70-4.30 (m, 30H, H-2', H-4', H-5', H6'), 4.15 (m, 6H, H-5), 3.56 (m, 60H, CH$_2$O), 2.20-1.80 (5 bs, 90H, CH$_3$CO), 1.05 (d, J=6.0 Hz, 18H, H-6).

$^{13}$C NMR (100 MHz, CDCl$_3$): δ (ppm): 170.8-169.2 (CH$_3$CO), 144.8 (C-7), 125.6 (C-8), 96.3 (C-1'), 71.2 (C-2), 70.5 (C-3), 70.2-69.0 (CH), 68.2-68.1 (CH$_2$O), 67.5 (CH$_2$O), 64.5 (C-5), 64.3 (CH), 20.9-20.5 (CH$_3$CO), 15.9 (C-6)

HRMS, MALDI: m/z: [M+3H]$^{3+}_{calc}$=1375.8396 Da, [M+3H]$^{3+}_{mes}$=1375.8390 Da

[α]$_D$ (CHCl$_3$, c=0.7, 20° C.)=−24.6

Example 24: Compound 22

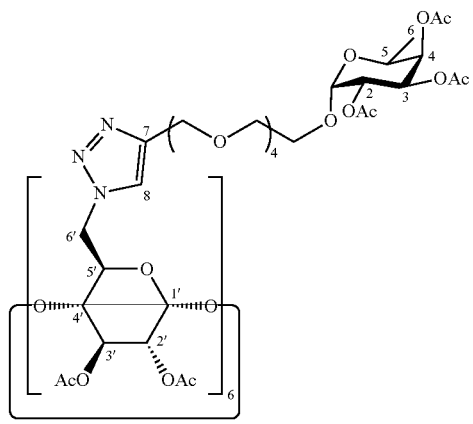

Obtained following the CuAAC method G3 of Example 4. The crude product was chromatographed on a silica gel column with 8/2 (Cyclohexane/AcOEt) as eluent to afford 22 (65% yield) as a white solid.

$^1$H NMR (400 MHz, CDCl$_3$): δ (ppm): 7.72 (bs, 6H, H-8), 5.40 (m, 6H, H-3), 5.38 (bs, 6H, H-1'), 5.31 (dd, J=2.7 Hz, J=10.5 Hz, 6H, H-2), 5.22 (bd, J=6.5 Hz, 6H, H-4), 5.02 (t, J=9.1 Hz, 6H, H-3'), 5.04 (bs, 6H, H-1), 4.70-4.30 (m, 30H, H-2', H-4', H-5', H6'), 4.16 (m, 6H, H-5), 3.54 (m, 108H, CH$_2$O), 2.20-1.80 (m, 90H, CH$_3$CO), 1.07 (d, J=6.0 Hz, 18H, H-6).

$^{13}$C NMR (100 MHz, CDCl$_3$): δ (ppm): 170.8-169.2 (CH$_3$CO), 144.7 (C-7), 125.5 (C-8), 96.3 (C-1'), 71.3 (C-2), 70.6 (C-3), 70.3-69.0 (CH), 68.3-68.1 (CH$_2$O), 67.4 (CH$_2$O), 64.5 (C-5), 64.3 (CH), 20.9-20.5 (CH$_3$CO), 15.9 (C-6)

HRMS, MALDI: m/z: [M+3H]$^{3+}_{calc}$=1552.2789 Da, [M+3H]$^{3+}_{mes}$=1552.2793 Da

[α]$_D$ (CHCl$_3$, c=0.5, 20° C.)=−20.9

Example 25: Compound 23

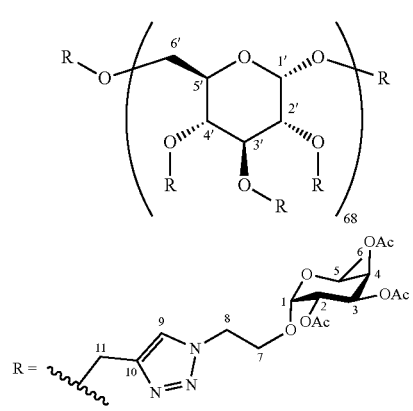

Obtained following the CuAAC method G3 of Example 4. The residue was dissolved in a small amount of CH$_2$Cl$_2$ and the product was precipitated by adding Et$_2$O (50 mL). The precipitate was collected by filtration, washed with Et$_2$O (50 mL), and precipitate twice from Et$_2$O to give 23 (63% yield) as a white solid.

¹H NMR (500 MHz, CDCl₃): δ (ppm): 8.30-7.51 (m broad, 3H, H-9), 5.30-5.22 (m broad, 6H, H-3, H-4) 4.80-4.49 (m broad, 13H, H-1, H-2, H-11, H-1'), 4.25-3.80 (m broad, 15H, H-5, H-8, H-7), 3.86-3.30 (m broad, 6H, H-2', 3',4',5',6'), 2.15-1.80 (m, 18H, CH₃CO), 1.22 (bs, 9H, H-6).

¹³C NMR (125 MHz, CDCl₃): δ (ppm): 170.7, 170.0, 169.8 (CH₃CO), 145.4 (C-10), 124.4 (C-9), 97.7 (C-1), 97.6 (C-1'), 77.3 (C-3'), 77.2 (C-4'), 70.7 (C-2'), 69.3 (C-4, C-5'), 66.4 (C-2), 65.9 (C-3), 62.3 (C-5), 60.5 (C-7), 60.1 (C-6'), 49.7 (C-8), 20.8-20-6 (3×CH₃CO), 14.3 (C-6).

Example 26: Compound 24 of Formula [A2-4-B2-C1]

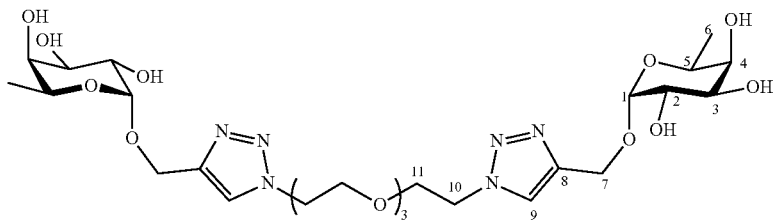

Obtained following the acetate deprotection method G5 of Example 6. This reaction afforded the compound 24 (quant. yield) as a white solid.

¹H NMR (500 MHz, CDCl₃): δ (ppm): 8.09 (s, 1H, H-9), 4.94 (bs, 1H, H-1), 4.89 (d, J=12.5 Hz, 1H, H-7a), 4.79 (d, J=12.5 Hz, 1H, H-7b) 4.60 (t, J=5.1 Hz, 2H, H-10), 3.95 (q, J=6.7 Hz, 1H, H-5), 3.89 (t, J=5.1 Hz, 2H, H-11), 3.75 (bd, 1H, J=0.9 Hz, H-2), 3.69-3.50 (m, 14H, H-3, H-4, CH₂O), 1.20 (d, J=6.6 Hz, 3H, H-6).

¹³C NMR (125 MHz, CDCl₃): δ (ppm): 145.5 (C-8) 126.0 (C-9), 100.2 (C-1), 73.7 (C-3), 73.6-71.4 (CH₂O), 70.4 (C-11), 69.0 (C-2), 67.8 (C-5), 62.2 (C-4), 61.7 (C-7), 51.4 (C-10), 16.6 (C-6).

[α]$_D$ (MeOH, c=1, 20° C.)=−66.6

HRMS, ESI: m/z: [M+H]⁺$_{calc}$=649.3045 Da, [M+H]⁺$_{mes}$=649.3041 Da

Example 27: Compound 25 of Formula [A2-5-B2-C]

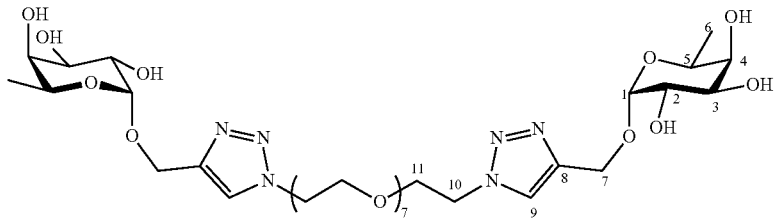

Obtained following the acetate deprotection method G5 of Example 6. This reaction afforded the compound 25 (quant. yield) as a white solid.

¹H NMR (500 MHz, CDCl₃): δ (ppm): 8.09 (s, 1H, H-9), 4.94 (bs, 1H, H-1), 4.89 (d, J=12.5 Hz, 1H, H-7a), 4.79 (d, J=12.5 Hz, 1H, H-7b) 4.60 (t, J=5.1 Hz, 2H, H-10), 3.95 (q, J=6.7 Hz, 1H, H-5), 3.89 (t, J=5.1 Hz, 2H, H-11), 3.75 (bd, 1H, J=0.9 Hz, H-2), 3.69-3.50 (m, 14H, H-3, H-4, CH₂O), 1.20 (d, J=6.6 Hz, 3H, H-6).

¹³C NMR (125 MHz, CDCl₃): δ (ppm): 145.5 (C-8) 126.0 (C-9), 100.2 (C-1), 73.7 (C-3), 73.6-71.4 (CH₂O), 70.4 (C-11), 69.0 (C-2), 67.8 (C-5), 62.2 (C-4), 61.7 (C-7), 51.4 (C-10), 16.6 (C-6).

[α]$_D$ (MeOH, c=1, 20° C.)=−49.9

HRMS, ESI: m/z: [M+H]⁺$_{calc}$=825.4093 Da, [M+H]⁺$_{mes}$=825.4092 Da

Example 28: Compound 26 of Formula
[A2-6-B2-C1]

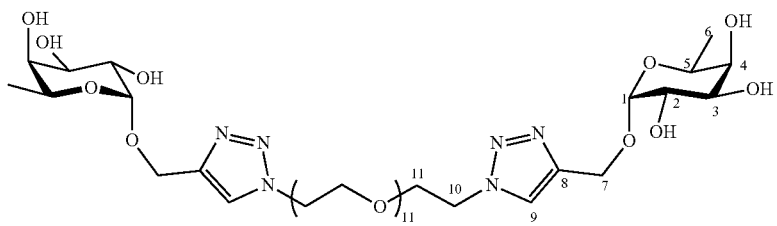

Obtained following the acetate deprotection method G5 of Example 6. This reaction afforded the compound 26 (quant. yield) as a white solid.

$^1$H NMR (500 MHz, CDCl$_3$): δ (ppm): 8.09 (s, 1H, H-9), 4.94 (bs, 1H, H-1), 4.89 (d, J=12.5 Hz, 1H, H-7a), 4.79 (d, J=12.5 Hz, 1H, H-7b) 4.60 (t, J=5.1 Hz, 2H, H-10), 3.95 (q, J=6.7 Hz, 1H, H-5), 3.89 (t, J=5.1 Hz, 2H, H-11), 3.75 (bd, 1H, J=0.9 Hz, H-2), 3.69-3.50 (m, 14H, H-3, H-4, CH$_2$O), 1.20 (d, J=6.6 Hz, 3H, H-6).

$^{13}$C NMR (125 MHz, CDCl$_3$): δ (ppm): 145.5 (C-8) 126.0 (C-9), 100.2 (C-1), 73.7 (C-3), 73.6-71.4 (CH$_2$O), 70.4 (C-11), 69.0 (C-2), 67.8 (C-5), 62.2 (C-4), 61.7 (C-7), 51.4 (C-10), 16.6 (C-6).

[α]$_D$ (MeOH, c=1, 20° C.)=−24.1

HRMS, ESI: m/z: [M+H]$^+_{calc}$=1001.5142 Da, [M+H]$^+_{mes}$=1001.5144 Da

Example 29: Compound 27 of Formula
[A2-7-B2-C1]

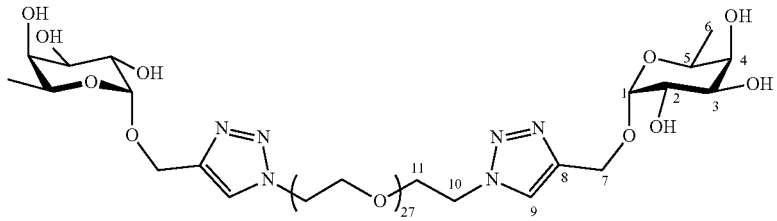

Obtained following the acetate deprotection method G5 of Example 6. This reaction afforded the compound 27 (quant. yield) as a white solid.

$^1$H NMR (500 MHz, CDCl$_3$): δ (ppm): 8.09 (s, 1H, H-9), 4.94 (bs, 1H, H-1), 4.89 (d, J=12.5 Hz, 1H, H-7a), 4.79 (d, J=12.5 Hz, 1H, H-7b) 4.60 (t, J=5.1 Hz, 2H, H-10), 3.95 (q, J=6.7 Hz, 1H, H-5), 3.89 (t, J=5.1 Hz, 2H, H-11), 3.75 (bd, 1H, J=0.9 Hz, H-2), 3.69-3.50 (m, 14H, H-3, H-4, CH$_2$O), 1.20 (d, J=6.6 Hz, 3H, H-6).

$^{13}$C NMR (125 MHz, CDCl$_3$): δ (ppm): 145.5 (C-8) 126.0 (C-9), 100.2 (C-1), 73.7 (C-3), 73.6-71.4 (CH$_2$O), 70.4 (C-11), 69.0 (C-2), 67.8 (C-5), 62.2 (C-4), 61.7 (C-7), 51.4 (C-10), 16.6 (C-6).

[α]$_D$ (MeOH, c=1, 20° C.)=−63.3

HRMS, ESI: m/z: [M+H]$^+_{calc}$=1353.7239 Da, [M+H]$^+_{mes}$=1353.7241 Da

Example 30: Compound 28 of Formula [A2-8-B2-C1]

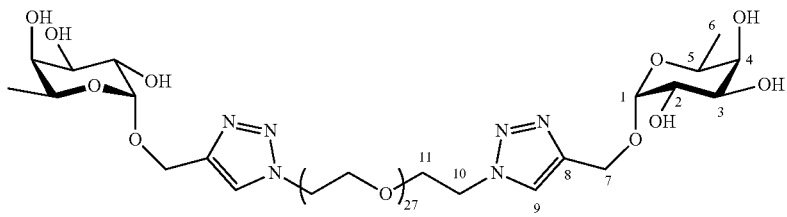

Obtained following the acetate deprotection method G5 of Example 6. This reaction afforded the compound 28 (quant. yield) as a white solid.

$^1$H NMR (300 MHz, CDCl$_3$): δ (ppm): 8.09 (s, 1H, H-9), 4.94 (bs, 1H, H-1), 4.89 (d, J=12.5 Hz, 1H, H-7a), 4.79 (d, J=12.5 Hz, 1H, H-7b) 4.60 (t, J=5.1 Hz, 2H, H-10), 3.95 (q, J=6.7 Hz, 1H, H-5), 3.89 (t, J=5.1 Hz, 2H, H-11), 3.75 (bd, 1H, J=0.9 Hz, H-2), 3.69-3.50 (m, 14H, H-3, H-4, CH$_2$O), 1.20 (d, J=6.6 Hz, 3H, H-6).

$^{13}$C NMR (75 MHz, CDCl$_3$): δ (ppm): 145.5 (C-8) 126.0 (C-9), 100.2 (C-1), 73.7 (C-3), 73.6-71.4 (CH$_2$O), 70.4 (C-11), 69.0 (C-2), 67.8 (C-5), 62.2 (C-4), 61.7 (C-7), 51.4 (C-10), 16.6 (C-6).

[α]$_D$ (MeOH, c=1, 20° C.)=−55.9

Example 31: Compound 29 of formula [A1-1-B2-C2-1]

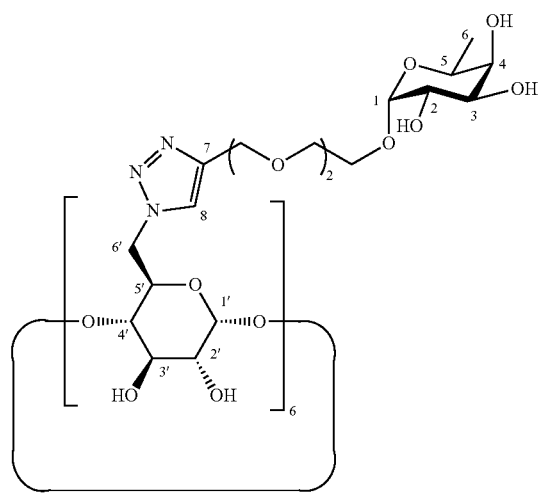

Obtained following the acetate deprotection method G6 of Example 7. This reaction afforded the compound 29 (quant. yield) as a white solid.

$^1$H NMR (400 MHz, CDCl$_3$): δ (ppm): 8.01 (s, 6H, H-8), 5.04 (bd, J=3.2 Hz, 6H, H-1'), 4.76 (d, J=3.5 Hz, 6H, H-1), 4.37 (t, J=9.6 Hz, 12H, CH$_2$O), 4.17 (m, 12H), 3.96 (m, 12H, H-5, H-6'a), 3.77-3.39 (m, 120H), 3.24 (m, 6H, CH$_2$O), 1.15 (d, J=6.8 Hz, 18H, H-6)

$^{13}$C NMR (100 MHz, CDCl$_3$): δ (ppm): 143.9 (C-8), 126.9 (C-9), 101.3 (C-1'), 98.6 (C-1), 82.3 (CH), 72.5 (CH'), 71.8 (CH), 71.3 (CH'), 70.1 (CH'), 69.7-69.4 (CH$_2$O), 69.0 (CH'), 68.1 (CH), 66.8 (CH), 66.6 (CH$_2$O) 62.9 (C-6'), 50.4 (CH$_2$O), 15.3 (C-6).

HRMS, MALDI: m/z: [M+2H]$^{2+}_{calc}$=1705.9336 Da, [M+2H]$^{2+}_{mes}$=1705.9334 Da

[α]$_D$ (MeOH, c=1, 20° C.)=−36.5

Example 32: Compound 30 of formula [A1-1-B2-C2-2]

Obtained following the acetate deprotection method G6 of Example 7. This reaction afforded the compound 30 (quant. yield) as a white solid.

$^1$H NMR (400 MHz, CDCl$_3$): δ (ppm): 8.01 (s, 6H, H-8), 5.04 (bd, J=3.2 Hz, 6H, H-1'), 4.76 (d, J=3.5 Hz, 6H, H-1), 4.37 (t, J=9.6 Hz, 12H, CH$_2$O), 4.17 (m, 12H), 3.96 (m, 12H, H-5, H-6'a), 3.77-3.39 (m, 120H), 3.24 (m, 6H, CH$_2$O), 1.15 (d, J=6.8 Hz, 18H, H-6).

$^{13}$C NMR (100 MHz, CDCl$_3$): δ (ppm): 143.9 (C-8), 126.9 (C-9), 101.3 (C-1'), 98.6 (C-1), 82.3 (CH), 72.5 (CH'), 71.8 (CH), 71.3 (CH'), 70.1 (CH'), 69.7-69.4 (CH$_2$O), 69.0 (CH'), 68.1 (CH), 66.8 (CH), 66.6 (CH$_2$O) 62.9 (C-6'), 50.4 (CH$_2$O), 15.3 (C-6).

HRMS, MALDI: m/z: [M+2H]$^{2+}_{calc}$=1697.2544 Da, [M+2H]$^{2+}_{mes}$=1697.2543 Da

[α]$_D$ (MeOH, c=11, 20° C.)=−33.2

Example 33: Compound 31 of Formula
[A3-1-B1-C3]

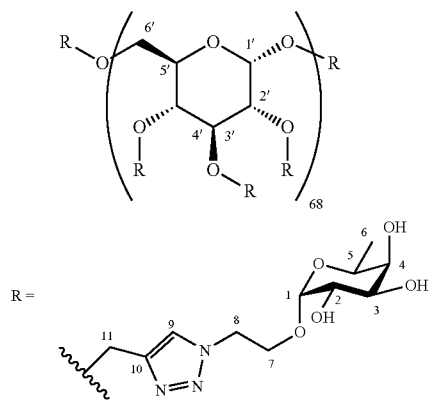

Obtained following the acetate deprotection method G6 of Example 7. This reaction afforded the compound 31 (72% yield) as a yellowish solid.

$^1$H NMR (400 MHz, CDCl$_3$): δ (ppm): 8.18-7.95 (m broad, 3H, H-9), 5.22-5.06 (m broad, 1H, H-1'), 5.03-4.81 (m broad, 9H, H-1, H-11), 4.50-4.36 (m broad, 3H, H-7), 4.05-3.69 (m broad, 11H), 3.64-3.52 (m broad, 4H), 3.49-3.36 (m broad, 3H), 3.35-3.26 (m broad, 3H), 3.07-2.95 (m broad, 3H), 2.91-2.76 (m broad, 3H), 2.76-2.60 (m broad, 3H), 2.41-2.21 (m broad, 3H), 1.55-1.30 (m broad, 3H, H-6).

$^{13}$C NMR (100 MHz, CDCl$_3$): δ (ppm): 144.4 (C-10), 125.2 (C-9), 96.1 (C-1'), 94.4 (C-1), 80.6 (CH'), 79.2 (CH'), 78.5 (CH), 77.3 (CH'), 72.7 (CH'), 70.0 (CH), 69.1 (CH), 65.5 (CH'), 65.3 (CH), 63.3 (CH$_2$), 57.6 (CH$_2$), 48.9 (CH$_2$), 24.1 (C-6).

Example 34: Compound 33

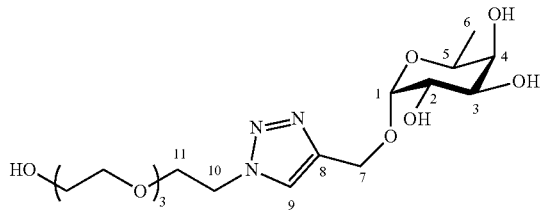

Obtained following the acetate deprotection method G5 of Example 6. This reaction afforded the compound 33 (quant. yield) as a white solid.

$^1$H NMR (300 MHz, CDCl$_3$): δ (ppm): 8.09 (s, 1H, H-9), 4.94 (bs, 1H, H-1), 4.89 (d, J=12.5 Hz, 1H, H-7a), 4.79 (d, J=12.5 Hz, 1H, H-7b) 4.60 (t, J=5.1 Hz, 2H, H-10), 3.95 (q, J=6.7 Hz, 1H, H-5), 3.89 (t, J=5.1 Hz, 2H, H-11), 3.75 (bd, 1H, J=0.9 Hz, H-2), 3.69-3.50 (m, 14H, H-3, H-4, CH$_2$O), 1.20 (d, J=6.6 Hz, 3H, H-6).

$^{13}$C NMR (75 MHz, CDCl$_3$): δ (ppm): 145.5 (C-8) 126.0 (C-9), 100.2 (C-1), 73.7 (C-3), 73.6-71.4 (CH$_2$O), 70.4 (C-11), 69.0 (C-2), 67.8 (C-5), 62.2 (C-4), 61.7 (C-7), 51.4 (C-10), 16.6 (C-6).

HRMS, ESI: m/z: [M+Na]$^+_{calc}$=356.1434 Da, [M+Na]$^+_{mes}$=356.1433 Da

[α]$_D$ (MeOH, c=1, 20° C.)=−48.7

Example 35: Compound 9

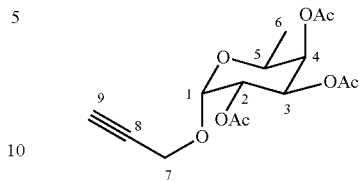

Acidic silica (8 mg) was added to a mixture of L-fucose (255 mg, 1.55 mmol, 1 eq) and propargyl alcohol (0.8 mL, 11 mmol, 7 eq). The mixture was stirred at 80° C. for 16 hours, filtered, and concentrated under reduced pressure. The residue was dissolved in a mix of acetic anhydride and pyridine (1/1, 15 mL), along with 4-dimethylaminopyridine (19 mg, 0.16 mmol, 0.1 eq). The mixture was stirred for 12 h at r.t., concentrated under reduced pressure, dissolved in dichloromethane, washed with aqueous NaHCO$_{3sat}$, dried over MgSO$_4$, filtered and concentrated under reduced pressure. The residue was purified on silica gel (Petroleum ether/Ethyl acetate 8:2) to yield compound 9 (242 mg, 47%) as a yellow oil.

[α]$_D$ (CHCl$_3$, c=1, 20° C.)=−147.5; $^1$H NMR (400 MHz, CDCl$_3$) d: 5.36 (1H, dd, J$_{3-4}$=3.4 Hz, J$_{3-2}$=10.8 Hz, H-3), 5.30 (1H, dd, J$_{4-5}$=1.2 Hz, H-4), 5.25 (1H, d, J$_{2-1}$=3.8 Hz, H-1), 5.15 (1H, dd, H-2), 4.25 (2H, d, J$_{7-9}$=2.4 Hz, H-7), 4.19 (1H, qd, J$_{5-6}$=6.6 Hz, H-5), 2.42 (1H, t, H-9), 2.16, 2.08, 1.98 (9H, 3s, COCH$_3$), 1.14 (3H, d, H-6); $^{13}$C NMR (100 MHz, CDCl$_3$) d: 170.7, 170.5, 170.1 (COCH$_3$), 95.24 (C-1), 78.75 (C-8), 74.93 (C-9), 71.27 (C-4), 67.99 (C-2), 65.17 (C-5), 55.37 (C-7), 20.92, 20.80, 20.76 (COCH$_3$), 15.90 (C-6); HRMS (ES+) m/z calcd for C$_{15}$H$_{20}$O$_8$Na [M+Na]$^+_{calc}$: 351.1056, found 351.1048.

Example 36: Compound 34

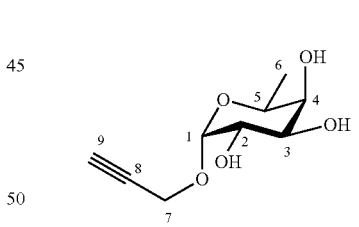

Compound 9 (32.5 mg, 0.099 mmol) was placed in MeOH (3 mL) with lithium hydroxide (1.2 mg, 0.05 mmol, 0.5 eq) and stirred for 1 hour. Water (1 mL) was added and the mixture stirred for another 30 minutes. Dowex-50 resin was added until pH reached 7. The mixture was filtered through fritted funnel and concentrated under reduced pressure to yield the deacetylated compound 34 in quantitative yield (20 mg).

$^1$H NMR (400 MHz, MeOD$_4$) d: 4.94 (1H, d, J$_{1-2}$=3.4 Hz, H-1), 4.26 (2H, d, J$_{9-7}$=2.0 Hz, H-7), 3.97 (1H, q, J$_{5-6}$=6.4 Hz, H-5), 3.76 (1H, dd, J$_{2-3}$=10.1 Hz, H-2), 3.72 (1H, dd, J$_{3-4}$=2.9 Hz, H-3), 3.67 (1H, dd, J$_{4-5}$=1.2 Hz, H-4), 2.83 (1H, t, H-9), 1.22 (3H, d, H-6); $^{13}$C NMR (100 MHz, MeOD$_4$) d: 99.3 (C-1), 80.3 (C-9), 75.8 (C-8), 73.6 (C-4), 71.6 (C-2), 69.8 (C-3), 68.0 (C-5), 55.6 (C-7), 16.5 (C-6); HRMS (ES+) m/z calcd for $C_9H_{14}O_5Na$ $[M+Na]^+_{calc}$: 225.0739, found 225.0737.

Example 37: Compound 14

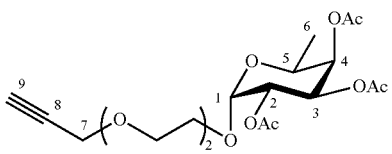

Acidic silica (15 mg) was added to a mixture of L-fucose (500 mg, 3.05 mmol, 1 eq) and diethylene glycol propargyl ether (1.32 g, 9.18 mmol, 3 eq). The mixture was stirred at 80° C. for 16 hours, filtered, and concentrated under reduced pressure. The residue was purified on silica gel (dichloromethane/methanol 95:5) to remove remaining alcohol. The mix of a/b anomers was dissolved in acetic anhydride and pyridine (1/1, 30 mL), along with 4-dimethylaminopyridine (36 mg, 0.30 mmol, 0.1 eq). The mixture was stirred for 12 h at r.t., concentrated under reduced pressure, dissolved in dichloromethane, washed with aqueous $NaHCO_{3sat}$, dried over $MgSO_4$, filtered and concentrated under reduced pressure. The residue was purified on silica gel (Petroleum ether/Ethyl acetate 6:4) to yield compound 14 (372 mg, 29%) as a yellow oil.

$[\alpha]_D$ ($CHCl_3$, c=1, 20° C.)=−109.5; $^1H$ NMR (400 MHz, $CDCl_3$) d: 5.33 (1H, dd, $J_{3-4}$=3.4 Hz, $J_{3-2}$=10.0 Hz, H-3), 5.26 (1H, dd, $J_{4-5}$=1.2 Hz, H-4), 5.13-5.05 (2H, m, H-1, H-2), 4.20 (3H, qd, $J_{5-6}$=6.6 Hz, H-5), 4.17 (2H, d, $J_{9-7}$=2.4 Hz, H-7), 3.82-3.59 (8H, m, $CH_2$), 2.42 (1H, t, H-9), 2.12, 2.03, 1.94 (9H, 3s, $COCH_3$), 1.10 (3H, d, $J_{5-6}$=6.6 Hz, H-6); $^{13}C$ NMR (100 MHz, $CDCl_3$) d: 170.7, 170.5, 170.1 (3 $COCH_3$), 96.3 (C-1), 79.7 (C-8), 74.7 (C-9), 71.3 (C-4), 70.6 ($CH_2$), 70.2 ($CH_2$), 69.2 ($CH_2$), 68.3 (C-2), 68.1 (C-3), 67.6 ($CH_2$), 64.4 (C-5), 58.5 (C-7), 20.9, 20.74, 20.69 (3s, 3C, $COCH_3$), 15.9 (C-6); HRMS (ES+) m/z calcd for $C_{19}H_{28}O_{10}Na$ $[M+Na]^+_{calc}$: 439.1580, found 439.1586.

Example 38: Compound 35

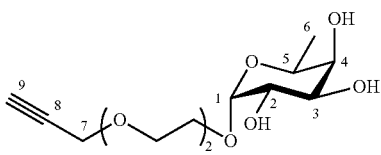

Compound 14 (28.7 mg, 0.069 mmol) was placed in MeOH (3 mL) with lithium hydroxide (0.8 mg, 0.03 mmol, 0.5 eq) and stirred for 1 hour. Water (1 mL) was added and the mixture stirred for another 30 minutes. Dowex-50 resin was added until pH reached 7. The mixture was filtered through fritted funnel and concentrated under reduced pressure to yield the deacetylated compound 35 in quantitative yield (20 mg).

$^1H$ NMR (400 MHz, $MeOD_4$) d: 4.78 (1H, m, H-1), 4.19 (2H, m, H-7), 4.02 (1H, q, H-5), 3.83-3.76 (1H, m, H-3), 3.76-3.70 (2H, m, H-2, H-4), 3.70-3.58 (8H, m, $CH_2O$), 1.21 (3H, d, H-6); $^{13}C$ NMR (100 MHz, $MeOD_4$) d: 100.7 (C-1), 71.7 (C-4), 71.4 ($CH_2$), 70.1 (C-2), 70.0 ($CH_2$), 68.2 (H-3), 67.6 (H-5), 59.0 (C-7), 16.6 (C-6); HRMS (ES+) m/z calcd for $C_{13}H_{20}O_7Na$ $[M+Na]^+_{calc}$: 313.1263, found 313.1266.

Example 39: Compound 15

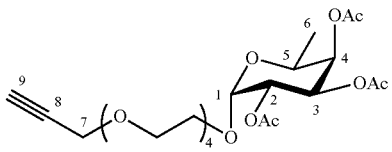

Acidic silica (30 mg) was added to a mixture of L-fucose (1 mg, 6.10 mmol, 1 eq) and tetraethylene glycol propargyl ether (4.24 g, 18.58 mmol, 3 eq). The mixture was stirred at 80° C. for 16 hours, filtered, and concentrated under reduced pressure. The residue was purified on silica gel (dichloromethane/methanol 95:5) to remove remaining alcohol. The mix of a/b anomers was dissolved in acetic anhydride and pyridine (1/1, 60 mL), along with 4-dimethylaminopyridine (72 mg, 0.60 mmol, 0.1 eq). The mixture was stirred for 12 h at r.t., concentrated under reduced pressure, dissolved in dichloromethane, washed with aqueous $NaHCO_3$, dried over $MgSO_4$, filtered and concentrated under reduced pressure. The residue was purified on silica gel (Petroleum ether/Ethyl acetate 5:5) to yield compound 1 (381 mg, 12%) as a yellow oil.

$[\alpha]_D$ ($CHCl_3$, c=1, 20° C.)=−53.5; $^1H$ NMR (400 MHz, $CDCl_3$) d: 5.36-5.28 (1H, m, H-3), 5.25 (1H, dd, $J_{4-5}$=1.2 Hz, $J_{4-3}$=3.4 Hz, H-4), 5.11-5.02 (2H, m, H-1, H-2), 4.24-4.13 (3H, m, H-7, H-5), 3.69-3.57 (16H, m, $CH_2$), 2.41 (1H, t, $J_{7-9}$=2.4 Hz, H-9), 2.12, 2.03, 1.94 (9H, 3s, $CH_3CO$), 1.09 (3H, d, $J_{5-6}$=6.6 Hz, H-6); $^{13}C$ NMR (100 MHz, $CDCl_3$) d: 170.7, 170.5, 170.1 (3 $COCH_3$), 96.3 (C-1), 79.7 (C-8), 74.6 (C-9), 71.3 (C-4), 70.8 ($CH_2$), 70.7 ($CH_2$), 70.4 ($CH_2$), 70.2 ($CH_2$), 69.1 ($CH_2$), 68.2 (C-2) 68.1 (C-3), 67.2 ($CH_2$), 64.3 (C-5), 58.4 (C-7), 20.9, 20.8, 20.7 (3 $COCH_3$), 15.9 (C-6); HRMS (ES+) m/z calcd for $C_{23}H_{36}O_{12}Na$ $[M+Na]^+_{calc}$: 527.2104, found 527.2114.

Example 40: Compound 36

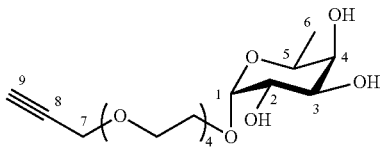

Compound 15 (26.7 mg, 0.053 mmol) was placed in MeOH (3 mL) with lithium hydroxide (0.6 mg, 0.03 mmol, 0.5 eq) and stirred for 1 hour. Water (1 mL) was added and the mixture stirred for another 30 minutes. Dowex-50 resin was added until pH reached 7. The mixture was filtered through fritted funnel and concentrated under reduced pressure to yield the deacetylated compound 36 in quantitative yield (20 mg).

$[\alpha]_D$ (MeOH, c=0.5, 20° C.)=−139.8; $^1H$ NMR (400 MHz, $MeOD_4$) d: 4.79 (1H, d, $J_{1-2}$=3.3 Hz, H-1), 4.19 (2H, d, $J_{7-9}$=2.4 Hz, H-7), 4.01 (1H, q, $J_{5-6}$=6.3 Hz, H-5), 3.85-3.76 (1H, m, H-4), 3.76-3.58 (18H, m, $CH_2$, H-2, H-3), 2.85 (1H, t, H-9), 1.21 (3H, d, H-6); $^{13}C$ NMR (100 MHz, $MeOD_4$) d: 100.7 (C-1), 80.6 (C-9), 75.9 (C-8), 73.6 (C-4), 71.7 (C-2), 71.5 (CH$_2$), 71.3 (CH$_2$), 70.12 (C-3), 70.10 (CH$_2$), 68.2 (CH$_2$), 67.6 (C-5), 59.0 (C-7), 16.7 (C-6); HRMS (ES+) m/z calcd for C$_{17}$H$_{30}$O$_9$Na [M+Na]$^+$$_{calc}$: 401.1788, found 401.1777.

Example 41: Compound 37

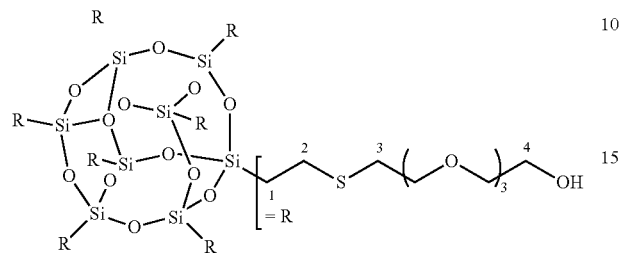

Commercial POSS-octavinyl 10 (100 mg, 0.16 mmol, 1 eq) was placed in DMF/THF (2/1 3 mL) with 1-mercapto-11-hydroxy-3,6,9-trioxaundecane (500 mg, 2.4 mmol, 15 eq) and DPAP (20 mg, 0.008 mmol, 0.5 eq). The reaction was photo-activated (365 nm) and stirred for 1 hour. The crude product was purified by Sephadex LH-20 to yield compound 37 (327 mg, 89%).

$^1$H NMR (MeOD$_4$, 300 MHz) d: 3.70-3.61 (96H, m, CH$_2$O), 3.61-3.55 (16H, m, H-4), 2.80-2.65 (32H, m, H-2, H-3), 1.15-1.00 (16H, t, J$_{1-2}$=8.0 Hz, H-1); $^{13}$C NMR (MeOD$_4$, 75 MHz) d: 73.7, 72.1, 71.7, 71.6, 71.5, 71.3 (6 CH$_2$O), 62.3 (C-4), 32.3 (C-3), 27.4 (C-2), 14.0 (C-1). HRMS (ES−) m/z calcd for C$_{80}$H$_{167}$O$_{44}$Si$_8$S$_8$ [M−H]$^−$$_{calc}$: 2311.6750, found 2311.6707.

Example 41: Compound 38

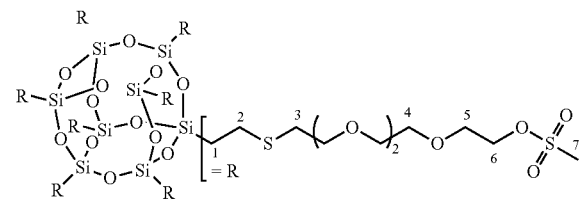

Compound 37 (669 mg, 0.289 mmol, 1 eq) was dissolved in dry DCM (20 mL). Triethylamine (0.58 mL, 4.3 mmol, 15 eq) and then, methanesulfonyl chloride (0.22 mL, 2.89 mmol, 10 eq), were added and the mixture was stirred for 48 hours at r.t. The mixture was concentrated under reduced pressure, dissolved in ethyl acetate (20 mL), washed with water (20 mL), brine (20 mL), water (20 mL), dried over MgSO$_4$ and concentrated under reduced pressure. The crude product was purified by Sephadex LH-20 to yield compound 38 (415 mg, 49%).

$^1$H NMR (CDCl$_3$, 400 MHz) d: 4.33 (16H, t, J$_{6-5}$=4.4 Hz, H-6), 3.73 (16H, t, H-5), 3.67-3.52 (80H, m, 4CH$_2$, H-4), 2.68 (16H, t, J$_{2-3}$=6.9 Hz, H-3), 2.58 (16H, t, J$_{1-2}$=8.6 Hz, H-2), 0.97 (16H, t, H-1); $^{13}$C NMR (CDCl$_3$, 100 MHz) d: 70.6, 70.5, 70.3, 69.4, 69.0 (5CH$_2$), 37.7 (C-7), 31.2 (C-3), 26.4 (C-2), 13.1 (C-1). HRMS (ES+) m/z calcd for C$_{88}$H$_{184}$O$_{60}$Na$_3$Si$_8$S$_8$ [M+3Na]$^{3+}$$_{calc}$: 1001.8242, found 1001.8276.

Example 42: Compound 39

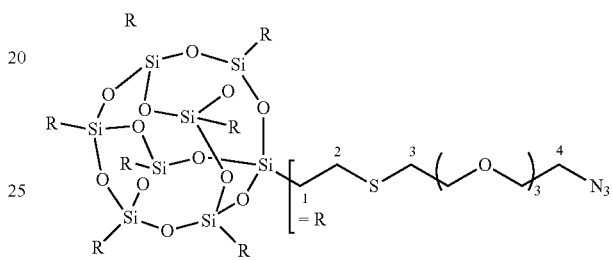

Compound 38 (415 mg, 0.14 mmol, 1 eq) was dissolved in dry DMF with sodium azide (92 mg, 1.4 mmol, 10 eq). The mixture was stirred for 48 hours at r.t., concentrated under reduced pressure and purified by Sephadex LH-20 to yield compound 39 (270 mg, 76%).

$^1$H NMR (CDCl$_3$, 400 MHz) d: 3.88-3.53 (96H, m, CH$_2$), 3.37 (16H, t, J=5.0 Hz, H-4), 2.71 (16H, t, J$_{2-3}$=6.9 Hz, H-3), 2.59 (16H, t, J$_{1-2}$=8.6 Hz, H-2), 0.99 (16H, t, H-1); $^{13}$C NMR (CDCl$_3$, 400 MHz) d: 70.7, 70.4, 70.1 (3CH$_2$O), 50.8 (C-4), 31.5 (C-3), 26.7 (C-2), 13.7 (C-1); HRMS (ES+) m/z calcd for C$_{80}$H$_{168}$N$_{26}$O$_{36}$Si$_8$S$_8$ [M+2NH$_4$]$^{2+}$$_{calc}$: 2548.8034, found 2548.7906.

Example 43: Compound 40 of Formula [A4-1-B2-C1]

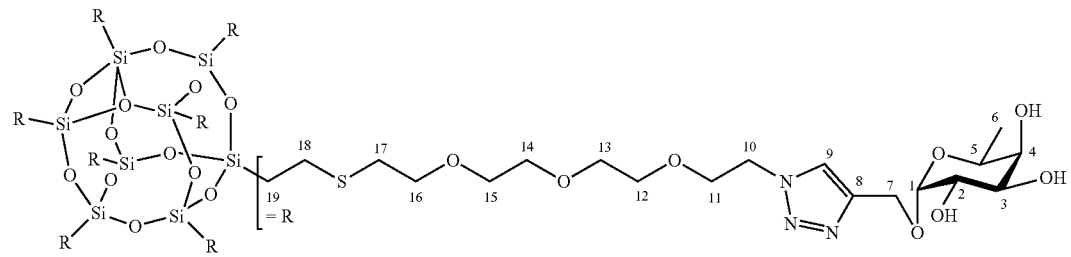

To a mix of compound 34 (62 mg, 0.307 mmol, 8.8 eq) and compound 9 (91 mg, 0.036 mmol, 1 eq) were added sodium ascorbate (4.8 eq) and copper sulfate pentahydrate (2.4 eq) and then, dioxane/water 2/1. The mixture was stirred at 60° C. for 16 hours. Quadrasil MTU was added and the mixture stirred for 30 minutes. The compound was purified on Sephadex LH-20 (MeOH/Acetone 1:1) to yield the desired cycloadduct 40.

$^1$H NMR (300 Hz, MeOD$_4$): d=8.08 (8H, bs, H-9), 4.90 (8H, m, H-1), 4.81-4.63 (16H, m, H-7), 4.59 (16H, t, J$_{10-11}$=4.4 Hz, H-10), 3.96 (8H, q, J$_{5-6}$=6.4 Hz, H-5), 3.91 (16H, t, H-11), 3.75 (16H, H-3, H-2), 3.72-3.53 (88H, m, H-12, H-13, H-14, H-15, H-16, H-4), 2.73 (32H, m, H-17, H-18), 1.20 (24H, d, H-6), 1.06 (16H, m, H-19); $^{13}$C NMR (100 Hz, MeOD$_4$): d=145.6 (C-8), 126.0 (C-9), 100.2 (C-1), 73.6 (CH$_2$), 71.9 (CH$_2$), 71.6 (C-3), 71.5 (CH$_2$), 71.4 (CH$_2$), 70.4 (C-16), 69.9 (C-2), 67.9 (C-5), 61.8 (C-7), 51.5 (C-10), 32.6 (C-17), 27.9 (C-18), 16.8 (C-6).

Example 44: Compound 41 of Formula [A4-1-B2-C2-1]

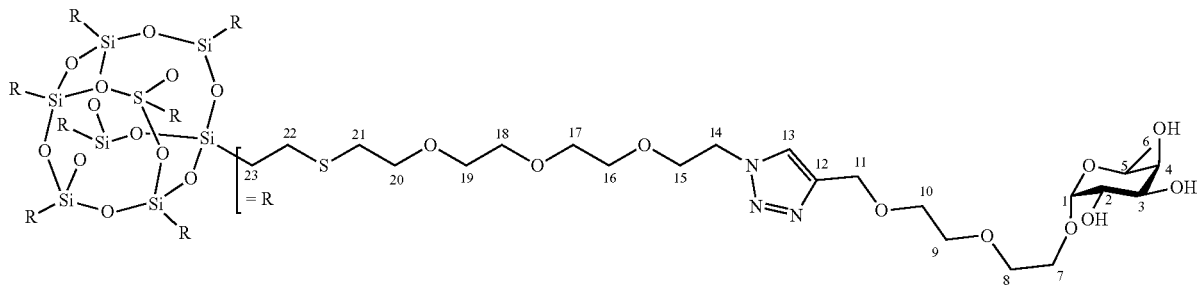

To a mix of compound 5 (66 mg, 0.227 mmol, 8.7 eq) and compound 9 (65 mg, 0.026 mmol, 1 eq) were added sodium ascorbate (25 mg, 0.126 mmol, 4.8 eq) and copper sulfate pentahydrate (16 mg, 0.064 mmol, 2.4 eq) and then, dioxane/water 2/1 (2.25 mL). The mixture was stirred at 60° C. for 16 hours. Quadrasil MTU was added and the mixture stirred for 30 minutes. The compound was purified on Sephadex LH-20 (MeOH/Acetone 1:1) to yield the desired cycloadduct 41 (77 mg, 62%).

[α]$_D$ (MeOH, c=1, 20° C.)=−43.2; $^1$H NMR (400 MHz, MeOD$_4$): d=1H: 8.07 (8H, bs, H-13), 4.79 (8H, d, H-1), 4.64 (16H, s, H-11), 4.60 (16H, t, H-14), 3.99 (8H, q, J$_{6-5}$=6.4 Hz, H-5), 3.91 (16H, t, J$_{15-14}$=4.7, H-15), 3.84-3.51 (144H, m, CH$_2$), 2.92-2.59 (32H, m, H-22, H-21), 1.19 (24H, d, H-6), 1.09 (16H, m, H-23). $^{13}$C NMR (100 MHz, MeOD$_4$): d=145.8 (C-12), 126.00 (C-13), 100.7 (C-1), 73.6 (C-3), 72.0 (CH$_2$), 71.7 (C-2), 71.5 (CH$_2$), 71.4 (CH$_2$), 70.8 (CH$_2$), 70.4 (C-15), 70.1 (C4), 68.2 (CH$_2$), 67.6 (C-5), 65.1 (C-11), 51.5 (C-14), 32.5 (C-21), 27.9 (C-22), 16.8 (C-6);

Example 45: Compound 42 of Formula [A4-1-B2-C2-2]

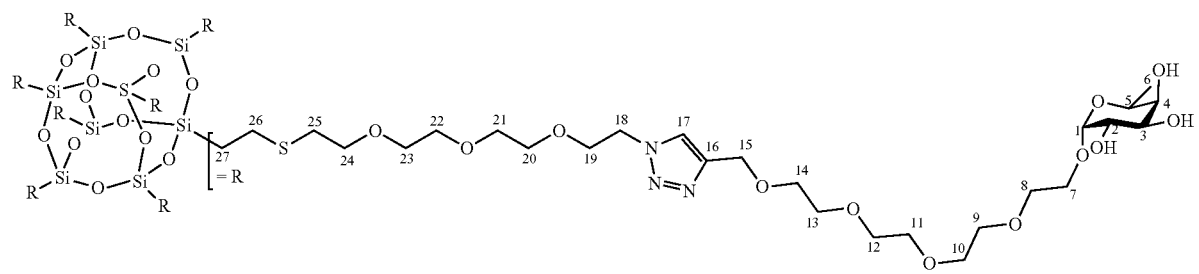

To a mix of compound 36 (73 mg, 0.193 mmol, 9.2 eq) and compound 39 (53 mg, 0.021 mmol, 1 eq) were added sodium ascorbate (21 mg, 0.106 mmol, 5.0 eq) and copper sulfate pentahydrate (13 mg, 0.052 mmol, 2.5 eq) and then, dioxane/water 2/1 (2.1 mL). The mixture was left to stir at 60° C. for 16 hours. Quadrasil MTU was added and the mixture stirred for 30 minutes. The compound was purified on Sephadex LH-20 (MeOH/Acetone 1:1) to yield the desired cycloadduct 42 (91 mg, 78%).

$[\alpha]_D$ (MeOH, c=1, 20° C.)=−45.1; $^1$H NMR (400 MHz, MeOD$_4$): d=8.07 (8H, bs, H-17), 4.79 (8H, d, $J_{1-2}$=4.8 hz, H-1), 4.64 (16H, H-15), 4.60 (16H, H-18), 4.00 (8H, q, $J_{5-6}$=6.5 hz, H-5), 3.91 (16H, H-19), 3.84-3.38 (208H, m, H-20, H-21, H-22, H-23, H-24, H-7, H-8, H-9, H-10, H-11, H-12, H-13, H-14), 2.89-2.62 (32H, m, H-25, H-26), 1.21 (24H, d, H-6), 1.17-0.98 (16H, H-27); $^{13}$C NMR (100 MHz, MeOD$_4$): d=146.0 (C-16), 126.0 (C-17), 100.7 (C-1), 73.6 (C-3), 71.9 (CH$_2$), 71.7 (C-2), 71.6 (CH$_2$), 71.4 (CH$_2$), 70.8 (CH$_2$), 70.4 (C-19), 68.3 (CH$_2$), 67.6 (C-5), 65.1 (C-15), 51.5 (C-18), 32.6 (C-25), 27.8 (C-26), 16.8 (C-6);

Example 46: Compound 43

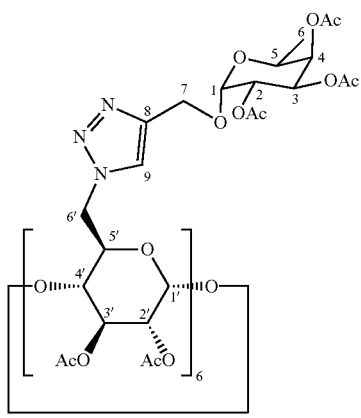

To a mix of fucoside 9 (66.6 mg, 0.203 mmol, 6.6 eq) and scaffold hexakis(6-deoxy-6-azido)-α-cyclodextrin (50 mg, 0.031 mmol, 1 eq) were added sodium ascorbate (14.6 mg, 0.074 mmol, 2.4 eq) and copper sulfate pentahydrate (9.2 mg, 0.037 mmol, 1.2 eq) and then, dioxane/water 4/1 (2.5 mL). The mixture was left to stir at 60° C. for 16 hours. Ethylenediaminetetraacetic acid was added and the mixture stirred for 20 minutes. The mixture was dissolved in ethyl acetate, washed with water, aqueous NaHCO$_{3sat}$, water, dried over MgSO$_4$, filtered and concentrated under reduced pressure. The compound was purified on silica gel (dichloromethane/MeOH 95/5) to yield the desired cycloadduct 43 (76 mg, 69%).

$[\alpha]_D$ (CHCl$_3$, c=0.5, 20° C.)=−44.6; $^1$H NMR (400 MHz, CDCl$_3$) d: 7.67 (6H, bs, H-9), 5.58-5.41 (12H, m, H-1', H-3'), 5.26 (6H, dd, $J_{3-4}$=3.2 Hz, $J_{2-3}$=10.8 Hz, H-3), 5.23-5.17 (6H, m, H-4), 5.15 (6H, d, $J_{1-2}$=3.5 Hz, H-1), 5.06 (6H, dd, $J_{2-3}$=3.6 et 10.8, H-2), 4.92-4.47 (36H, m, H-5', H-2', H-7, H-6'), 4.26-4.13 (6H, m, H-5), 3.54 (6H, dd, J=8.6 Hz, H-4'), 2.18-1.85 (90H, m, 30 COCH$_3$), 1.12 (6H, d, $J_{5-6}$=6.5 Hz, H-6); $^{13}$C NMR (100 MHz, CDCl$_3$) d: 170.6, 170.44, 170.37, 169.9, 169.2 (5 COCH$_3$), 143.9 (C-8), 125.7 (C-9), 96.7 (C-1'), 95.6 (C-1), 71.2 (C-4), 71.0 (C-3'), 70.0 (C-5', C-2'), 68.2 (C-2), 67.9 (C-3), 64.9 (C-5), 60.8 (C-6'), 50.7 (C-7), 20.8, 20.7 (COCH$_3$), 15.9 (C-6); HRMS (ES+) m/z calcd for $C_{150}H_{198}N_{18}O_{84}Na_3$ [M+3Na]$^{3+}_{calc}$: 1221.3823, found 1221.3790.

Example 47: Compound 44 of Formula [A1-1-B2-C1]

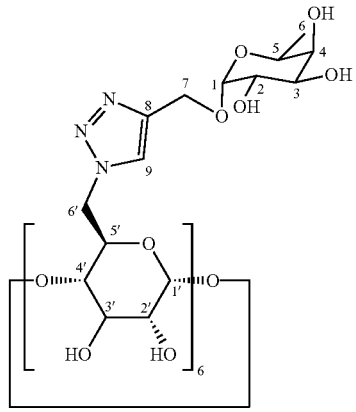

Compound 43 (66 mg, 0.018 mmol, 1 eq) was placed in MeOH (3 mL) with lithium hydroxide (0.2 mg, 0.009 mmol, 0.5 eq) and stirred for 1 hour. Water (1 mL) was added and the mixture stirred for another 30 minutes. Dowex-50 resin was added until pH reached 7. The mixture was filtered through fritted funnel and concentrated under reduced pressure to yield the deacetylated compound 44 (43 mg, quant).

$^1$H NMR (400 MHz, DMSO$_3$) d: 7.93 (6H, bs, H-9), 5.70-5.51 (10H, m, OH), 5.09 (6H, s, H-1'), 4.69 (6H, d, $J_{1-2}$=3.0 Hz, H-1), 4.55-4.41 (18H, m, 6H-6'a, 12H-7), 4.41-4.26 (24H, m, 6H-6'b, 18 OH), 4.22-4.11 (6H, m, H-5'), 3.88-3.78 (6H, m, H-3'), 3.78-3.67 (6H, m, H-5), 3.57-3.51 (6H, m, H-2), 3.50-3.45 (6H, m, H-3), 3.44-3.39 (6H, m, H-4), 3.27-3.19 (12H, m, H-2', H-4'), 1.04 (18H, d, $J_{6-5}$=6.4 Hz, H-6); $^{13}$C NMR (100 MHz, CDCl$_3$) d: 143.7 (C-8), 125.7 (C-9), 101.3 (C-1'), 98.5 (C-1), 82.6 (C-2'), 72.4 (C-3'), 71.5 (C-4), 71.3 (C-4'), 69.6 (C-5'), 68.0 (C-2), 66.0 (C-5), 60.0 (C-6'), 54.9, 49.7 (C-7), 48.6, 16.4 (C-6); $[\alpha]_D$ (H$_2$O, c=0.5, 20° C.)=−37.7; HRMS (ES+) m/z calcd for $C_{90}H_{140}N_{18}O_{54}$ [M+2H]$^{2+}_{calc}$: 1168.4381, found 1168.4329.

Example 48: Compound 21

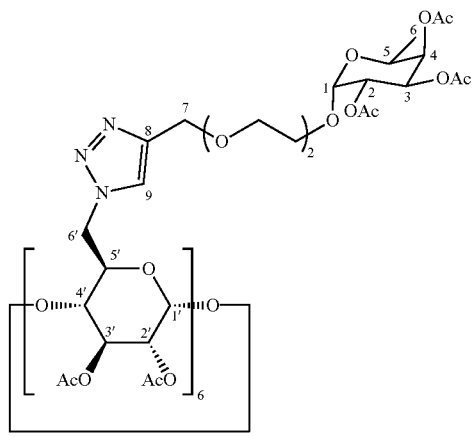

To a mix of fucoside 14 (103 mg, 0.247 mmol, 6.8 eq) and scaffold hexakis(6-deoxy-6-azido)-α-cyclodextrin_(59 mg, 0.036 mmol, 1 eq) were added sodium ascorbate (17.3 mg, 0.087 mmol, 2.4 eq) and copper sulfate pentahydrate (10.9 mg, 0.044 mmol, 1.2 eq) and then, dioxane/water 4/1 (5 mL). The mixture was left to stir at 60° C. for 16 hours. Ethylenediaminetetraacetic acid was added and the mixture stirred for 20 minutes. The mixture was dissolved in ethyl acetate, washed with water, aqueous $NaHCO_{3sat}$, water, dried over $MgSO_4$, filtered and concentrated under reduced pressure. The compound was purified on silica gel (dichloromethane/MeOH 97/3) to yield the desired cycloadduct 21 (92 mg, 61%).

$[\alpha]_D$ (CHCl$_3$, c=0.5, 20° C.)=−33.3; $^1$H NMR (400 MHz, CDCl$_3$) d: 7.67 (6H, bs, H-9), 5.56-5.43 (6H, m, H-3'), 5.39 (6H, d, $J_{1',2'}$=3.1 Hz, H-1'), 5.32 (6H, m, H-3), 5.25 (6H, dd, J=2.3 Hz, H-4), 5.10-5.04 (12H, m, H-1, H-2), 4.71 (6H, dd, $J_{2',3'}$=9.9 Hz, H-2'), 4.68-4.45 (30H, m, H-5', H-6', H-7), 4.19 (6H, q, $J_{5-6}$=6.4 Hz, H-5), 3.70-3.50 (54H, m, H-4', 24CH$_2$), 2.15-1.93 (90H, m, COCH$_3$), 1.09 (18H, d, H-6); $^{13}$C NMR (100 MHz, CDCl$_3$) d: 170.7, 170.5, 170.3, 170.1, 169.1 (5 COCH$_3$), 144.9 (C-8), 125.6 (C-9), 96.9 (C-1'), 96.4 (C-1), 71.3 (C-4), 71.1 (C-3'), 70.6, 70.2, 70.1 (3CH$_2$), 70.0 (C-2'), 68.3 (C-2), 68.2 (C-3), 67.6 (CH$_2$), 64.6 (C-6'), 64.4 (C-5), 50.6 (C-7), 20.9, 20.8, 20.7 (3 COCH$_3$), 16.0 (C-6); HRMS (ES+) m/z calcd for $C_{174}H_{249}N_{18}O_{96}$ [M+3H]$^{3+}_{calc}$: 1375.5052, found 1375.5020.

Example 49: Compound 29 of Formula [A1-1-B2-C2-1]

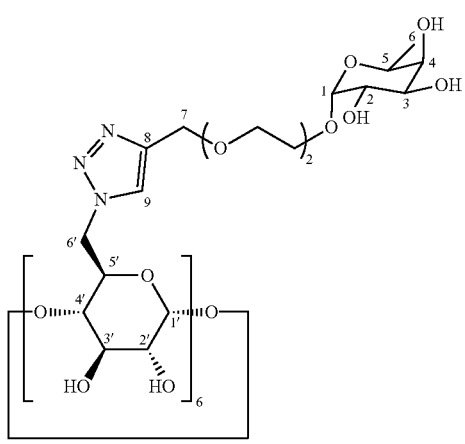

Compound 21 (122 mg, 0.030 mmol, 1 eq) was placed in MeOH (3 mL) with lithium hydroxide (0.4 mg, 0.015 mmol, 0.5 eq) and stirred for 1 hour. Water (1 mL) was added and the mixture stirred for another 30 minutes. Dowex-50 resin was added until pH reached 7. The mixture was filtered through fritted funnel and concentrated under reduced pressure to yield the deacetylated compound 29 (85 mg, quant).

$[\alpha]_D$ (MeOH, c=1, 20° C.)=−43.6; $^1$H NMR (MeOD$_4$, 300 MHz) d: 8.06 (6H, bs, H-9), 5.19 (6H, H-1'), 4.78 (6H, H-1), 4.72-4.15 (30H, m, H-3', H-4', H-5', H-6'), 4.05-3.90 (12H, m, H-5, H-3), 3.91-3.40 (78H, m, H-2', H-2, H-4, H-7, 4CH$_2$O), 1.19 (18H, d, $J_{5-6}$=6.3 Hz, H-6); $^{13}$C NMR (MeOD$_4$, 75 MHz) d: 145.7 (C-8), 127.6 (C-9), 103.1 (C-1'), 100.6 (C-1), 74.6 (C-3), 73.6 (C-4), 73.3 (C-2'), 71.7 (C-2), 71.4 (CH$_2$), 71.3 (CH$_2$), 70.9 (C-7), 70.1, 68.2 (CH$_2$), 67.6 (C-5), 64.9 (CH$_2$), 51.6 (C-6'), 16.8 (C-6); HRMS (ES+) m/z calcd for $C_{114}H_{186}N_{18}O_{66}Na_3$ [M+3 Na]$^{3+}_{calc}$: 977.3815, found 977.3844.

Example 50: Compound 22

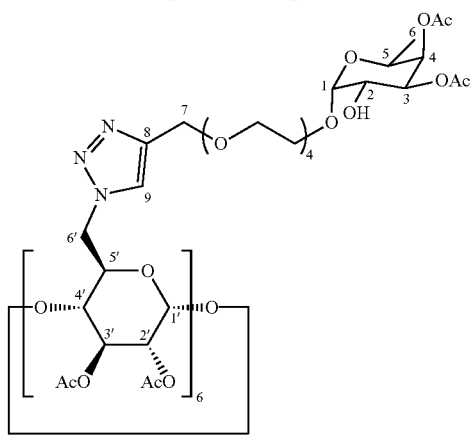

To a mix of fucoside 15 (68.3 mg, 0.135 mmol, 7.1 eq) and scaffold hexakis(6-deoxy-6-azido)-α-cyclodextrin (31.3 mg, 0.019 mmol, 1 eq) were added sodium ascorbate (9.1 mg, 0.046 mmol, 2.4 eq) and copper sulfate pentahydrate (5.8 mg, 0.023 mmol, 1.2 eq) and then, dioxane/water 4/1 (2.5 mL). The mixture was left to stir at 60° C. for 16 hours. Ethylenediaminetetraacetic acid was added and the mixture stirred for 20 minutes. The mixture was dissolved in ethyl acetate, washed with water, aqueous $NaHCO_{3sat}$, water, dried over $MgSO_4$, filtered and concentrated under reduced pressure. The compound was purified on silica gel (dichloromethane/MeOH 96/4) to yield the desired cycloadduct 22 (67 mg, 49%).

$[\alpha]_D$ (CHCl$_3$, c=0.5, 20° C.)=−26.3; $^1$H NMR (400 MHz, CDCl$_3$) d: 7.68, (6H, bs, H-9), 5.73-5.37 (12H, m, H-1', H-3'), 5.37-5.31 (6H, m, H-3), 5.29-5.24 (6H, m, H-4), 5.12-5.05 (12H, m, H-1, H-2), 4.88-4.34 (30H, m, H-2', H-5', H-6', H-7), 4.20 (6H, q, $J_{5-6}$=6.5 Hz H-5), 3.72-3.36 (102H, m, CH$_2$), 2.15-1.94 (90H, m, COCH$_3$), 1.11 (18H, d, H-6); $^{13}$C NMR (100 MHz, CDCl$_1$) d: 170.7, 170.5, 170.1 (3 COCH$_3$), 144.9 (C-8), 125.7 (C-9), 96.4 (C-1), 71.4 (C-4), 70.8, 70.7, 70.6, 70.2, 70.1 (5CH$_2$), 70.0 (C-2', C-5'), 68.3 (C-3'), 68.2 (C-3), 67.6 (CH$_2$), 64.5 (C-6'), 64.4 (C-5), 20.9, 20.8, 20.7 (3 COCH$_3$), 16.0 (C-6); HRMS (ES+) m/z calcd for $C_{198}H_{98}N_{18}O_{108}$ [M+4H]$^{4+}_{calc}$: 1163.9595, found 1163.9604.

Example 51: Compound 30 of Formula [A1-1-B2-C2-2]

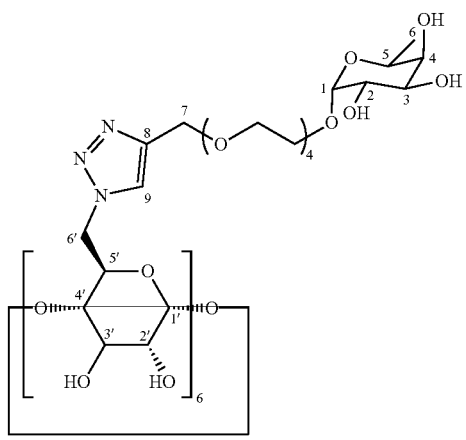

Compound 22 (71 mg, 0.015 mmol, 1 eq) was placed in MeOH (3 mL) with lithium hydroxide (0.2 mg, 0.007 mmol, 0.5 eq) and stirred for 1 hour. Water (1 mL) was added and the mixture stirred for another 30 minutes. Dowex-50 resin was added until pH reached 7. The mixture was filtered through fritted funnel and concentrated under reduced pressure to yield the deacetylated compound 21 (85 mg, quant).

$[\alpha]_D$ (MeOH, c=1, 20° C.)=−33.6; $^1$H NMR (MeOD$_4$, 300 MHz) d: 8.07 (6H, bs, H-9), 5.19 (6H, m, H-1'), 4.79 (6H, d, $J_{1-2}$=3.2 Hz, H-1), 4.72-4.12 (30H, m, H-3', H-4', H-5', H-6'), 4.07-3.92 (12H, m, H-5, H-3), 3.86-3.50 (120H, m, H-2, H-4, H-7, 8CH$_2$O), 3.71-3.41 (6H, m, H-2'), 1.20 (18H, d, $J_{5-6}$=6.5 Hz); $^{13}$C NMR (MeOD$_4$, 75 MHz) d: 145.7 (C-8), 127.4 (C-9), 103.1 (C-1'), 100.6 (C-1), 74.6 (C-3), 73.6 (C-4), 73.3 (C-2'), 71.7 (C-2), 71.5 (CH$_2$), 71.4 (CH$_2$), 71.3 (CH$_2$), 70.9 (CH$_2$), 70.1, 68.2 (C-7), 67.6 (C-5), 64.9 (CH$_2$), 51.6 (C-6'), 16.8 (C-6); HRMS (ES+) m/z calcd for $C_{138}H_{237}N_{18}O_{78}$ $[M+3H]^{3+}_{calc}$: 1131.5044, found 1131.5072.

Example 52: Fischer Glycosylation and Acetylation[1] G10:

Acidic silica (5 mg/mmol) was added to a mixture of L-Fucose (1 eq) and acceptor alcohol propargyl (3 eq). The mixture was heated to 70° C. overnight, filtered through cotton and concentrated under reduced pressure. The residue was purified on silica gel (dichloromethane/methanol) to eliminate acceptor alcohol. The mix α/β anomers was dissolved in dichlorometane and acetic anhydride (6 eq), TEA (6 eq) and DMAP (0.1 eq) were added at 0° C. The mixture was stirred 12 h at room temperature, concentrated under reduced pressure, dissolved in dichloromethane, washed with aqueous sat. NaHCO$_3$, dried over MgSO$_4$. The organic layers were concentrated under reduced pressure and the residue was purified on silica gel (Petroleum Ether/Ethyl Acetate) to isolate the desired fucoside.

[1] H. Hashimoto, K. Shimada, S. Horito, *Tetrahedron-Asymmetr.* 1994, 5, 2351-2366.

Example 53: Click Chemistry G11

To a solution of fucoside (1 eq) and 2-[2-[2-(2-azidoethoxy)ethoxy]ethoxy]-ethanol[2] (1.1 eq) in dioxane/water (4:1), were added sodium ascorbate (0.6 eq) and copper sulfate pentahydrate (0.3 eq). The mixture left to stir at 60° C. overnight then Chelex resin was added and the mixture was stirred 30 minutes before filtration. Resin was flushed with MeOH and the filtrate was evaporated under reduce pressure. The residue was purified on silica gel (Dichloromethane/MeOH) to afford the desired compound.

[2] L. N. Goswami, Z. H. Houston, S. J. Sarma, S. S. Jalisatgi, M. F. Hawthorne, *Org. Biomol. Chem.*, 2013, 11, 1116-1126.

Example 54: Deacetylation G12

Acetylated compound was placed in MeoH/H$_2$O (1:1) with Amberlite IRN78 resin at room temperature and stirred overnight. Resin was filtered and flushed with MeOH then the filtrate was concentrated under reduce pressure to afford the desired compound.

Example 55: Propargylation G13

To a solution at 0° C. of diol (4 eq) and NaH (4 eq) in DMF, was added propargyl bromide (1 eq) and stirred overnight to RT. The mixture was diluted in DCM and washed with ice water, saturated aqueous NaHCO$_3$ and brine. The organic phase was dried over MgSO$_4$, filtered and concentrated under reduced pressure. The residue was purified on silica gel (Petroleum ether/Ethyl acetate) to afford the desired chain.

Example 56: Compound 45: 6-(prop-2-ynyloxy)hexan-1-ol

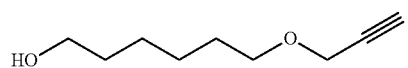

Compound 45 (1.25 mg, 72%, yellow oil) was obtained from hexan-1,6-diol following general procedure G13. Flash chromatography (Petroleum Ether/EtOAc 8/2). The analytical data of compound 45 were in complete agreement with literature data.[3]

[3] N. Ranjan, S. Story, G. Fulcrand, F. Leng, M. Ahmad, A. King, S. Sur, W. Wang, Y-C. Tse-Dinh, D. P. Arya, *J. Med. Chem* 2017, 60, 4904-4922.

Example 57: Compound 46: 4-(prop-2-ynyloxy)butan-1-ol

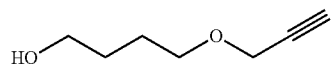

Compound 46 (1.28 mg, 71%, yellow oil) was obtained from butan-1,4-diol following general procedure G13. Flash chromatography (Petroleum Ether/EtOAc 8/2). The analytical data of compound 46 were in complete agreement with literature data.[4]

[4] L Yi, J. Shi, S. Gao, S. Leng, C. Niu, Z. Xi, *Tetrahedron Lett.* 2009, 50, 759-762.

Example 58: Compound 47: cis-4-(prop-2-ynyloxy)buten-1-ol

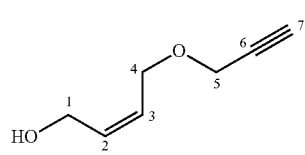

Compound 47 (1.58 mg, 80%, yellow oil) was obtained from cis-2-buten-1,4-diol following general procedure G13. Flash chromatography (Petroleum Ether/EtOAc 8/2). HRMS-ESI m/z calcd for $C_7H_{10}O_2$ [M+Na]$^+$149.0578 found 149.0583. $^1$H NMR (300 MHz, CDCl$_3$) δ 5.79 (dtt, J=11.2, 6.4, 1.3 Hz, 1H, H2 or H3), 5.67-5.55 (m, 1H, H2 or H3), 4.21-4.09 (m, 6H, H1, H4, H5), 2.65 (s, 1H, OH), 2.45 (t, J=2.4 Hz, 1H, H7). $^{13}$C NMR (75 MHz, CDCl$_3$) δ 133.2, 127.1 (C-2, C-3), 79.4 (C-7), 74.9 (C-6), 64.9, 58.3, 57.2 (C-1, C-4, C-5).

Example 59: Compound 48

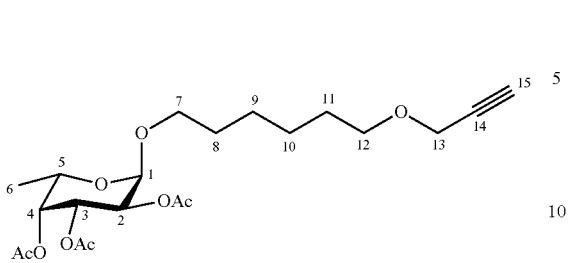

Compound 48 (159.7 mg, 20%, yellow oil) was obtained by Fischer glycosylation of L-Fucose (294 mg, 1.79 mmol) with 6-(prop-2-ynyloxy)hexan-1-ol (chain 1) following general procedure G10. Flash chromatography (Petroleum Ether/EtOAc 8/2). HRMS-ESI m/z calcd for $C_{21}H_{32}O_9$ [M+Na]$^+$ 451.1944 found 451.1942. $^1$H NMR (300 MHz, CDCl$_3$) δ 5.32 (dd, J=10.6, 3.4 Hz, 1H, H3), 5.27 (dd, J=3.4, 1.2 Hz, 1H, H4), 5.07 (dd, J=10.6, 3.7 Hz, 1H, H2), 5.01 (d, J=3.7 Hz, 1H, H1), 4.12 (m, 3H, H5, H13), 3.64 (dt, J=9.8, 6.5 Hz, 1H, CHH H7 or H12), 3.49 (t, J=6.5 Hz, 2H, CH$_2$H7 or H12), 3.37 (dt, J=9.8, 6.5 Hz, 1H, CHH H7 or H12), 2.41 (t, J=2.4 Hz, 1H, H15), 2.14 (s, 3H, CH$_3$), 2.04 (s, 3H, CH$_3$), 1.96 (s, 3H, CH$_3$), 1.57 (td, J=6.7, 4.0 Hz, 4H, H8, H11), 1.41-1.30 (m, 4H, H9, H10), 1.11 (d, J=6.6 Hz, 3H, H6). 13C NMR (75 MHz, CDCl$_3$) δ 170.7, 170.5, 170.2 (3CH$_3$CO), 96.1 (C-1), 80.0 (C-14), 74.2 (C-15), 71.3 (C-4), 70.1, 68.4 (C-7, C-12), 68.4, 68.2 (C-2, C-3), 64.3 (C-5), 58.1 (C-13), 29.5, 29.3, 25.9, 25.9 (C-8, C-9, C-10, C-1), 20.9, 20.8, 20.7 (3CH$_3$CO), 15.98 (C-6).

Example 60: Compound 49

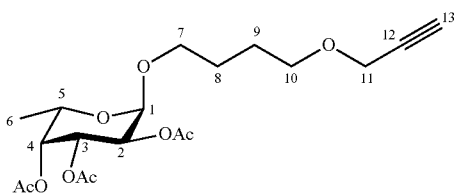

Compound 49 (221.8 mg, 16%, yellow oil) and compound 50 (157 mg, 12%, yellow oil) were obtained by Fischer glycosylation of L-Fucose (546 mg 3.32 mmol) with 4-(prop-2-ynyloxy)butan-1-ol (chain 2) following general procedure G10.

Compound 49: Flash chromatography (Petroleum Ether/EtOAc 8/2). HRMS-ESI m/z calcd for $C_{19}H_{28}O_9$ [M+Na]$^+$ 423.1631 found 423.1619. $^1$H NMR (300 MHz, CDCl$_3$) δ 5.31 (dd, J=10.6, 3.4 Hz, 1H, H3), 5.25 (dd, J=3.4, 1.1 Hz, 1H, H4), 5.06 (dd, J=10.6, 3.7 Hz, 1H, H2), 5.00 (d, J=3.7 Hz, 1H, H1), 4.16-4.07 (m, 3H, H5, H11), 3.73-3.62 (m, 1H, CHH H7 or H10), 3.53-3.47 (m, 2H, CH$_2$H7 or H10), 3.44-3.34 (m, 1H, CHH H7 or H10), 2.41 (t, J=2.4 Hz, 1H, H13), 2.13 (s, 3H, CH$_3$), 2.03 (s, 3H, CH$_3$), 1.95 (s, 3H, CH$_3$), 1.68-1.59 (m, 4H, H8, H9), 1.10 (d, J=6.6 Hz, 3H, H6). $^{13}$C NMR (75 MHz, CDCl$_3$) δ 170.7, 170.5, 170.1 (3 CH$_3$CO), 96.1 (C-1), 79.9 (C-12), 74.34 (C-13), 71.2 (C-4), 69.6 (C-7 or C-10), 68.3 (C-2), 68.1 (C-3, C-7 or C-10), 64.3 (C-5), 58.1 (C-11), 26.2, 26.1 (C-8, C-9), 20.8, 20.7, 20.7 (3 CH$_3$CO), 15.9 (C-6).

Example 61: Compound 50

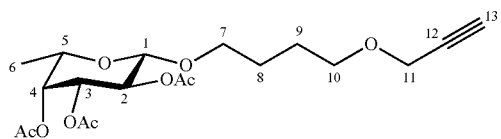

Compound 50: Flash chromatography (Petroleum Ether/EtOAc 7/3). HRMS-ESI m/z calcd for $C19H_{28}O_9$ [M+Na]$^+$ 423.1631 found 423.1619. $^1$H NMR (300 MHz, CDCl$_3$) δ 5.23-5.12 (m, 1H, H4, H3), 4.99 (dd, J=10.4, 3.5 Hz, 1H, H2), 4.41 (d, J=7.9 Hz, 1H, H1), 4.11 (d, J=2.4 Hz, 1H, H11), 3.91 (dt, J=9.1, 5.7 Hz, 1H, CHH H7 or H10), 3.78 (q, J=6.4 Hz, 1H, H5), 3.56-3.41 (m, 3H, CHH H7 or H10, CH$_2$H7 or H10), 2.40 (t, J=2.4 Hz, 1H, H13), 2.15 (s, 3H, CH$_3$), 2.03 (s, 3H, CH$_3$), 1.96 (s, 3H, CH$_3$), 1.72-1.55 (m, 4H, H8, H9), 1.20 (d, J=6.4 Hz, 3H, H6). 13C NMR (75 MHz, CDCl$_3$) δ 170.8, 170.3, 169.6 (3CH$_3$CO), 101.2 (C-1), 80.0 (C-12), 74.2 (C-13), 71.4 (C-2), 70.4 (C-4), 69.8, 69.7 (C-7, C-10), 69.2, 69.1 (C-3, C-5), 58.1 (C-11), 26.2, 25.9 (C-8, C-9), 20.9, 20.8, 20.7 (3CH$_3$CO), 16.2 (C-6).

Example 62: Compound 52

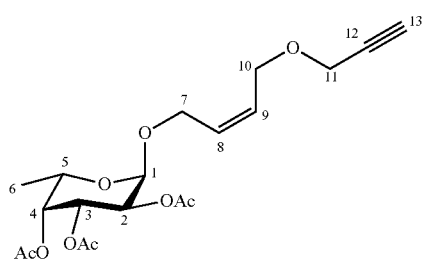

Compound 51 (63.5 mg, 6%, yellow oil) was obtained by Fischer glycosylation of L-Fucose (425 mg, 2.6 mmol) with (Z)-4-(prop-2-ynyloxy)but-2-en-1-ol (chain 3) following general procedure G10. Flash chromatography (Petroleum Ether/EtOAc 8/2). HRMS-ESI m/z calcd for $C_{19}H_{26}O_9$ [M+Na]$^+$ 421.1475 found 421.1466. $^1$H NMR (300 MHz, CDCl3) δ 5.77-5.63 (m, 2H, H8, H9), 5.33 (dd, J=10.6, 3.4 Hz, 1H, H3), 5.26 (dd, J=3.4, 1.2 Hz, 1H, H4), 5.09 (dd, J=10.6, 3.7 Hz, 1H, H2), 5.05 (d, J=3.7 Hz, 1H, H1), 4.26-4.05 (m, 7H, H5, H11, H7, H10), 2.43 (t, J=2.4 Hz, 1H, H13), 2.13 (s, J=2.2 Hz, 3H, CH$_3$), 2.05 (s, 3H, CH$_3$), 1.95 (s, 3H, CH$_3$), 1.12 (d, J=6.6 Hz, 3H, H6). $^{13}$C NMR (75 MHz, CDCl$_3$) δ 170.6, 170.5, 170.0 (3 CH$_3$CO), 129.4, 129.0 (C-8, C-9), 95.5 (C-1), 79.5 (C-12), 74.7 (C-13), 71.2 (C-4), 68.1, 68.0 (C-2, C-3), 65.0, 64.5 (C-7 or C-10, C-5), 63.5 (C-7 or C-10), 57.2 (C-11), 20.9, 20.7, 20.7 (3 CH$_3$CO), 15.9 (C-6).

Example 63: Compound 52

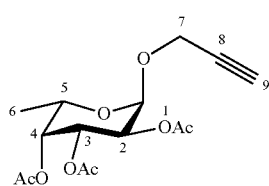

Compound 52 (256 mg, 26%, white solid) was obtained by Fischer glycosylation of L-Fucose (500 mg, 3.04 mmol) with propargyl alcohol following general procedure G10. The analytical data of compound 52 were in complete agreement with literature data.[5]

[5] B. Roy and B. Mukhopadhyay, *Tetrahedron Lett.* 2007, 48, 3783-3787.

(C-1), 79.2 (C-8), 71.4 (C-9), 70.9 (C-4), 68.8 (C-3), 67.7 (C-2), 65.4 (C-5), 20.8, 20.7, 20.6 (3CH$_3$CO), 17.3 (C-7), 15.9 (C-6).

[6] H. Hashimoto, K. Shimada, S. Horito, *Tetrahedron-Asymmetr.* 1994, 5, 2351-2366.

Example 65: Compound 54

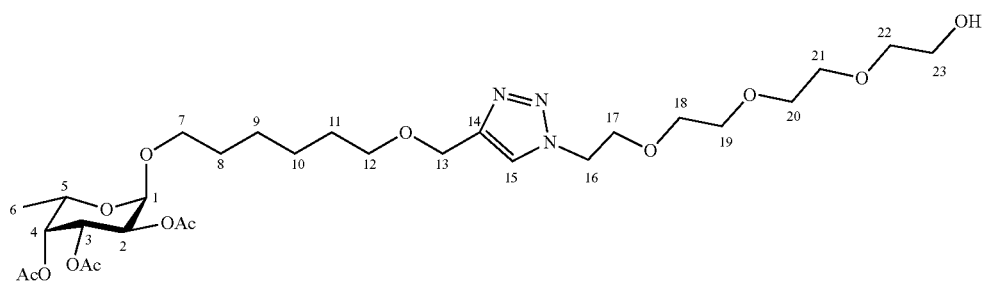

Example 64: Compound 53

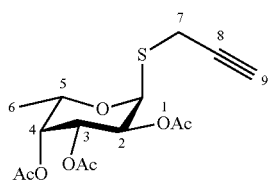

To a solution of 2,3,4-Tri-O-acetyl-1-S-acetyl-1-thio-α-L-fucopyranose[6] (1 eq) in MeOH at 0° C. was added NaSMe (1.1 eq). The solution was stirred for 45 min then propargyl bromide (2.2 eq) was added to the mixture. Stirring was kept 1 h at RT and the solvent was evaporated under reduced pressure. The crude was taken in dichloromethane and washed with HCl 1M and sat. NaCl. The organic layers were dried over MgSO4 and concentrated in vacuo. The residue was purified by flash chromatography (Petroleum Ether/ EtOAc 8/2) to give the compound 53 as a colorless oil (mg, 60%). HRMS-ESI m/z calcd for C$_{15}$H$_{20}$O$_7$S [M+Na]$^+$ 367.0827 found 367.0822. $^1$H NMR (400 MHz, CDCl$_3$) δ 5.85 (d, J=5.7 Hz, 1H, H1), 5.31 (dd, J=10.9, 5.7 Hz, 1H, H2), 5.27 (d, J=1.8 Hz, 1H, H4), 5.17 (dd, J=10.9, 3.3 Hz, 1H, H3), 4.42 (q, J=6.4 Hz, 1H, H5), 3.30 (dd, J=16.7, 2.6 Hz, 1H, H7a), 3.14 (dd, J=16.7, 2.6 Hz, 1H, H7b), 2.21 (t, J=2.6 Hz, 1H, H9), 2.14 (s, 3H, CH$_3$), 2.04 (s, 3H, CH$_3$), 1.96 (s, 3H, CH$_3$), 1.14 (d, J=6.5 Hz, 3H, H6). $^{13}$C NMR (101 MHz, CDCl$_3$) δ 170.5, 170.0, 169.9 (3 CH$_3$CO), 81.8

Compound 54 (45.6 mg, 75%, colorless oil) was obtained from compound 48 (40 mg, 0.093 mmol) following general procedure G11. Flash chromatography (DCM/MeOH 97/3) HRMS-ESI m/z calcd for C$_{29}$H$_{49}$N$_3$O$_{13}$ [M+Na]$^+$ 670.3163 found 670.3163. $^1$H NMR (300 MHz, MeOD) δ 8.03 (s, 1H, H15), 5.38-5.22 (m, 2H, H3, H4), 5.08-5.01 (m, 2H, H2, H1), 4.65-4.57 (m, 4H, H13, H16), 4.27-4.15 (m, 1H, H5), 3.98-3.88 (m, 2H, H17), 3.78-3.38 (m, 17H, 6CH$_2$O, H7, H12, OH), 2.16 (s, 3H, CH$_3$), 2.05 (s, 3H, CH$_3$), 1.97 (s, 3H, CH$_3$), 1.72-1.54 (m, 4H, H8, H11), 1.51-1.35 (m, 4H, H9, H10), 1.14 (t, J=6.1 Hz, 3H, H6). $^{13}$C NMR (75 MHz, MeOD) δ 172.2, 171.9, 171.6 (3CH$_3$CO), 145.9 (C-14), 125.7 (C-15), 97.3 (C-1), 73.6 (CH$_2$), 72.5 (C-4), 71.5-71.3 (5CH$_2$), 70.3 (C-17), 69.6, 69.5 (C-2, C-3), 69.3 (C-7 or C-12), 65.6 (C-5), 64.6 (C-13), 62.20 (CH$_2$), 51.3 (C-16), 30.6, 30.3 (C-8, C-11), 27.0, 26.9 (C-9, C-10), 20.6, 20.4 (3CH$_3$CO), 16.1 (C-6).

Example 66: Compound 55

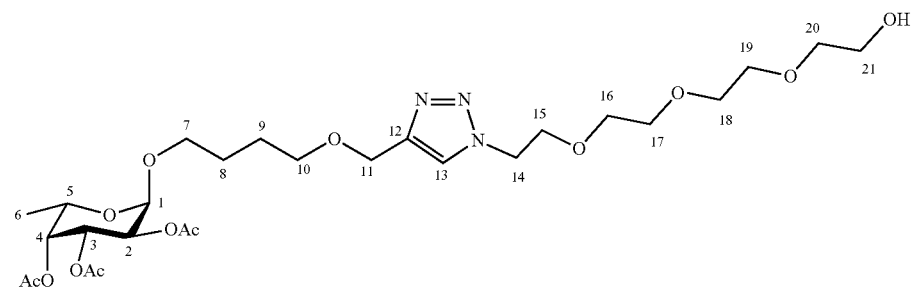

Compound 55 (71.7 mg, 77%, colorless oil) was obtained from compound 49 (60 mg, 0.15 mmol) following general procedure G11. Flash chromatography (DCM/MeOH 96/4) HRMS-ESI m/z calcd for C$_{27}$H$_{45}$N$_3$O$_{13}$ [M+Na]$^+$ 642.2850 found 642.2852. $^1$H NMR (300 MHz, MeOD) δ 8.04 (s, 1H, H13), 5.38-5.25 (m, 2H, H3, H4), 5.11-4.97 (m, 2H, H2, H1), 4.66-4.56 (m, 4H H11, H14), 4.24-4.15 (m, 1H, H5), 3.98-3.87 (m, 2H, H15), 3.80-3.39 (m, 18H 6CH$_2$O, H7, H10, OH), 2.16 (s, 3H, CH$_3$), 2.05 (s, 3H, CH$_3$), 1.97 (s, 3H, CH$_3$), 1.77-1.64 (m, 4H, H8, H9), 1.12 (d, J=6.5 Hz, 3H, H6). $^{13}$C NMR (75 MHz, MeOD) δ 172.2, 171.9, 171.6 (3CH$_3$CO), 145.9 (C-12), 125.7 (C-13), 97.4 (C-1), 73.6 (CH$_2$), 72.5 (C-4), 71.5-71.1 (5CH$_2$), 70.3 (C-15), 69.6, 69.5 (C-2, C-3), 69.1 (C-7 or C-10), 65.6 (C-5), 64.6 (C-11), 62.1 (CH$_2$), 51.3 (C-14), 27.3, 27.2 (C-8, C-9), 20.6, 20.4 (3CH$_3$CO), 16.1 (C-6).

Example 67: Compound 56

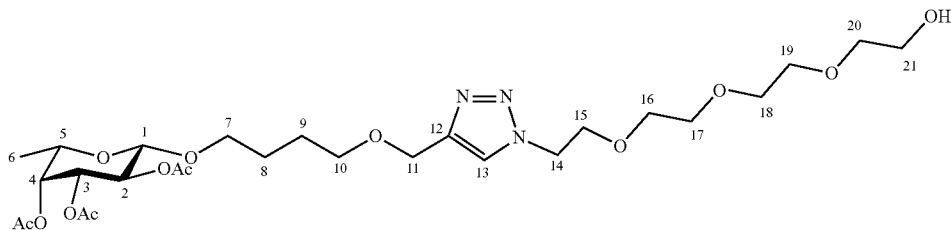

Compound 56 (64.9 mg, 83%, colorless oil) was obtained from compound 50 (50 mg, 0.125 mmol) following general procedure G11. Flash chromatography (DCM/MeOH 96/4) HRMS-ESI m/z calcd for C$_{27}$H$_{45}$N$_3$O$_{13}$ [M+Na]$^+$ 642.2850 found 642.2857.

$^1$H NMR (300 MHz, MeOD) δ 8.05 (s, 1H, H13), 5.24 (dd, J=3.0, 1.0 Hz, 1H, H4), 5.15-5.01 (m, 2H, H2, H3), 4.65-4.55 (m, 5H, H1, H11, H14), 4.03-3.82 (m, 4H, H5, HIS, H7a or H10a), 3.73-3.48 (m, 16H, 6CH$_2$O, H7 or H10, OH), 2.18 (s, 3H, CH$_3$), 2.04 (s, 3H, CH$_3$), 1.96 (s, 3H, CH$_3$), 1.69-1.59 (m, 4H, H8, H9), 1.20 (d, J=6.4 Hz, 3H, H6). $^{13}$C NMR (75 MHz, MeOD) δ 172.2, 171.5, 171.4 (3CH$_3$CO), 145.9 (C-12), 125.7 (C-13), 102.0 (C-1), 73.6 (CH$_2$), 72.7 (C-2), 71.9 (C-4), 71.5-71.1 (5CH$_2$), 70.5 (C-3), 70.4, 70.3 (C-15, C-7 or C-10), 70.0 (C-5), 64.6 (C-11), 62.2 (CH$_2$), 51.3 (C-14), 27.3, 27.1 (C-8, C-9), 20.7, 20.5, 20.5 (3CH$_3$CO), 16.3 (C-6).

Example 68: Compound 57

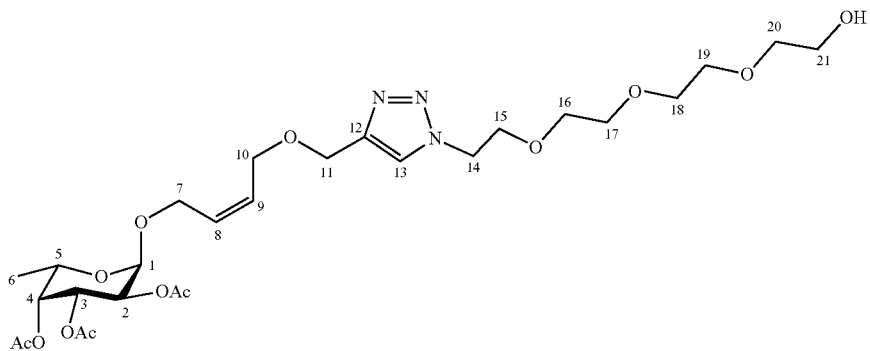

Compound 57 (67.8 mg, 77%, colorless oil) was obtained from compound 51 (60 mg, 0.15 mmol) following general procedure G11. Flash chromatography (DCM/MeOH 95/5) HRMS-ESI m/z calcd for C$_{27}$H$_{43}$N$_3$O$_{13}$ [M+Na]$^+$ 640.2694 found 642.2710. $^1$H NMR (300 MHz, MeOD) δ 8.07 (s, J=3.2 Hz, 1H, H13), 5.88-5.67 (m, 2H, H8, H9), 5.39-5.24 (m, 2H, H3, H4), 5.12-5.05 (m, 2H, H2, H1), 4.66-4.55 (m, 4H, H11, H14), 4.33-4.13 (m, 5H, H5, H7, H10), 3.99-3.86 (m, 2H, HIS), 3.77-3.52 (m, 13H, 6CH$_2$O, OH), 2.19 (s, 3H, CH$_3$), 2.07 (s, 3H, CH$_3$), 1.99 (s, 3H, CH$_3$), 1.15 (d, J=6.5 Hz, 3H, 6). $^{13}$C NMR (75 MHz, MeOD) δ 172.2, 171.9, 171.6 (3CH$_3$CO), 145.6 (C-12), 131.0, 129.4 (C-8, C-9), 125.8 (C-13), 96.6 (C-1), 73.6 (CH$_2$), 72.5 (C-4), 71.5, 71.4, 71.3 (4CH$_2$), 70.3 (C-15), 69.4, 69.3 (C2, C3), 66.8 (C7 or C-10), 65.8 (C-5), 64.4 (C-7 or C-10), 64.0 (C-11), 62.1 (CH$_2$), 51.3 (C-14), 20.6, 20.6, 20.5 (3CH$_3$CO), 16.1 (C-6).

Example 69: Compound 58

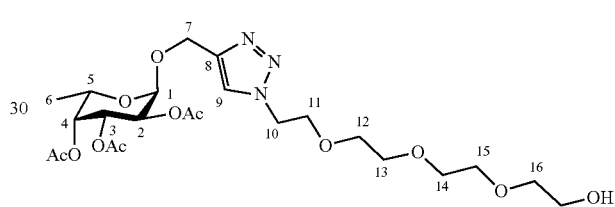

Compound 58 (170 mg, 90%, colorless oil) was obtained from compound 52 (115 mg, 0.35 mmol) following general procedure G11. Flash chromatography (DCM/MeOH 96/4) HRMS-ESI m/z calcd for C$_{23}$H$_{37}$N$_3$O$_{12}$ [M+Na]$^+$ 570.2275 found 570.2280. $^1$H NMR (300 MHz, MeOD) δ 8.12 (d, J=7.3 Hz, 1H, H9), 5.36-5.27 (m, 2H, H3, H4), 5.16 (d, J=3.7 Hz, 1H, H1), 5.04 (dd, J=10.6, 3.7 Hz, 1H, H2), 4.81 (d, J=12.5 Hz, 1H, H7a), 4.69 (d, J=12.5 Hz, 1H, H7b), 4.65-4.58 (m, 2H, H10), 4.31-4.21 (m, 1H, H5), 3.97-3.88 (m, 2H, H11), 3.71-3.53 (m, 13H, 6CH$_2$O, OH), 2.16 (s, 3H, CH$_3$), 2.01 (s, 3H, CH$_3$), 1.96 (s, 3H, CH$_3$), 1.13 (d, J=6.5 Hz, 3H, H6). $^{13}$C NMR (75 MHz, MeOD) δ 172.2, 171.8, 171.5 (3CH$_3$CO), 144.9 (C-8), 126.4 (C-9), 96.7 (C-1), 73.6

(CH₂), 72.5 (C-4), 71.5-70.3 (5CH₂O), 69.3, 69.2 (C-2, C-3), 65.9 (C-5), 62.2 (CH₂), 61.6 (C-7), 51.4 (C-10), 20.6, 20.4 (3CH₃CO), 16.1 (C-6).

Example 70: Compound 59

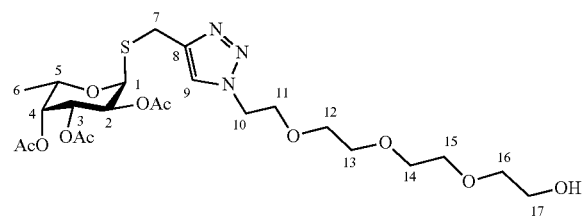

Compound 59 (32.4 mg, 50%, colorless oil) was obtained from compound 53 (40 mg, 0.12 mmol) following general procedure G11. Flash chromatography (DCM/MeOH 96/4) HRMS-ESI m/z calcd for $C_{23}H_{37}N_3O_{11}S$ [M+Na]⁺ 586.2046 found 586.2049. ¹H NMR (300 MHz, MeOD) δ 7.95 (s, 1H, H9), 5.66-5.58 (m, 1H, H1), 5.30 (d, J=1.1 Hz, 1H, H4), 5.26-5.12 (m, 2H, H2, H3), 4.61-4.55 (m, 2H, H10), 4.55-4.46 (m, 1H, H5), 3.95-3.79 (m, 4H, H7, H11), 3.72-3.55 (m, 13H, 6CH₂O, OH), 2.17 (s, 3H, CH₃), 2.01 (s, 3H, CH₃), 1.97 (s, 3H, CH₃), 1.13 (d, J=6.5 Hz, 3H, H6). ¹³C NMR (75 MHz, MeOD) δ 172.1, 171.4 (3CH₃CO), 145.4 (C-8), 125.2 (C-9), 82.87 (C-1), 73.6 (CH₂), 72.24 (C-4), 71.5-71.4 (4CH₂), 70.3 (C-11), 70.0, 69.1 (C-2, C-3), 66.4 (C-5), 62.2 (CH₂), 51.4 (C-10), 24.3 (C-7), 20.5, 20.5, 20.4 (3 CH₃CO), 16.1 (C-6).

Example 71: Compound 60

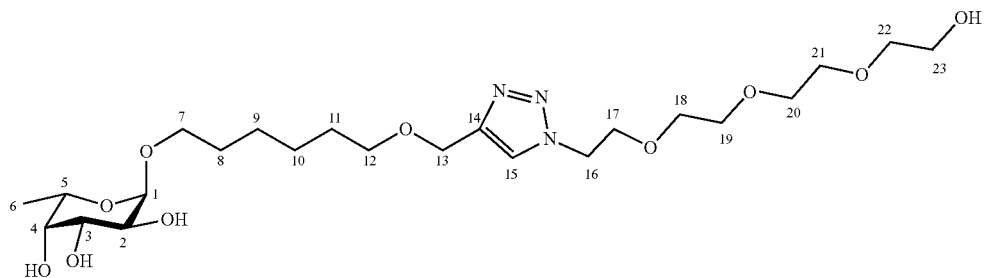

Compound 60 (30.8 mg, 96%, colorless oil) was obtained from compound 54 (40 mg, 0.062 mmol) following general procedure G12. HRMS-ESI m/z calcd for $C_{23}H_{43}N_3O_{10}$ [M+Na]⁺ 544.2846 found 544.2849.

¹H NMR (300 MHz, MeOD) δ 8.03 (s, 1H, H15), 4.74 (d, J=2.3 Hz, 1H, H1), 4.63-4.56 (m, 4H, H7, H16), 3.99-3.86 (m, 3H, H5, H17), 3.77-3.38 (m, 20H, H2, H3, H4, H7, H12, 6CH₂O, OH), 1.72-1.53 (m, 4H, H8, H11), 1.48-1.34 (m, 4H, H9, H10), 1.20 (d, J=6.6 Hz, 3H, H6). ¹³C NMR (75 MHz, MeOD) δ 145.9 (C-14), 125.8 (C-15), 100.44 (C-1), 73.7, 73.6 (C-4, CH₂), 71.69 (C-2 or C-3), 71.5-71.3 (5CH₂), 70.3 (C-17), 70.0 (C-2 or C-3), 69.15 (CH₂), 67.4 (C-5), 64.6 (C-13), 62.2 (CH₂), 51.3 (C-16), 30.6, 30.5 (C8, C-11), 27.1, 27.0 (C-9, C-10), 16.6 (C-6).

Example 72: Compound 61

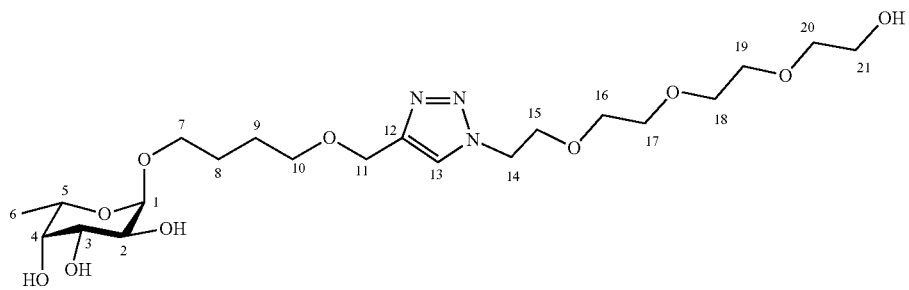

Compound 61 (47.7 mg, 92%, colorless oil) was obtained from compound 55 (65 mg, 0.105 mmol) following general procedure G12. HRMS-ESI m/z calcd for $C_{21}H_{39}N_3O_{10}$ [M+Na]$^+$ 516.2533 found 51-0.2531. $^1$H NMR (300 MHz, MeOD) δ 8.05 (s, 1H, H13), 4.75 (d, J=1.9 Hz, 1H, H1), 4.63-4.58 (m, 4H, H11, H14), 3.98-3.88 (m, 3H, H5, H15), 3.75-3.72 (m, 2H, H2, H3), 3.71-3.40 (m, 18H, H4, H7, H10, 6CH$_2$O, OH), 1.78-1.64 (m, 4H, H8, H9), 1.21 (d, J=6.6 Hz, 3H, H6). $^{13}$C NMR (75 MHz, MeOD) δ 145.9 (C-12), 125.8 (C-13), 100.4 (C-1), 73.7 (CH$_2$), 73.6 (C-4), 71.6 (C-2 or C-3), 71.5-71.3 (5CH$_2$), 70.3 (C-15), 70.0 (C-2 or C-3), 68.9 (CH$_2$), 67.4 (C-5), 64.6 (C-11), 62.1 (CH$_2$), 51.3 (C-14), 27.4, 27.3 (C-8, C-9), 16.6 (C-6).

[M+Na]$^+$ 514.2377 found 514.2377. $^1$H NMR (300 MHz, MeOD) δ 8.05 (s, 1H, H13), 5.87-5.66 (m, 2H, H8, H9), 4.79 (d, J=1.7 Hz, 1H, H1), 4.64-4.56 (m, 4H, H11, H15), 4.27-4.09 (m, 4H, H7, H10), 3.99-3.87 (m, 3H, H5, H15), 3.78-3.69 (m, 2H, H2, H3), 3.69-3.47 (m, 14H, H4, 6CH$_2$O, OH), 1.21 (d, J=6.6 Hz, 3H, H6). $^{13}$C NMR (75 MHz, MeOD) δ 145.6 (C-12), 130.3, 130.2 (C-8, C-9), 125.9 (C-13), 99.7 (C-1), 73.6 (CH$_2$), 73.5 (C-4), 71.6 (C-2 or C-3), 71.5-71.3 (4CH$_2$), 70.3 (C-15), 69.8 (C-2 or C-3), 67.6 (C-5), 66.8, 64.1 (C-7, C-10), 64.0 (C-11), 62.1 (CH$_2$), 51.3 (C-14), 16.7 (C-6).

Example 73: Compound 62

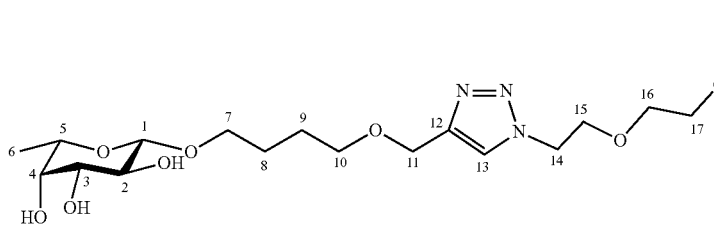

Compound 62 (32.5 mg, 92%, colorless oil) was obtained from compound 56 (44 mg, 0.071 mmol) following general procedure G12. HRMS-ESI m/z calcd for $C_{21}H_{39}N_3O_{10}$ [M+Na]$^+$ 516.2533 found 516.2531. $^1$H NMR (300 MHz, MeOD) δ 8.04 (s, 1H, H13), 4.65-4.55 (m, 4H, H11, H14), 4.23-4.14 (m, 1H, H1), 3.94-3.82 (m, 3H, H15, H7a or H10a), 3.71-3.50 (m, 18H, H3, H5, H7b or H10b, H7 or H10, 6CH$_2$O, OH), 3.49-3.44 (m, 2H, H2, H4), 1.78-1.62 (m, 4H, H8, H9), 1.27 (d, J=6.5 Hz, 3H, H6). $^{13}$C NMR (75 MHz, MeOD) δ 145.9 (C-12), 125.80 (C-16), 104.79 (C-1), 75.1 (C-2), 73.64 (CH$_2$), 73.02 (C-3), 72.29 (C-4), 71.81 (C-5), 71.5-71.3 (5CH$_2$), 70.34, 70.31 (C-15, C-7 or C-10), 64.58 (C-11), 62.19 (CH$_2$), 51.38 (C-14), 27.47, 27.24 (C-8, C-9), 16.78 (C-6).

Example 74: Compound 63

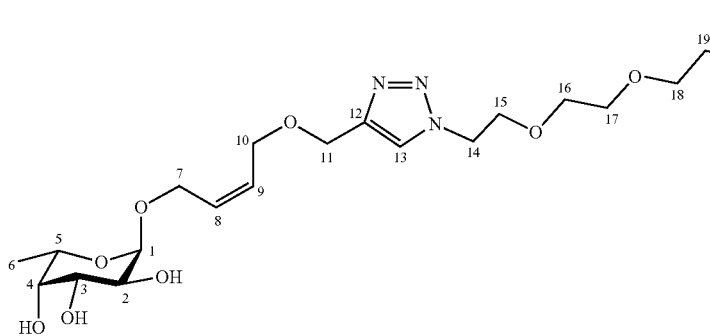

Compound 63 (44.3 mg, 93%, colorless oil) was obtained from compound 57 (60 mg, 0.97 mmol) following general procedure G12. HRMS-ESI m/z calcd for $C_{21}H_{37}N_3O_{10}$

Example 75: Compound 64

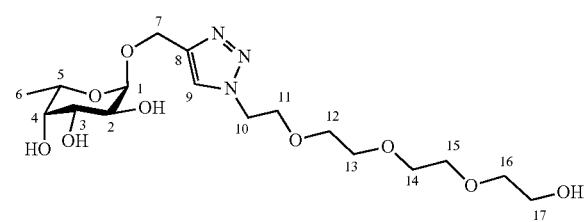

Compound 64 (116 mg, 96%, colorless oil) was obtained from compound 58 (158 mg, 0.29 mmol) following general procedure G12. HRMS-ESI m/z calcd for $C_{17}H_{31}N_3O_9$ [M+Na]$^+$ 444.1958 found 444.1951. $^1$H NMR (300 MHz, MeOD) δ 8.09 (s, 1H, H9), 4.90 (m, 1H, H1), 4.79 (d, J=12.5 Hz, 1H, H7a), 4.66 (d, J=12.4 Hz, 1H, H7b), 4.62-4.58 (m, 2H, H10), 4.02-3.94 (m, 1H, H5), 3.94-3.88 (m, 2H, H11), 3.80-3.71 (m, 2H, H2, H3), 3.70-3.54 (m, 13H, H4, 6CH$_2$O), 1.21 (d, J=6.6 Hz, 3H, H6). 13C NMR (75 MHz, MeOD) δ 145.5 (C-8), 125.9 (C-9), 100.1 (C-1), 73.64 (C-4), 73.62 (CH$_2$), 71.60 (C-2 or C-3), 71.5-71.3 (4CH$_2$), 70.34 (C-11), 69.9 (C-2 or C-3), 67.8 (C-5), 62.2 (C-7), 61.6 (CH$_2$), 51.4 (C-10), 16.6 (C-6).

Example 76: Compound 65

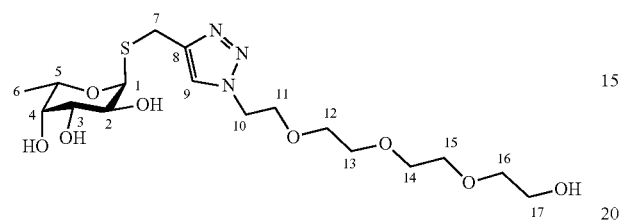

Compound 65 (19.8 mg, 93%, colorless oil) was obtained from compound 59 (27.5 mg, 0.049 mmol) following general procedure G12. HRMS-ESI m/z calcd for C$_{17}$H$_{31}$N$_3$O$_8$S [M+Na]$^+$ 460.1730 found 460.1723. $^1$H NMR (300 MHz, MeOD) δ 7.94 (s, 1H, H9), 5.32 (d, J=5.6 Hz, 1H, H1), 4.58-4.52 (m, 2H, H10), 4.25 (q, J=6.7 Hz, 1H, H5), 4.05 (dd, J=10.0, 5.6 Hz, 1H, H2), 3.91-3.81 (m, 3H, H11, H7a), 3.76 (d, J=14.4 Hz, 1H, H7b), 3.70-3.53 (m, 14H, 6CH$_2$O, H3, H4), 1.20 (d, J=6.6 Hz, 3H, H6). $^{13}$C NMR (75 MHz, MeOD) δ 146.2 (C-8), 125.1 (C-9), 86.7 (C-1), 73.64 (CH$_2$), 73.39, 72.47 (C-3, C-4), 71.5-71.4 (4CH$_2$), 70.3 (C-11), 69.3 (C-2), 68.1 (C-5), 62.21 (CH$_2$), 51.41 (C-10), 24.21 (C-7), 16.66 (C-6).

Example 77: Monovalent Compounds

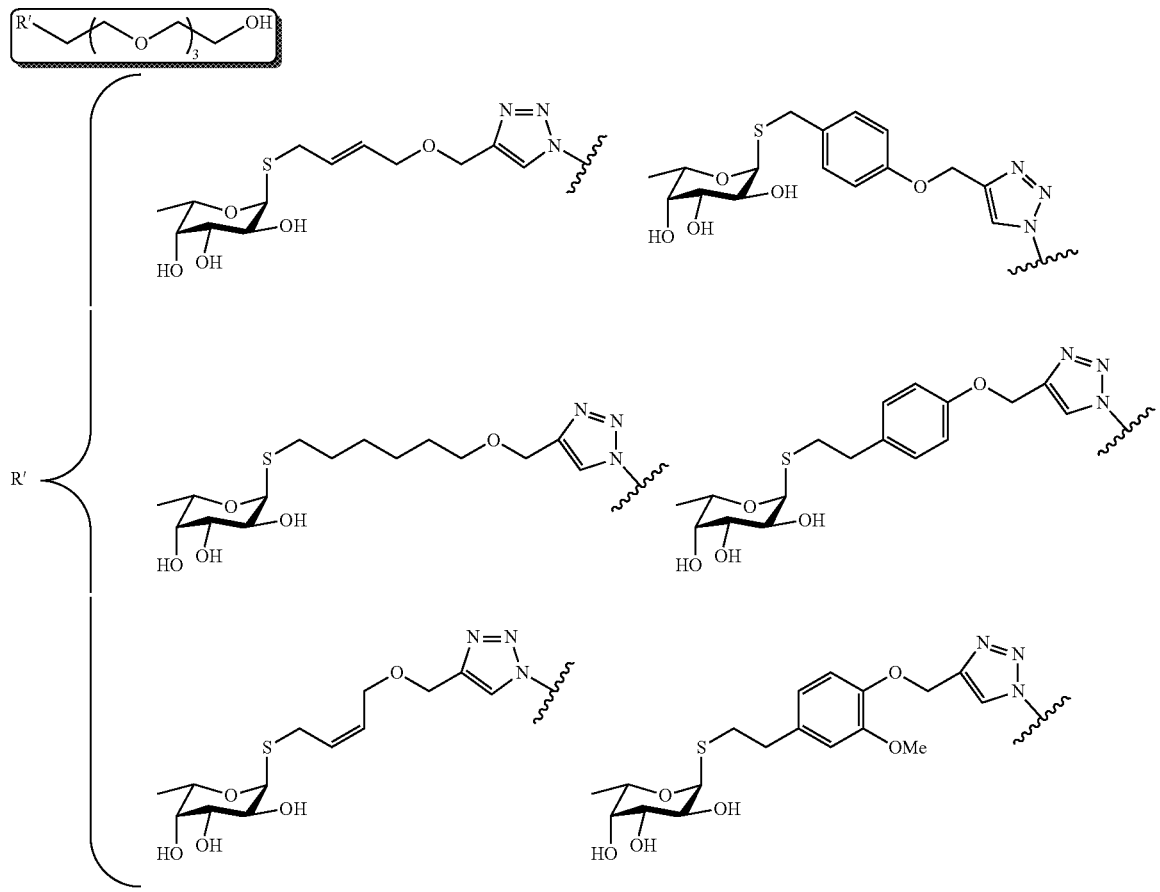

Monovalent compounds described above are obtained from the corresponding protected alkynes and 2-[2-[2-(2-azidoethoxy)ethoxy]ethoxy]-ethanol scaffold following CuAAC general procedure G11, and acetate deprotection general procedure G12.

Example 78: Divalent Compounds
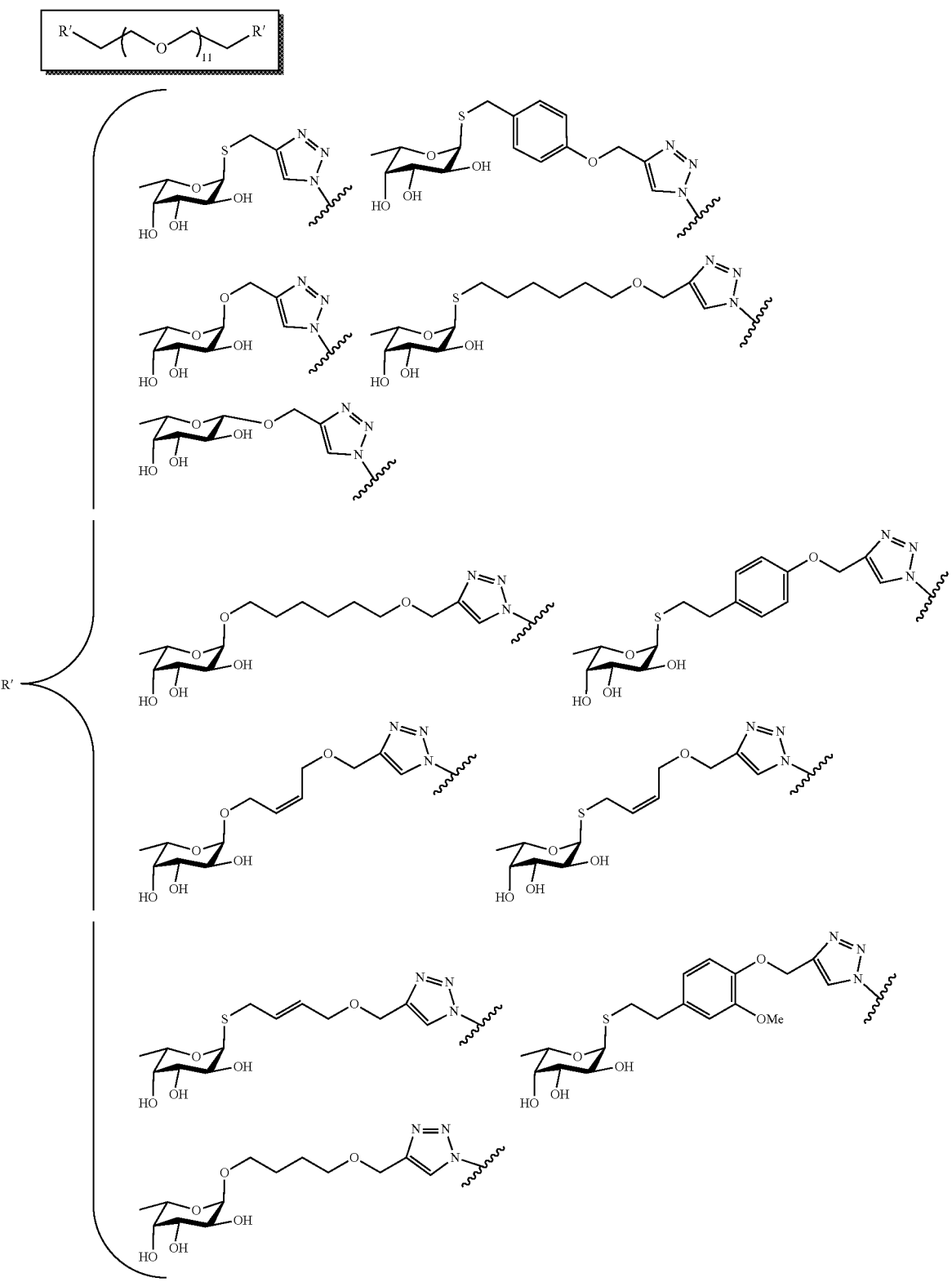

Divalent compounds described above are obtained from the corresponding alkynes and di-azide scaffolds following general procedure G3 or G4, then general procedure G5 or G12.
Example 79: Cyclodextrin Compounds
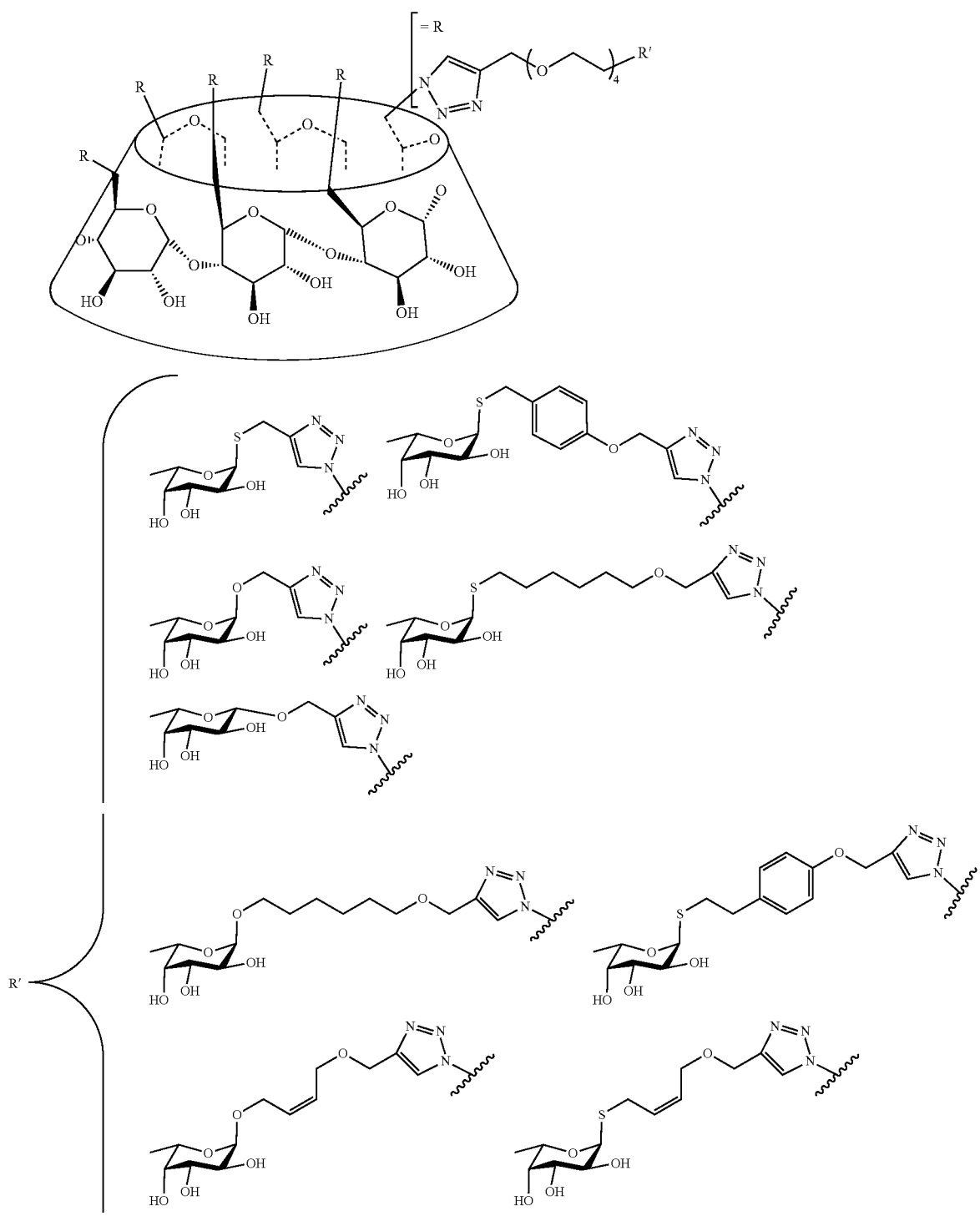

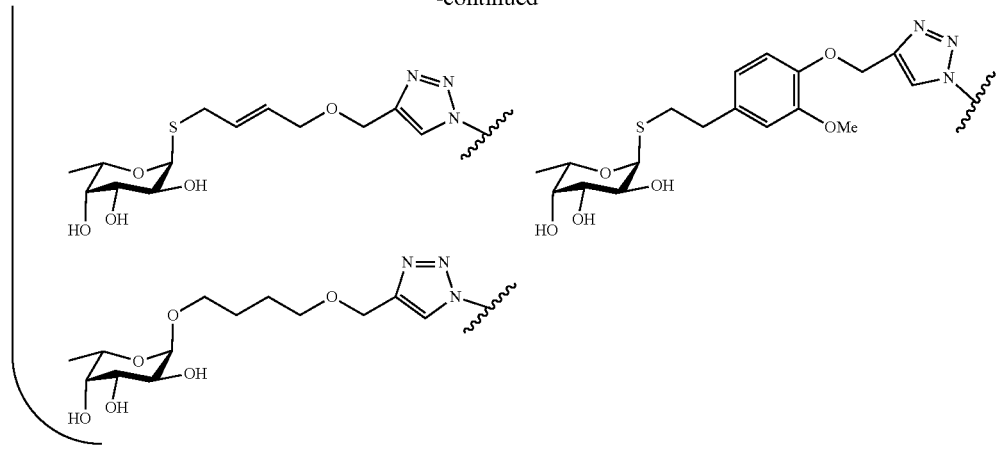
Cyclodextrin compounds described above are obtained from the corresponding alkynes and azide following general procedure G3, then general procedure G5 or G6.
Example 80: POSS Compounds
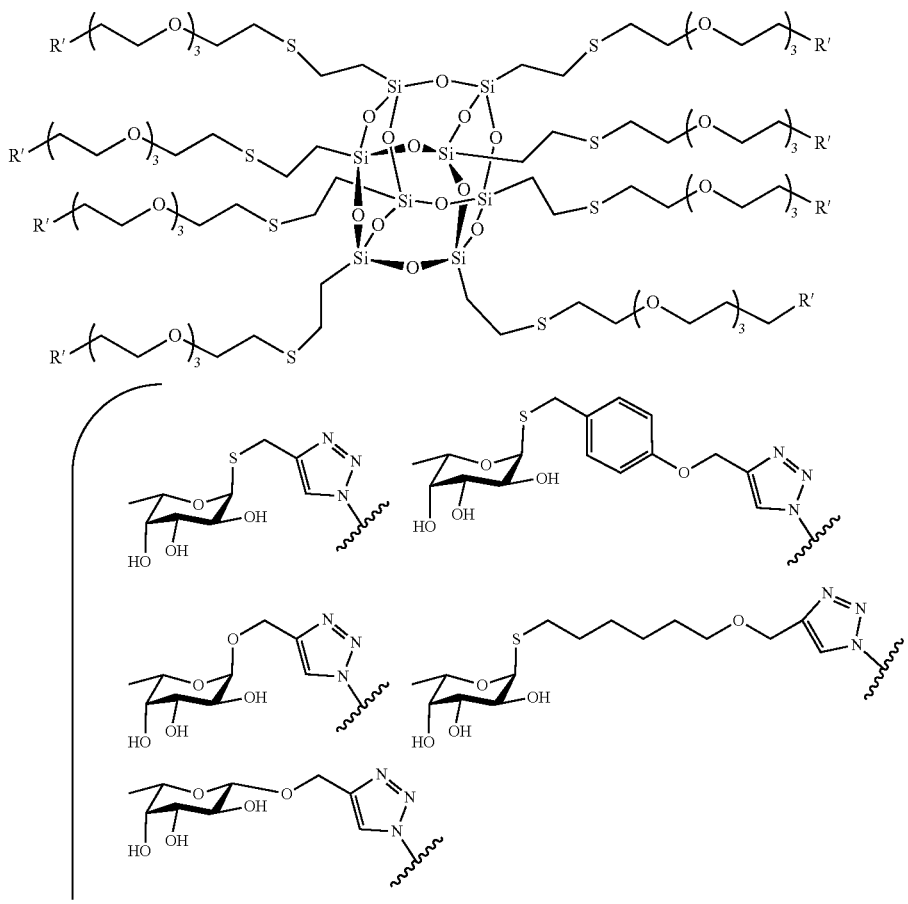

-continued

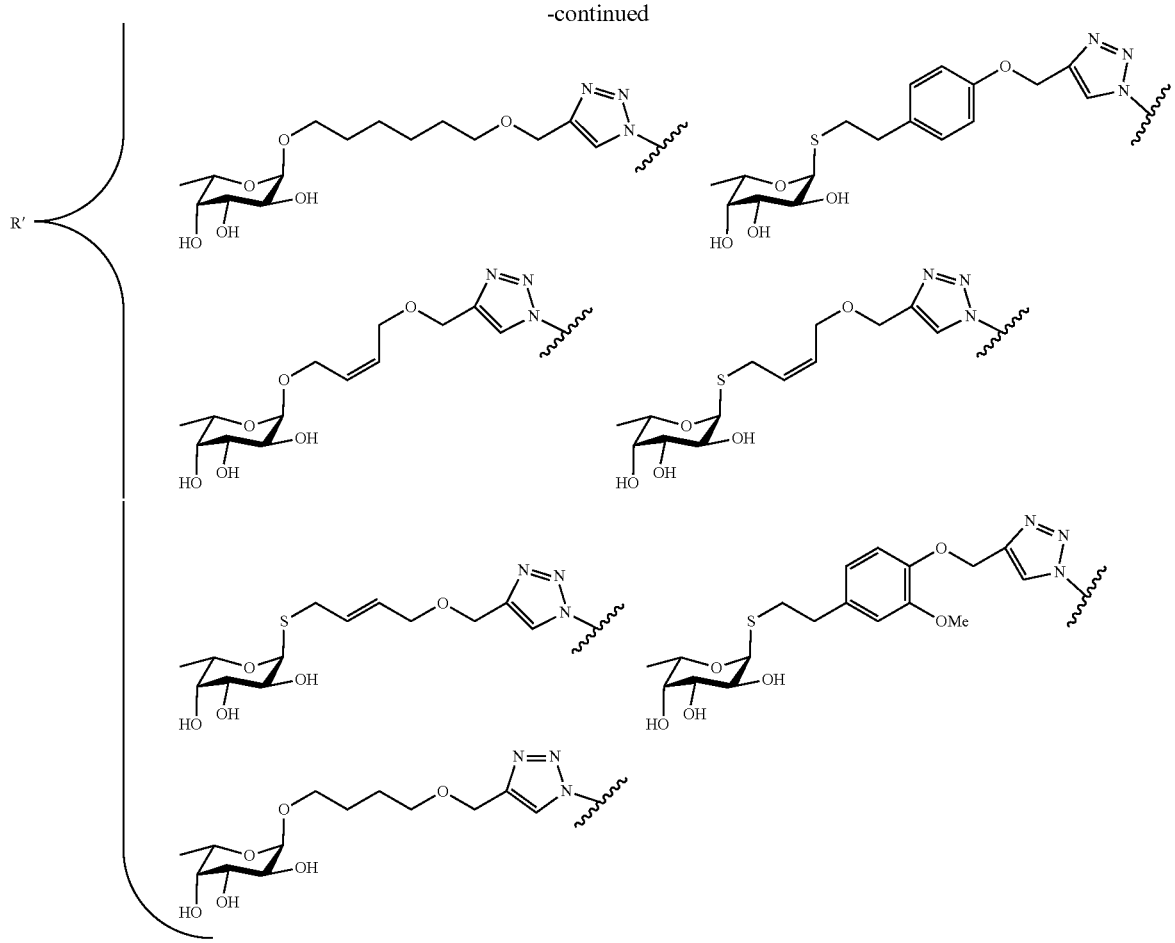

POSS compounds described above are obtained from the corresponding alkyne ligands and scaffold 39 following the same procedure as the one used to prepare compound 40.

Example 81: Isothermal Titration Calorimetry i. Description of the Method

Isothermal titration calorimetry (ITC) is a method often used to measure the thermodynamic constants of the interaction between a biomolecule (AFL) and a synthetic ligand. It is the only technique to measure both the enthalpic and entropic parameters of binding, without modification of the partners involved. This method is based on the estimation of the release of heat upon formation of the ligand-receptor linkage in a microcalorimeter having two cells. One contains ultra-pure water maintained at a precise temperature and serves as a reference cell; the other contains a protein solution at a fixed concentration (FIG. 1-I). To this solution, the apparatus adds a precise volume of a ligand solution at regular intervals of time, with stirring. This injection then generates a variation of heat with respect to the reference cell which is compensated by a heating resistor. The power needed to maintain the temperature is then recorded for all ligand injections. The integration of the raw data in the form of a graph (FIGS. 1-II and 1-III) gives access to the association constant Ka, to the stoichiometric data and enthalpy data ($\Delta H$) of bonding. From this data it is then possible to determine the free enthalpy ($\Delta G$) and the entropy variation of the system ($\Delta S$).

The dissociation constant obtained from the equilibrium slope indicates the ligand-protein thermodynamic affinity, while the energy difference between the lower plate and the upper plate gives the enthalpy value. This demonstrates the contribution of hydrogen bonds and Van der Waals energies to the bond formed. The values of free enthalpy and entropy can be deduced from the first data acquired thanks to the equations of thermodynamics. Entropy gives us the part of the conformational aspects like the loss of degrees of freedom.

ii. Results

Hexavalent compounds 29 and 30 have been tested as well as the reference compound 33 (useful for the determination of the β-effect) and ligands 24, 26 and 28 bearing a spacer oligoethyleneglycol (OEG) of respectively 4, 12 and 28 units. The data are gathered in Table 1. The free α-cyclodextrine (ie without fucose derivatives; data not shown) has shown no affinity for the AFL lectin.

A multivalent effect (β-effect) is observed if the binding potency value recorded with a multivalent construct having x tethered ligands (or epitopes) is more than x times greater than that of the corresponding monovalent ligand. This term can be calculated with dissociation constant values (Kd) and express as the β factor with $\beta=(Kd)_{monovalent}/[(Kd)_{multivalent} \times \text{Valency}]$. If the β value, also termed the relative potency per ligand, is identical to the monomeric reference, the effect occurring is purely statistical and no real affinity gain is observed.

TABLE 1

Thermodynamic data of the ligand-protein interaction measured by ITC. The β-factor is obtained by the ratio of Kd and the amount of fucose derivatives on the scaffold.

| Compound | Valence | OEG (n) | Stoichiometry | Kd (μM) | −ΔH (kJ/mol) | −TΔS (kJ/mol) | −ΔG (kJ/mol) | β |
|---|---|---|---|---|---|---|---|---|
| αMeFuc | 1 | 0 | 5 | 517 | 48 | 26.8 | 16.9 | — |
| 33 | 1 | 4 | 4.0 ± 0.3 | 167 ± 62 | 60 ± 8 | 38 ± 9 | 22 ± 1 | 3 |
| 24 | 2 | 4 | 2.12 ± 0.03 | 3.8 ± 0.3 | 77 ± 3 | 46 ± 3 | 31 ± 0.2 | 68 |
| 26 | 2 | 12 | 2.35 ± 0.31 | 0.55 ± 0.19 | 74 ± 6 | 36 ± 0.6 | 35.9 ± 0.9 | 470 |
| 28 | 2 | 28 | 3.81 ± 0.08 | 52 ± 2 | 52 ± 5 | 28 ± 5 | 24.5 ± 0.1 | 5 |
| 29 | 6 | 2 | 1.01 ± 0.02 | 0.60 ± 0.03 | 161 ± 1 | 125.5 ± 0.6 | 35.5 ± 0.1 | 144 |
| 30 | 6 | 4 | 0.77 ± 0.04 | 0.18 ± 0.01 | 220 ± 8 | 181 ± 8 | 38.4 ± 0.2 | 479 |

The dissociation constants prove the interaction strength between the fucose moiety and the lectin AFL. Table 1 shows a comparison of the dissociation constants of the different compounds.

The multivalent compounds present Kd values inferior of the Kd value of the monovalent references αMeFuc (methylfucoside) and 33. The hexavalent compounds 29 and 30 have Kd values in the sub-micromolar range and compound 30 has the best affinity associated with a low Kd of 180 nM and a high β-factor of 479 (calculated from methylfucoside). This is clearly indicative of the strong benefit in designing multivalent fucosides based on a cyclodextrin core to improve AFL affinity (FIG. 2).

The divalent compounds show also a significant β effect (β=68; 470; 5 respectively for compounds 24, 26 and 28) compared to methylfucoside. Compounds 24 and 28 present moderate β effect compared to compound 26 highlighting the fundamental importance of the length of the spacer related to the strength of the interaction with the AFL. Compound 26 have a twelve ethyleneglycol unit spacer adapted to efficiently interact with different binding sites of the AFL (Kd=550 nM). A n value equal to 4 means that the compound does not necessarily link two binding sites on a same molecule and can also indicate an aggregation phenomenon.

The stoichiometry of the interaction (Table 1) indicates the amount of ligand bound to a single protein. It appears that a single hexavalent compound is linked by the protein, which indicates a chelate mode of interaction. The divalent compounds 24, 26, and 28 have, respectively, a stoichiometry of 2.12, 2.35 and 3.81, probably indicative of a chelate binding mode for 24 and 26 and a monovalent binding for 28. This would explain the much lower affinity enhancement for AFL observed with the latter.

The αMeFuc reference has a Kd value of 517 μM. In comparison, the monovalent reference compound 33 has a slightly lower Kd value (167 μM), indicating that the aglycone moiety (triazole and OEG) induces a slight increase of the affinity. The divalent compounds 24, 26 and 28 present similar enthalpic and entropic contributions compared to the reference monovalent compound 33. However, the hexavalent compound 29, bearing n=2 OEG units, has a 2.7 times higher enthalpic contribution than the reference monovalent compound and the hexavalent compound 30, bearing n=4 OEG units, has a 3.7 times higher enthalpic contribution, which is highly favorable for AFL interaction. The entropic evolution is damaging for this interaction with a 3.3 increase of the −TΔS factor for compound 29 and a 4.7 increase of the −TΔS factor for compound 30. These enthalpic and entropic variations indicate that different kinds of interactions exist between the multivalent compounds and the different binding sites of AFL.

The compounds were evaluated in a second batch of purified AFL protein and the data are gathered in Table 2. In this series of measure, the αMeFuc reference has a $K_d$ value of 109.5 μM (FIG. 5A). Values obtained for compounds 29 and 30 are comparable to the one obtained previously and described in Table 1. Removal of the OEG spacer for compound 44 led to a significant decrease in affinity compared to 29 and 30, probably because the linkers of 44 are too short to allow a chelate binding mode.

Octavalent compounds 40, 41 and 42 have been tested and the stoichiometry indicates that a single octavalent compound is bound to more than one protein which is indicative of a aggregative or chelate-aggregative binding (FIG. 5C). Enthalpic and entropic contributions are comparable despite a lower affinity for compound 40. This could result from the absence of spacer between the triazole and the fucose unit. The best affinity is observed for compound 42 which is 4 times higher than for the best hexavalent compound 30.

Altogether these results show the high (nanomolar) affinity reached by the multivalent fucosides developed herein and based on the cyclodextrin and POSS scaffolds.

TABLE 2

Thermodynamic data of the ligand-protein interaction measured by ITC.

| Compound | N | $K_d$ [μM] | −ΔG (kJ/mol) | −ΔH [kJ/mol] | −TΔS [kJ/mol] |
|---|---|---|---|---|---|
| αMeFuc | 3.3 ± 0.42 | 109.5 ± 1.1 | 22.6 ± 0.02 | 64.3 ± 6.2 | 41.7 ± 6.2 |
| 44 | 1.36 ± 0.01 | 1.94 ± 0.5 | 32.7 ± 0.7 | 122.9 ± 1.9 | 90.4 ± 2.6 |
| 29 | 1.20 ± 0.09 | 0.53 ± 0.04 | 35.9 ± 0.2 | 171.8 ± 15.3 | 136.1 ± 15.1 |
| 30 | 0.95 ± 0.02 | 0.13 ± 0.01 | 39.3 ± 0.3 | 208.9 ± 1.0 | 169.4 ± 0.6 |
| 40 | 0.84 ± 0.02 | 0.40 ± 0.07 | 36.6 ± 0.4 | 252.9 ± 17.0 | 216.8 ± 16.9 |
| 41 | 0.76 ± 0.09 | 0.05 ± 0.002 | 41.6 ± 0.1 | 237.3 ± 26.9 | 195.6 ± 26.9 |
| 42 | 0.71 ± 0.04 | 0.04 ± 0.004 | 42.6 ± 0.3 | 247.2 ± 16.0 | 205.0 ± 16.2 |

Example 82: Adhesion Test of the Conidia on Pneumocytes in the Presence of Fucoside Derivatives i. Description of the Method The principle of the method is schematized on FIG. 3.

The anti-adhesive strategy is based on the inhibition of the conidia adhesion at the surface of the broncho-pulmonary routes epithelium. These spores present a particularly high adhesion potential on alveolar pneumocytes forming the epithelium.

The first step aims at obtaining an alveolar pneumocytes layer in a 96 wells plate. Therefore approximately 40 000 cells are introduced in each well and are incubated for 7 days at 37° C. During this incubation time, the cells will deposit at the bottom of the wells in a homogeneous manner to reach a confluence and leave no empty space between the cells which come into contact with each other. In parallel, *Aspergillus fumigatus* is grown at 37° C. for 3 to 5 days. The spores are then carefully harvested in a PBS buffer solution while avoiding taking those which have evolved into filaments (hyphae). This solution is diluted to a concentration of 1 to $2 \times 10^6$ spores/mL and then preincubated with the various fucoside derivatives of the Invention in variable concentration.

This step allows the fucoside derivatives of the Invention to interact beforehand with the lectin AFL on *Aspergillus fumigatus*. Each of these solutions is then added to a well containing the layer of pneumocytes and then incubated at 37° C. for 45 minutes. The compounds having a large anti-adhesive potential will reduce the spore binding ability. Thus, after incubation, the spores present in the supernatant are eliminated by three rinsing steps. The spores adhered to the cellular layer are then counted under a microscope on an average surface of 400 pneumocytes.

ii. Results

To compare the multivalent effects of the different fucose derivatives of the Invention, the molar concentrations are given in relation to the amount of fucose moieties on the considered derivative and not in terms of molecules. For example, a 5 µM solution of divalent compound corresponds to a fucose concentration of 10 µM. This allows a direct comparison of the affinity gain of each fucose moiety on the multivalent scaffold. The activity of each compound was evaluated at two or three different concentrations in fucose equivalent (1, 10 and 100 µM; FIG. 4). The measurements were done three times.

The first information that can be obtained from this test is the absence of anti-adhesive activity of the monovalent compound 33 at the concentrations of 1 and 10 µM. The divalent compound 24 showed a decrease of 37% of the adhesion of the conidia at a high concentration of 100 µM. The fucose derivative 26, which had a high affinity for AFL in ITC tests (Example 35), presents a significant residual adhesion (76%) of the conidia on the pneumocytes, at 10 µM. This is fully coherent with ITC data and illustrating the critical role of the linker length in the antiadhesive effect.

Dextrane compound 31 has a significant anti-adhesive potential since an inhibition is observed event at the lowest tested concentration and a reduction in spore adhesion of 44% at a concentration of 10 µM. It should be noted that during the microscope counting of the number of residual conidia, we observed the formation of spore agglomerates, which testifies to the aggregative potential of this class of compounds.

The compounds having the highest potential of inhibition of adhesion of aspergillary spores are hexavalent fucose derivatives 29 and 30 with inhibitions of about 50% of conidia at a fucose concentration of 10 µM. Compound 29 having the shortest spacer had similar activity to the fucose derivative 30 whereas it was slightly less effective in ITC tests (Kd=0.60 µM for 29 against Kd=0.18 µM for 30). As discussed above, the results of the tests are expressed as a function of the effective concentrations of fucose. For a concentration of 10 µM in fucose, the molar concentration of compounds 29 or 30 is therefore 1.7 µM (six fucose moieties per molecule). The compounds 29 and 30 are therefore potent Conidia antiadhesives with a low IC50 of 1.7 µM.

Example 83: In Vitro Experiments

Compounds are evaluated against various clinical strains of *A. fumigatus* and species from the section *Fumigati* and section *Flavi*. For this purpose, a new test using fluorescent conidia and labelled pneumocytes is used during a 96 wells scanning spectrofluorimetric method.

Example 84: In Vivo Experiments

Outbred 6-week-old male CD1 (Charles River) mice (25 g) is immunosuppressed with an intraperitoneal injection of cyclophosphamide (150 mg/kg) and cortisone acetate (250 mg/kg). Before infection, mice is anesthetized with intraperitoneal pentobarbital (0.75 mg per mouse). In the first experiment, *A. fumigatus* conidia previously incubated with inhibitors is used for infection. In the second experiment, compounds to be evaluated are administrated by inhalation for prophylaxis strategy and before infection. *A. fumigatus* conidial suspension is injected intra-tracheal or for intranasal model, slowly pipetted into one of the nares. Evaluation of fungal burden is realized by quantitative polymerase chain reaction (PCR) and histopathologic staining.

The invention claimed is:

1. A compound bearing at least two fucose moieties and having a molecular weight of 0.6 to 340 kDa, said compound being of formula (I):

$$A\text{-}[(D)_i\text{-}B\text{—}C]_x \qquad (I)$$

wherein
i is equal to 0 or 1,
when i=0 formula (I) does not comprise D and A is linked to B,
when i=1 formula (I) comprises D;
A is selected from

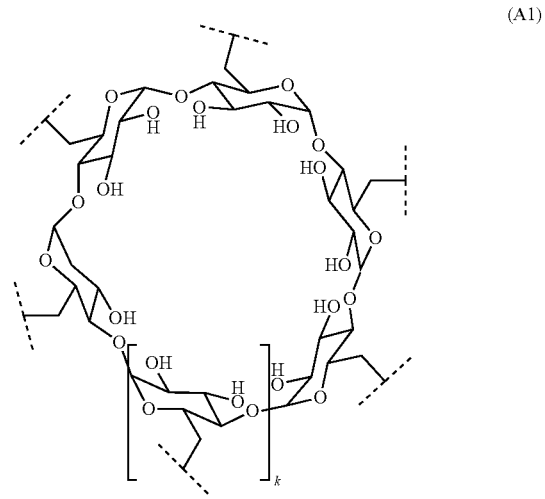

(A1)

k being equal to 1, or 3 and
when k=1, x is equal to 6,
when k=3, x is equal to 8;

(A2)

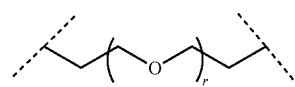

r being an integer of 1 to 30 and x being equal to 2;

(A3)

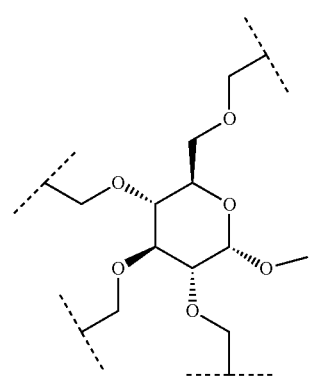

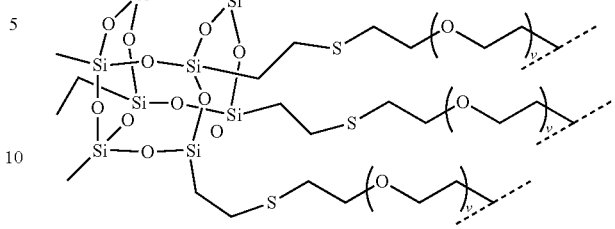

v being an integer of 0 to 10 and x being equal to 8;

B is of formula (B)

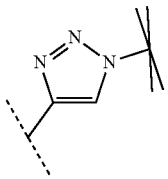

wherein B is of formula B1 when B group is linked to C group through the nitrogen atom of the triazole to form a B—C group of formula

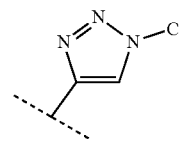

or B is of formula B2 when B group is linked to C group through its carbon atom to form a B—C group of formula

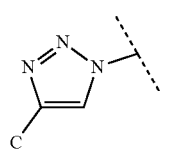

C is of formula (C)

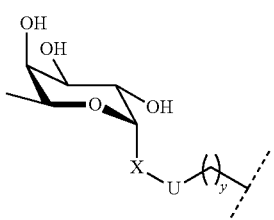

y being equal to 0 or 1;

X being selected from O, S or $CH_2$;

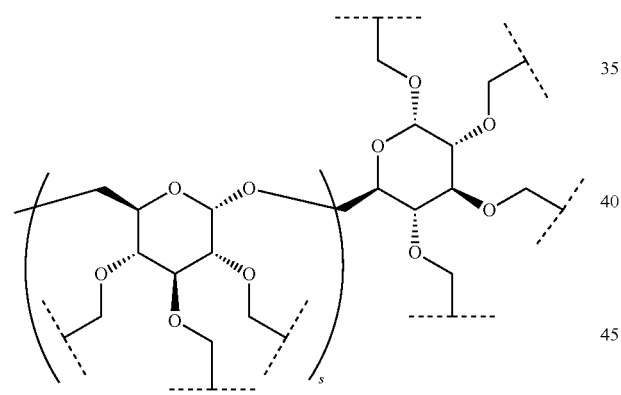

s being an integer of 5 to 300 and x being equal to (3s+8);

(A4)

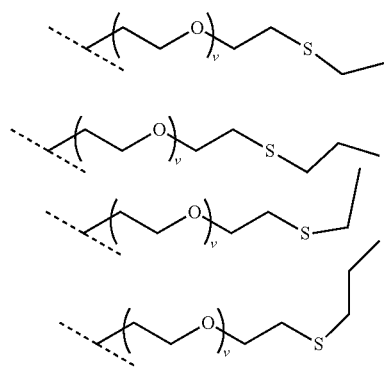

U being selected from

m being an integer of 0 to 8,

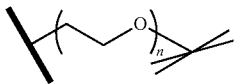

n being an integer of 0 to 8,

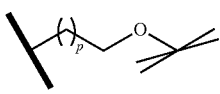

p being an integer of 1 to 10,

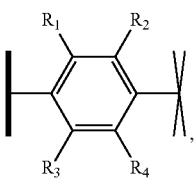

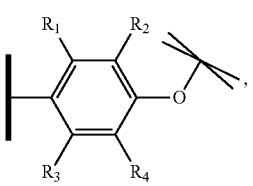

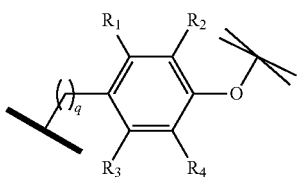

q being an integer of 1 to 10,

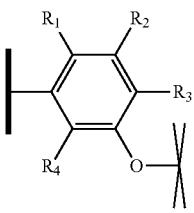

or

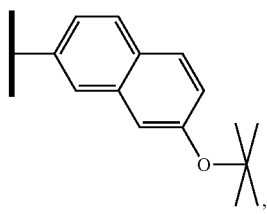

$R_1$, $R_2$, $R_3$ and $R_4$ being independently from each other selected from H, $COCH_3$, $NH_2$, $NO_2$, NHAc, OH, OMe, COOH, COOMe, CONHMe, Cl, Br, I, F, SMe or Me;

provided that y+n or y+m is different from 0;

D being selected from

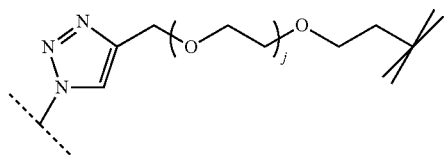

j being an integer of 0 to 8.

2. The compound according to claim 1 of formula (I)

$$A\text{-}[(D)_i\text{-}B\text{---}C]_x \quad (I)$$

wherein i is equal to 0 or 1, when i=0 formula (I) does not comprise D and A is linked to B, when i=1 formula (I) comprises D;

A is selected from

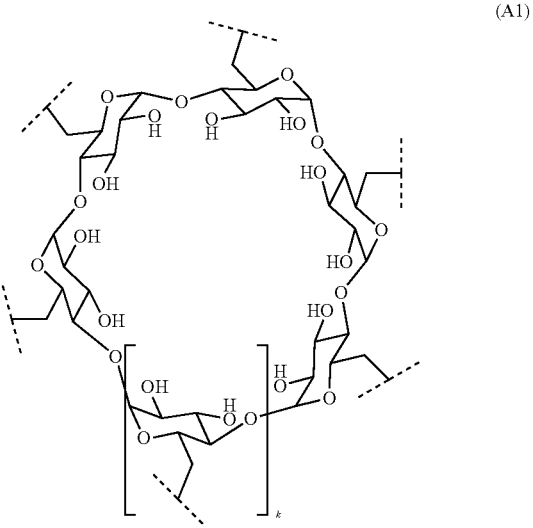

(A1)

k being equal to 1, or 3 and when k=1, x is equal to 6, when k=3, x is equal to 8;

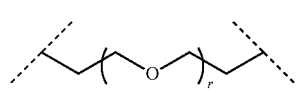
(A2)

r being an integer of 1 to 30 and x being equal to 2;

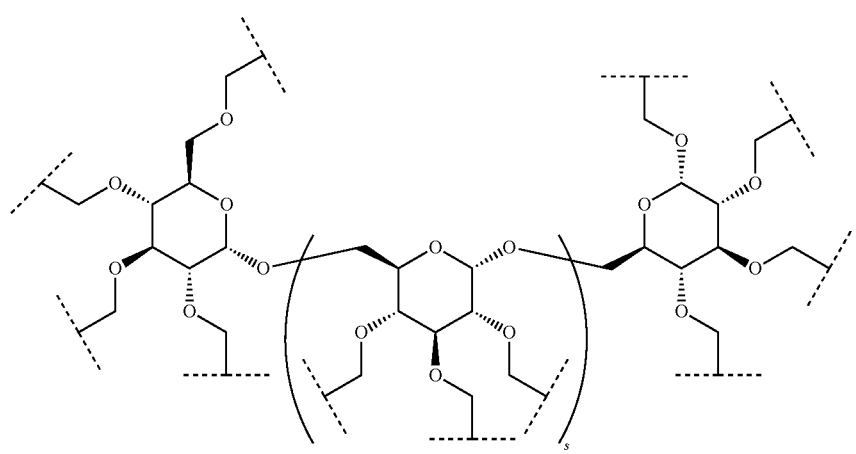
(A3)

s being an integer of 5 to 300 and x being equal to (3s+8);

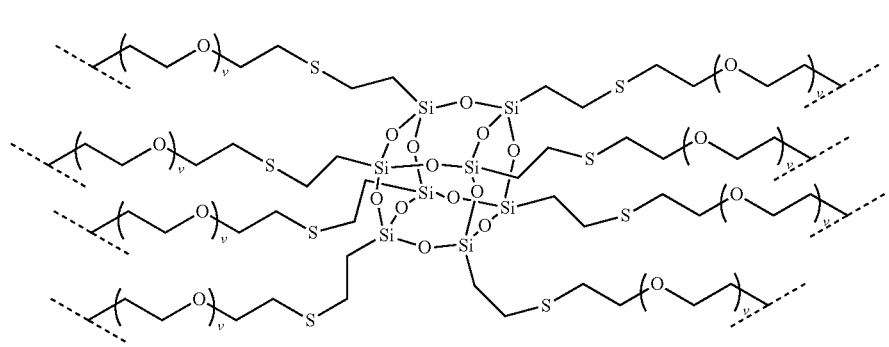
(A4)

v being an integer of 0 to 10 and x being equal to 8;
B is of formula

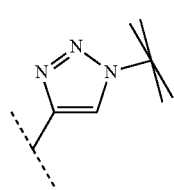
(B)

wherein B is of formula B1 when B group is linked to C group through the nitrogen atom of the triazole to form a B—C group of formula

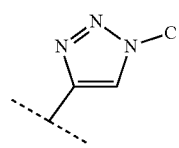

or B is of formula B2 when B group is linked to C group through its carbon atom to form a B—C group of formula

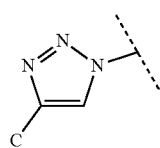

C is of formula

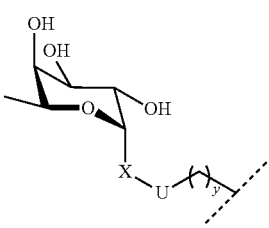
(C)

y being equal to 1;
X being selected from O, S or CH$_2$;
U being selected from

m being an integer of 0 to 8,

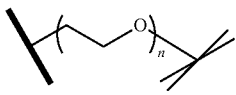

n being an integer of 0 to 8,

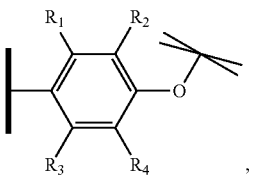

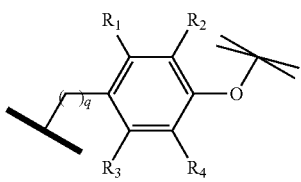

q being an integer of 1 to 10,
R$_1$, R$_2$, R$_3$ and R$_4$ being independently from each other selected from H, COCH$_3$, NH$_2$, NO$_2$, NHAc, OH, OMe, COOH, COOMe, CONHMe, Cl, Br, I, F, SMe or Me;
D being selected from

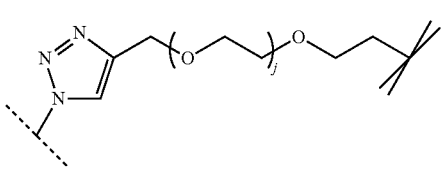

j being an integer of 0 to 8.

3. The compound according to claim 1, said compound being of formula (I-A1):

A1-[(D)$_i$-B—C]$_x$, wherein A being of formula A1 and having the following structure:

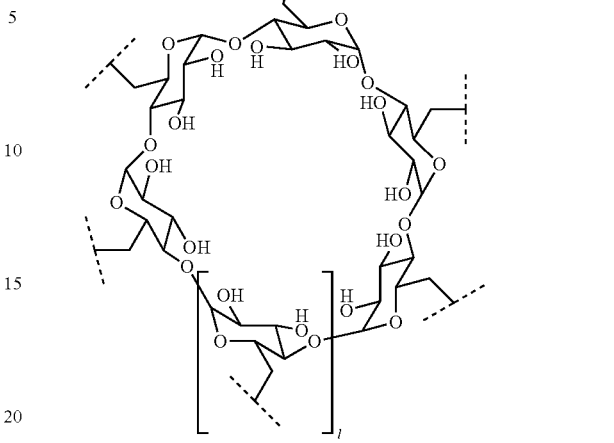

(A1-1)

k being equal to 1;
D$_i$, B and C being as defined in formula (I); or
said compound being of formula (I-A2):

A2-[(D)$_i$-B—C]$_2$, wherein A being of formula A2 and selected from

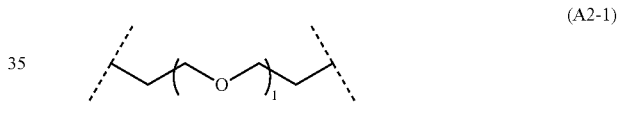

(A2-1)

r being equal to 1;

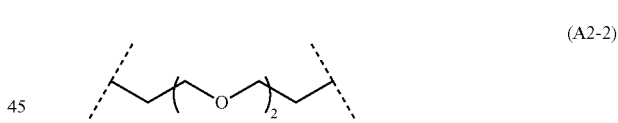

(A2-2)

r being equal to 2;

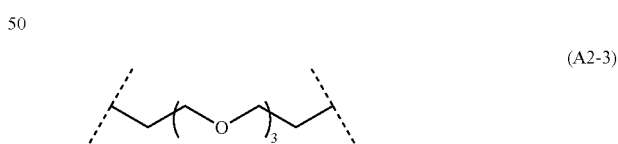

(A2-3)

r being equal to 3;

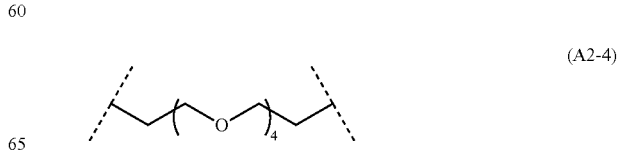

(A2-4)

r being equal to 4;

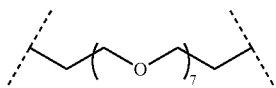
(A2-5)

r being equal to 7;

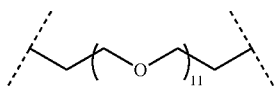
(A2-6)

r being equal to 11;

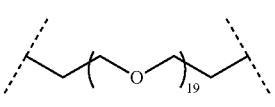
(A2-7)

r being equal to 19;

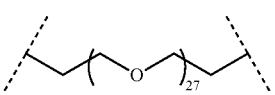
(A2-8)

r being equal to 27;
$D_i$, B and C being as defined in formula (I); or
said compound being of formula (I-A3):

A3-[(D)$_i$-B—C]$_x$, wherein A being of formula A3 and selected from

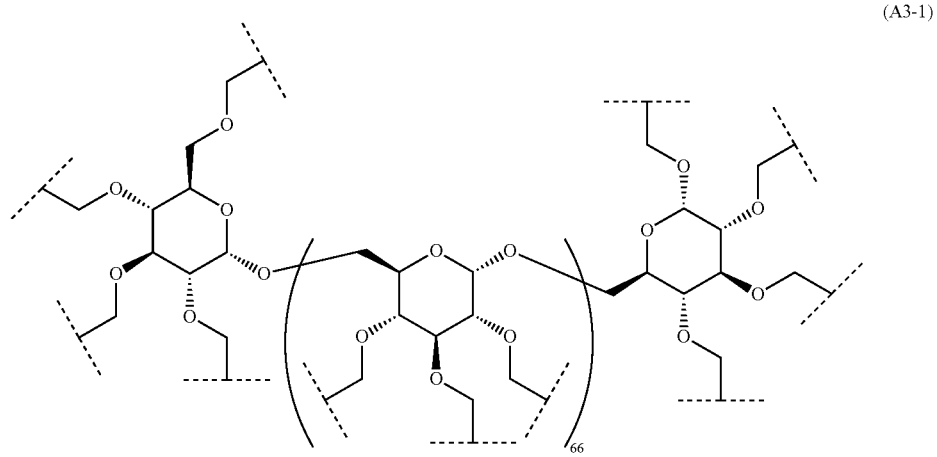
(A3-1)

s being equal to 66;
$D_i$, B and C being as defined in formula (I); or
said compound being of formula (I-A4):

A4-[(D)$_i$-B—C]$_8$, wherein A being of formula A4 and selected from

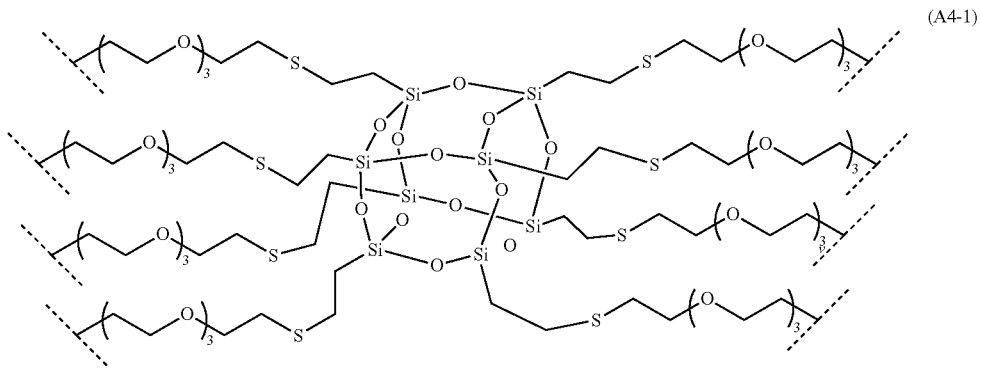
(A4-1)

$D_i$, B and C being as defined in formula (I).

4. The compound according to claim 1, said compound being of formula (I), wherein B is selected from B1 or B2,
   wherein B is of formula B1 when B group is linked to C group through the nitrogen atom of the triazole to form a B—C group of formula

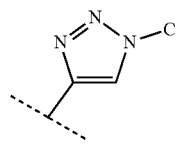

or B is of formula B2 when B group is linked to C group through its carbon atom to form a B—C group of formula

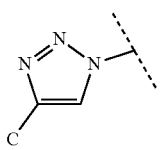

A, $D_i$ and C being as defined in formula (I).

5. The compound according to claim 1, said compound being of formula (I), wherein C is selected from C1, C2 or C3

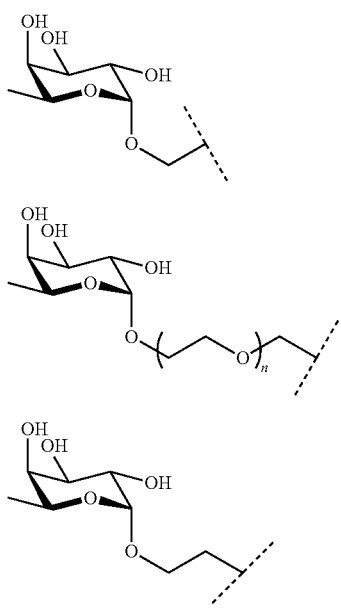

A, B and $D_i$ being as defined in formula (I).

6. The compound according to claim 1, said compound being of formula (I) wherein i is equal to 0 and said compound is of formula A-[B—C]$_x$, and wherein B—C is selected from the groups consisting of:
   [B2-C1],
   [B2-C2-1],
   [B2-C2-2], and
   [B1-C3];

A, B1, B2 and x being as defined in formula (I),
C1, C2-1, C2-2 and C3 being:

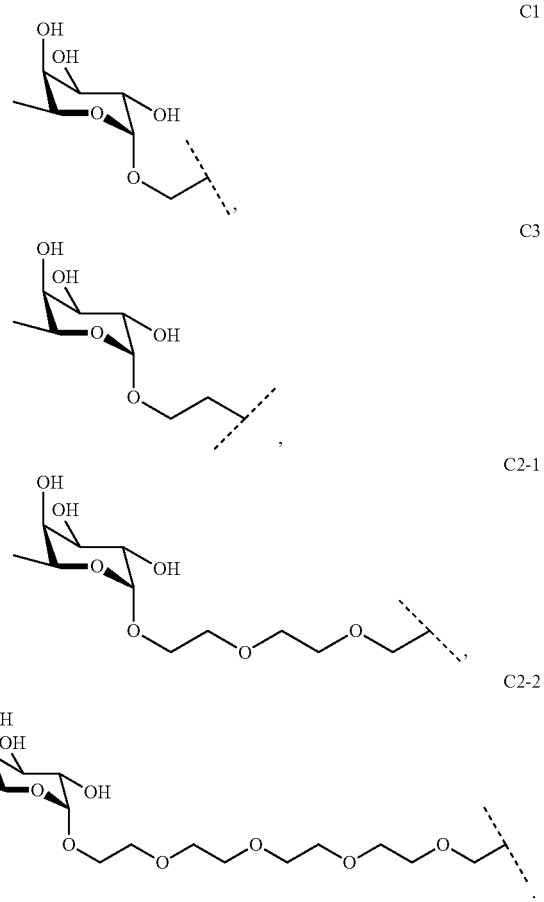

7. The compound according to claim 1, said compound being of formula selected from A1-[B2-C1]$_x$, A1-[B2-C2]$_x$,

A2-[B2-C1]$_2$,

A3-[B1-C3]$_x$,

A4-[B2-C1]$_8$,

A4-[B2-C2]$_8$,

A1, A2, A3, A4, B1, B2 and x being as defined in formula (I),
wherein C1, C2 and C3 being

C2
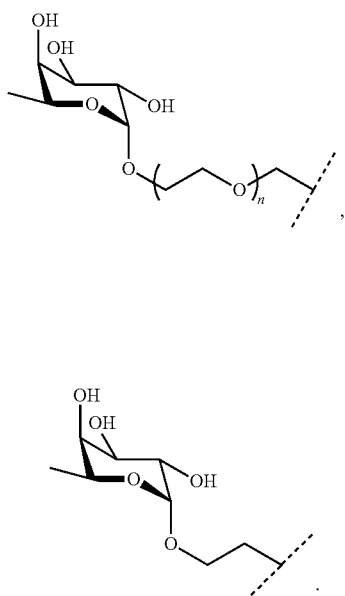
C3
8. A pharmaceutical composition comprising a compound having a molecular weight of 0.6 to 340 kDa,
said compound being of formula (I)
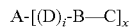 (I)
wherein
i is equal to 0 or 1,
when i=0 formula (I) does not comprise D and A is linked to B,
when i=1 formula (I) comprises D;
A is selected from
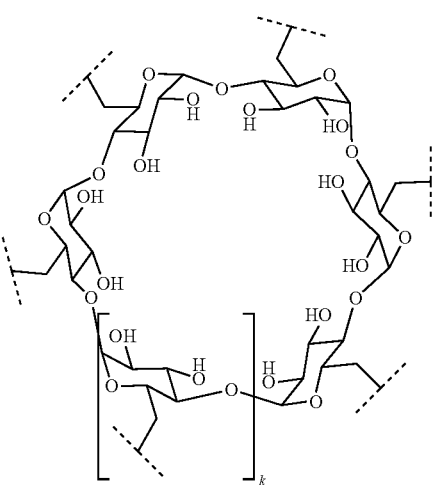
k being equal to 1, or 3 and
when k=1, x is equal to 6,
when k=3, x is equal to 8;
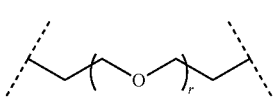
r being an integer of 1 to 30 and x being equal to 2;
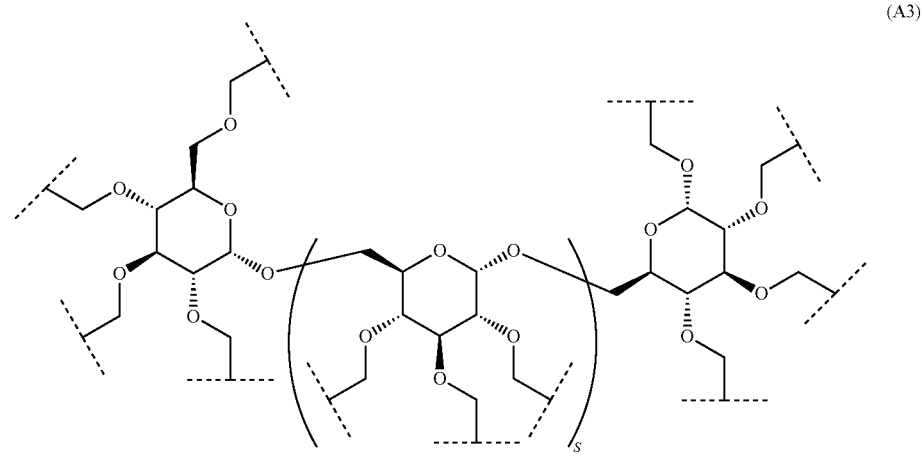

s being an integer of 5 to 300 and x being equal to (3s+8);

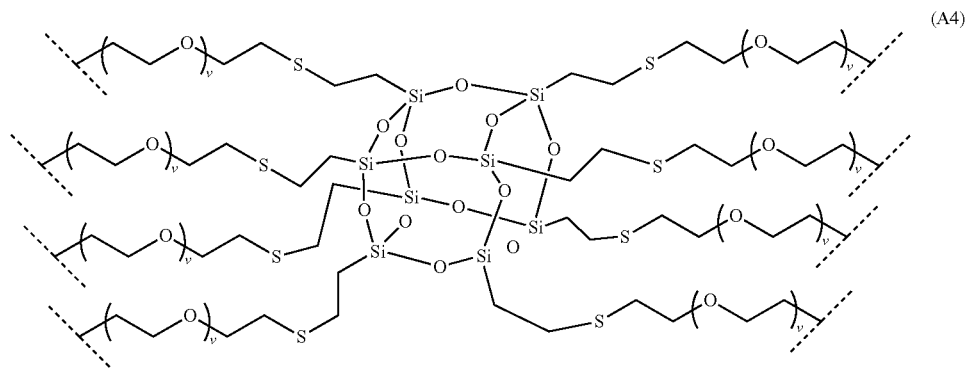

v being an integer of 0 to 10 and x being equal to 8;
B is of formula

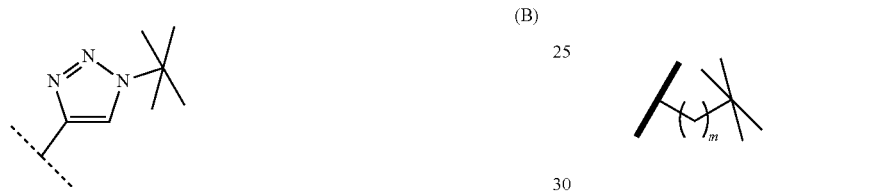

wherein B is of formula B1 when B group is linked to C group through the nitrogen atom of the triazole to form a B—C group of formula

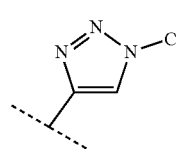

or B is of formula B2 when B group is linked to C group through its carbon atom to form a B—C group of formula

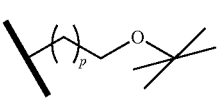

C is of formula

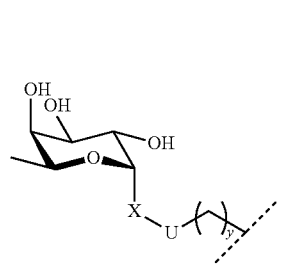

y being equal to 0 or 1;
X being selected from O, S or $CH_2$;
U being selected from m being an integer of 0 to 8, n being an integer of 0 to 8, p being an integer of 1 to 10,

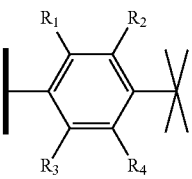

125
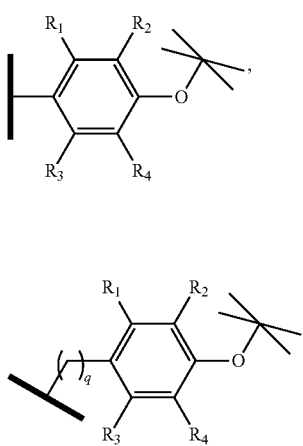
q being an integer of 1 to 10,
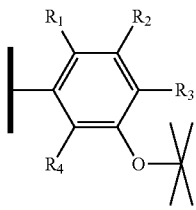
126
or
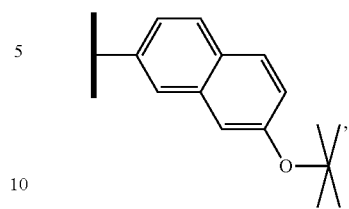
$R_1$, $R_2$, $R_3$ and $R_4$ being independently from each other selected from H, $COCH_3$, $NH_2$, $NO_2$, NHAc, OH, OMe, COOH, COOMe, CONHMe, Cl, Br, I, F, SMe or Me;
provided that y+n or y+m is different from 0;
D being selected from
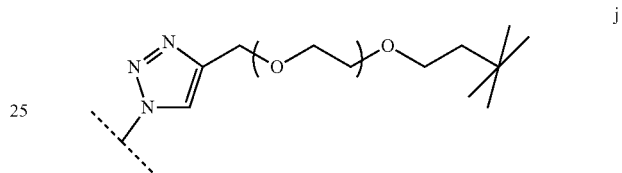
j being an integer of 0 to 8.
9. The compound according to claim 1, wherein said compound is selected from
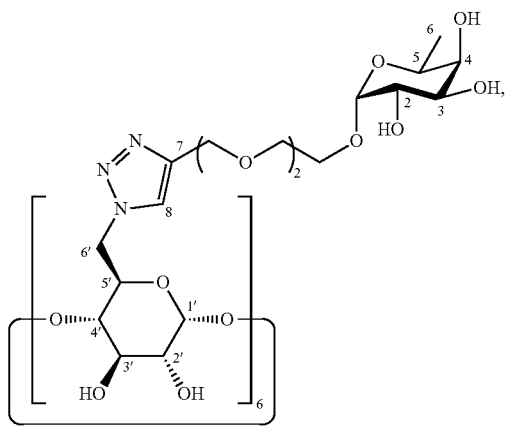
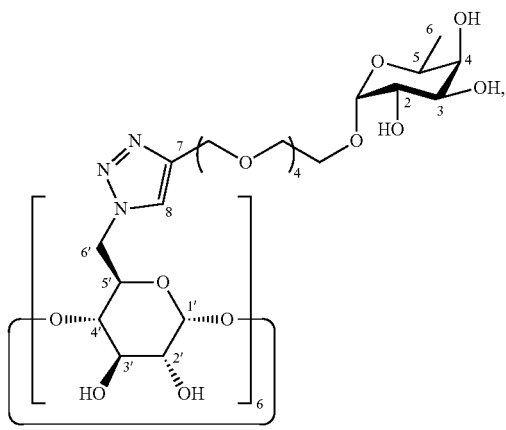
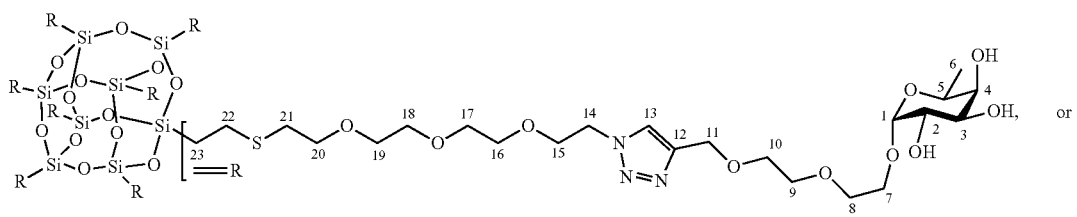
or

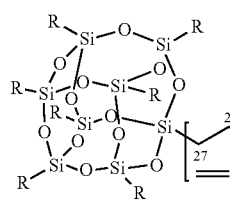

10. The compound according to claim 1, said compound being of formula (I), wherein C is selected from C2-1 and C2-2:

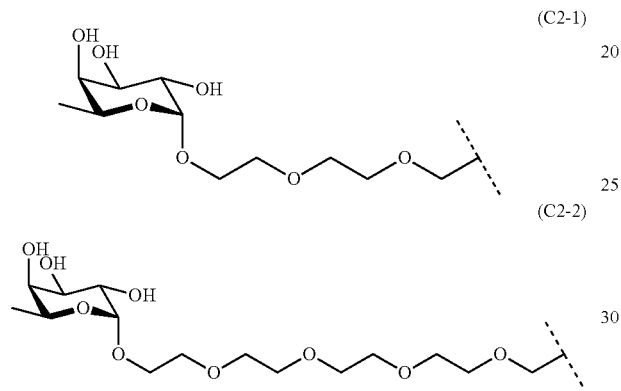

A, B and $D_i$ being as defined in formula (I).

11. The compound according to claim 1, said compound being of formula selected from A1-[B2-C2-1]$_x$, A1-[B2-C2-2]$_x$,

A4-[B2-C2-1]$_8$,

A4-[B2-C2-2]$_8$,

A1, A4, B1, B2 and x being as defined in formula (I), wherein C2-1 and C2-2 being

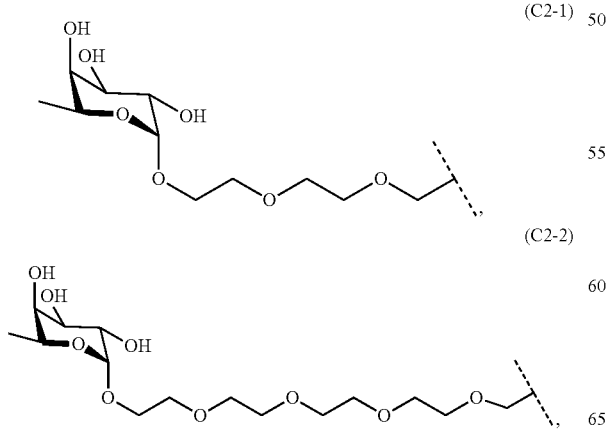

12. The compound according to claim 1, said compound being of formula selected from

A1-1-[B2-C1]$_6$,

A1-1-[B2-C2]$_6$,

A2-4-[B2-C1]$_2$,

A2-5-[B2-C1]$_2$,

A2-6-[B2-C1]$_2$,

A2-7-[B2-C1]$_2$,

A2-8-[B2-C1]$_2$,

A3-1-[B1-C3]$_x$,

A4-1-[B2-C1]$_8$,

A4-1-[B2-C2]$_8$,

B1, B2 and x being as defined in formula (I), wherein A1-1, A2-4, A2-5, A2-6, A2-7, A2-8, A3-1, A4-1, C1, C2, C3 being

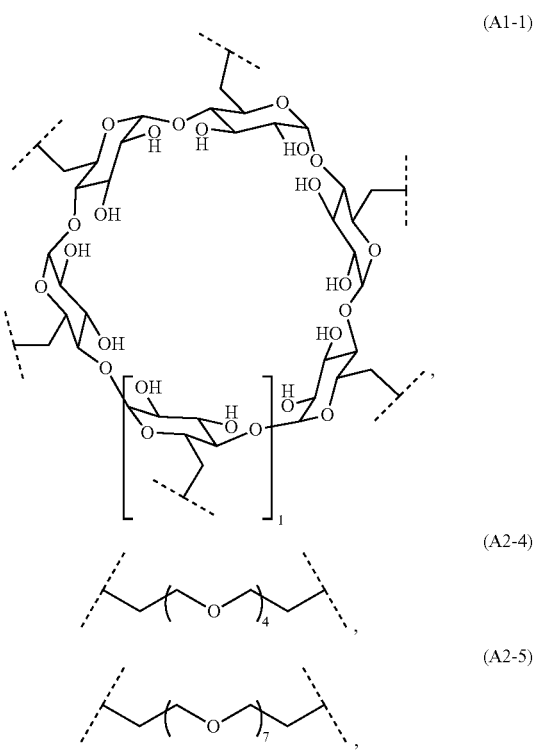

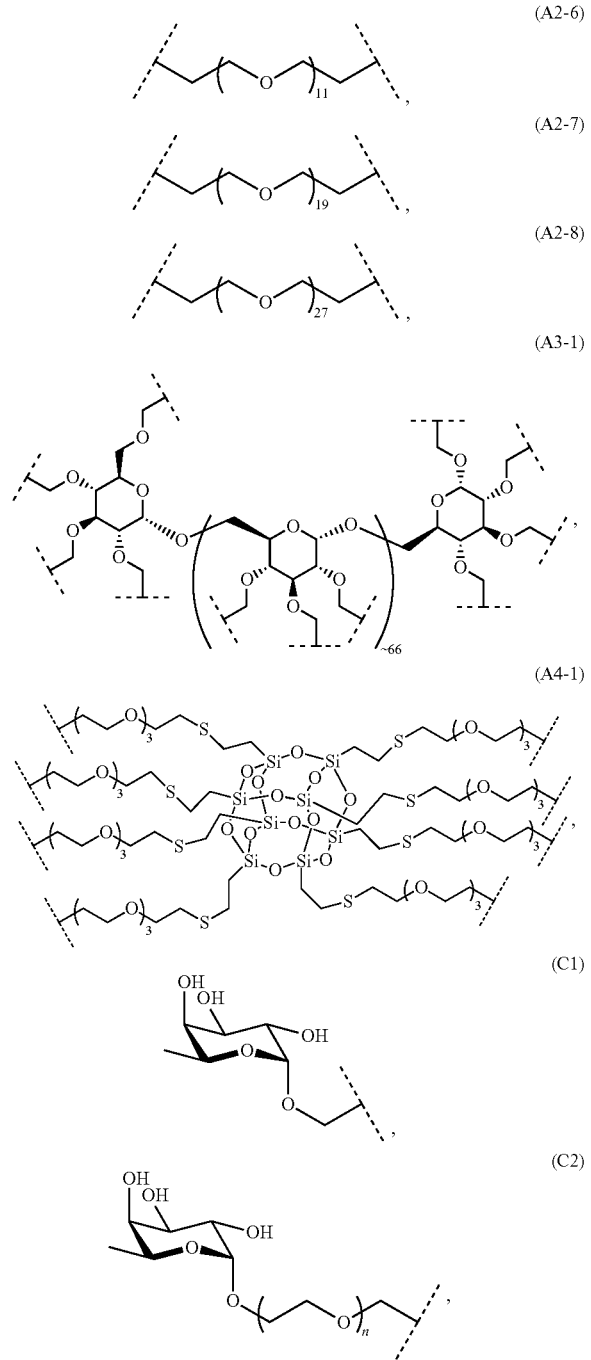

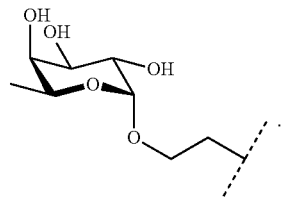

13. A method of treatment of infections caused by *Aspergillus* spp, comprising administering to a subject in need thereof an effective amount of a compound according to claim 1.

14. The method according to claim 13, wherein said compound is formulated in a composition.

15. The method according to claim 13, wherein said compound is in a composition, formulated for its human and/or animal use.

16. The method according to claim 13, wherein said compound is in a composition, said *Aspergillus* spp being *Aspergillus* section *Fumigati*, *Aspergillus* section *Flavi*, *Aspergillus* section *Nigri*, *Aspergillus* section *Nidulantes*, *Aspergillus oryzae*, *Aspergillus bombycis*, *Aspergillus nemius*.

17. The method according to claim 13, wherein said compound is in a composition, said infection being an aspergillosis, or an allergic broncho-pulmonary aspergillosis, an aspergilloma, a chronic pulmonary aspergillosis or an invasive pulmonary aspergillosis.

18. The method according to claim 13, wherein said compound is in a composition, said compound being used by respiratory route, by oral route or intravenously.

19. The method according to claim 13, wherein said compound is in a composition, wherein the composition comprises said compound from 1 mg to 1.4 g; or from 200 mg to 10 g; or from 10 mg to 10 g; or from 0.015 to 20 mg/kg; or from 3 mg/kg to 143 mg/kg; or from 0.15 mg/kg to 143 mg/kg.

20. The method according to claim 13, wherein said compound is in a composition, wherein the composition further comprises an antifungal agent selected from an azole antifungal agent, a polyene antifungal agent or an echinocandin antifungal agent.

* * * * *